US008598193B2

(12) United States Patent  
Bond et al.

(10) Patent No.: US 8,598,193 B2
(45) Date of Patent: Dec. 3, 2013

(54) POLYCYCLIC AGENTS FOR THE TREATMENT OF RESPIRATORY SYNCYTIAL VIRUS INFECTIONS

(75) Inventors: Silas Bond, Glen Waverley (AU); Vanessa Anne Sanford, Chelsea Heights (AU); John Nicholas Lambert, Blackburn South (AU); Chin Yu Lim, Clayton (AU); Jeffrey Peter Mitchell, Seaholme (AU); Alistair George Draffan, St. Kilda East (AU); Roland Henry Nearn, Chelsea Heights (AU)

(73) Assignee: Biota Scientific Management Pty Ltd., Notting Hill, Victoria (AU)

( * ) Notice: Subject to any disclaimer, the term of this patent is extended or adjusted under 35 U.S.C. 154(b) by 968 days.

(21) Appl. No.: 10/585,230

(22) PCT Filed: Dec. 24, 2004

(86) PCT No.: PCT/AU2004/001830
§ 371 (c)(1),
(2), (4) Date: Apr. 20, 2007

(87) PCT Pub. No.: WO2005/061513
PCT Pub. Date: Jul. 7, 2005

(65) Prior Publication Data
US 2007/0287700 A1    Dec. 13, 2007

(30) Foreign Application Priority Data

Dec. 24, 2003   (AU) .............................. 2003907196

(51) Int. Cl.
*A61K 31/44*        (2006.01)
*C07D 491/00*      (2006.01)

(52) U.S. Cl.
USPC ............................ 514/293; 546/82; 546/84

(58) Field of Classification Search
USPC ...................... 514/293; 546/82, 84
See application file for complete search history.

(56) References Cited

U.S. PATENT DOCUMENTS

| | | |
|---|---|---|
| 3,311,629 A | 3/1967 | Sulkowski |
| 3,379,733 A | 4/1968 | Houlinhan |
| 3,507,863 A | 4/1970 | Houlinhan |
| 3,590,043 A | 6/1971 | Graf |
| 3,624,101 A | 11/1971 | Sulkowski et al. |
| 3,657,221 A | 4/1972 | Sulkowski et al. |
| 3,770,766 A | 11/1973 | Sulkowski et al. |
| 3,885,037 A | 5/1975 | Sulkowski |
| 3,935,218 A | 1/1976 | Sulkowski |
| 3,966,955 A | 6/1976 | Shriver et al. |
| 1,058,529 A | 11/1977 | Graf et al. |
| 4,056,536 A | 11/1977 | Atkinson et al. |
| 4,058,529 A | 11/1977 | Graf et al. |
| 4,565,566 A | 1/1986 | Draber et al. |
| 4,701,208 A | 10/1987 | Los |
| 4,717,414 A | 1/1988 | Hunt |
| 4,726,838 A | 2/1988 | Durr et al. |
| 4,741,767 A | 5/1988 | Obrecht |
| 4,785,002 A | 11/1988 | Draber et al. |
| 4,846,876 A | 7/1989 | Draber et al. |
| 5,329,006 A | 7/1994 | Baumann et al. |
| 5,426,192 A | 6/1995 | Baumann et al. |
| 5,512,564 A | 4/1996 | Zilch et al. |
| 2007/0287700 A1 | 12/2007 | Bond et al. |
| 2010/0021458 A1 | 1/2010 | Mitchell et al. |

FOREIGN PATENT DOCUMENTS

| | | |
|---|---|---|
| BE | 687161 | 3/1967 |
| CA | 2104963 | 2/1992 |
| CA | 2108899 | 3/1992 |
| CA | 2108.899 | 9/1992 |
| CA | 2108899 | 9/1992 |
| CH | 481124 | 9/1966 |
| CH | 482697 | 3/1967 |
| CH | 481124 | 12/1969 |
| CH | 482697 | 1/1970 |
| EP | 183993 | 6/1986 |
| EP | 0475908 | 3/1992 |
| EP | 1207161 | 5/2002 |
| GB | 1038735 | 8/1966 |
| GB | 1105219 | 9/1966 |
| GB | 1059175 | 2/1967 |
| GB | 1229651 | 4/1971 |

(Continued)

OTHER PUBLICATIONS

Stephenson "New HIV prevention strategies urged," JAMA, 2004, vol. 292, No. 10, pp. 1163-1164.*

Aeberli et al., "The lithium aluminum hydride reduction products from heterocycles containing an isoindolone nucleus," J. Org. Chem., 1969, vol. 34(6), pp. 1720-1726.

Aeberli et al., "5-Aryl-2,3-dihydro-5H-imidazo[2,1-α]isoindo1-5-ols. A novel class of anorectic agents," J. Med. Chem., 1975, vol. 18(2), pp. 177-182.

Aeberli et al., "Anorectic agents. 2. Structural analogs of 5-(p-chlorophenyl)-2,3-dihydro-5H-imidazo[2,1-α]isoindo1-5-ol," J. Med. Chem., 1975, vol. 18(2), pp. 182-185.

(Continued)

*Primary Examiner* — Shengjun Wang
(74) *Attorney, Agent, or Firm* — Klarquist Sparkman, LLP

(57) ABSTRACT

Compounds of formula (I), and their use as in the treatment of infections involving viruses of the Pneumovirinae sub-family (RSV) are disclosed. In the formula ring (A) may be phenyl, pyridyl etc., (B—C) may be $CH_2$—$CH_2$ etc., ($R_1$) may be phenyl and substituted forms thereof, ($R_2$) may be assorted substituents.

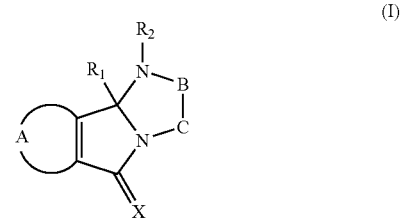

(I)

36 Claims, No Drawings

(56) References Cited

FOREIGN PATENT DOCUMENTS

| | | |
|---|---|---|
| GB | 1.322339 | 7/1973 |
| GB | 1322339 | 7/1973 |
| WO | WO 92/13863 | 8/1992 |
| WO | WO 92/16207 | 10/1992 |
| WO | WO 01/95910 | 12/2001 |
| WO | WO 0195910 | 12/2001 |
| WO | WO 02/26228 | 4/2002 |
| WO | WO 0226228 | 4/2002 |
| WO | WO 02/42326 | 5/2002 |
| WO | WO 02/066479 | 8/2002 |
| WO | WO 02/66479 | 8/2002 |
| WO | WO 02066479 | 8/2002 |
| WO | WO 03/040178 | 5/2003 |
| WO | WO 2005/061513 | 7/2005 |
| WO | WO 2006/116764 | 11/2006 |
| WO | WO 2008/037011 | 4/2008 |

OTHER PUBLICATIONS

Katrizky et al., "Convenient syntheses of dihydropyrrolo[2',1':3,4]pyrazino- and dihydropyrrolo[2',1':3,4][1,4]diazepino-[2,1-α]isoindolones," Tetrahedron Letters, 2002, vol. 43, pp. 2831-2833.

Katrizky et al., "Stereoselective syntheses of chiral (3S,9bS)-1,2-3,9b-tetrahydro-5H-imidazo[2,1-α]isoindol-5-ones," Tetrahedron Asymmetry, 2002, vol. 13, pp. 933-938.

Kruse et al., "Some benzyl-substituted imidazoles, triazoles, tetrazoles, pyridinethiones, and structural relatives as multisubstrate inhibitors of dopamine 13-hydroxylase. 4. Structure-activity relationships at the copper binding site," J. Med. Chem. 1990, vol. 33, pp. 781-789.

Metlesics et al., "The structure of the reaction product of O-benzoylbezoic acid with ethylenediamine," J. Org. Chem., 1967, vol. 32(7), pp. 2185-2187.

Sulkowski, et al., "2,5-Benzodiazocines and intermediates," J. Org. Chem., 1967, vol. 32(7), pp. 2180-2184.

Black, "Systematic review of the biology and medical management of respiratory syncytial virus infection," Respir. Care. 2003, vol. 48, pp. 209-233.

Evans Eds., In Viral Infections of Humans. Epidemiology and Control, 3rd ed., Plenum Medical Book, New York, pp. 525-544, 1989.

Falsey, "Noninfluenza respiratory virus infection in long-term care facilities," Infect. Control Hosp. Epidomiol. 1991, vol. 12, pp. 602-608.

Garvie et al., "Outbreak of respiratory syncytial virus infection in the elderly," Br. Med. J. 1980, vol. 281, pp. 1253-1254.

Hertz et al., "Respiratory syncytial virus-induced acute lung injury in adult patients with bone marrow transplants: a clinical approach and review of the literature," Medicine 1989, vol. 68, pp. 269-281.

Mufson et al., "Two distinct subtypes of human respiratory syncytial virus," J. Gen. Virol. 1985, vol. 66, pp. 2111-2124.

Van Den Hoogen et al., "A newly discovered human pneumovirus isolated from young children with respiratory tract disease," Nat. Med. 2001, vol. 7, pp. 719-724.

Van Den Hoogen et al., "Prevalence and clinical symptoms of human metapneumovirus infection in hospitalized patients," J. Infect. Dis. 2003, vol. 188, pp. 1571-1577.

Van Den Hoogen et al., "Clinical impact and diagnosis of human metapneumovirus infection," Pediatr. Infect. Dis. J. 2004, vol. 23(1 Suppl), pp. S25-S32.

Van Den Hoogen et al., "Analysis of the genomic sequence of a human metapneumovirus," Antivir. Ther. 1998, vol. 295, pp. 119-132.

Hall et al., "Aerosolized ribavirin treatment of infants with respiratory syncytial viral infection. A randomized double-blind study," N. Engl. J. Med. 1983, vol. 308, pp. 1443-1447.

Hall et al., "Ribavirin treatment of respiratory syncytial viral infection in infants with underlying cardiopulmonary disease," JAMA 1985, vol. 254, pp. 3047-3051.

Guion et al., "The Preparation of 2-(2-Oxo-2-Phenylethyl) Benzoic Acids from Dilithiated Ortho-Toluic Acid.," Synth. Comm. 1996, vol. 26, pp. 1753-1762.

Epsztajn et al., "Application of Organolithium and Related Reagents in Synthesis. Part 11. Metallation of 2-Methyl- and 4-Methylnicotinic Acids. A Useful Method for Preparation of AZA-Isocoumarins,".Synth. Comm. 1992, vol. 22, pp. 1239-1247.

Bruggink et al., "A study of the copper-catalysed direct arylation of β-dicarbonyl compounds with 2-bromobenzoic acids," Tetrahedron 1975, vol. 31, pp. 2607-2619.

Ames et al., "Heterocyclic synthesis from o-halogeno-acids. Part III. Synthesis of 2-inethylindole-4-carboxylic acid and related compounds and of some derivatives of 3-phenylisoquinolin-1(2H)-one," J. Chem. Soc. Perkin Trans. 1 1976, pp. 1073-1078.

Prasad et al., "18-Crown-6 as a catalyst in the dialkylation of o-nitrophenacyl derivatives," J. Org. Chem. 1991, vol. 56, pp. 7188-7190.

CAS Registry 1018992-94-3, Entered STN Feb. 5, 2008.
CAS Registry 1018993-09-3, Entered STN Feb. 5, 2008.
CAS Registry 1018993-12-8, Entered STN Feb. 5, 2008.
CAS Registry 1018993-14-0, Entered STN Feb. 5, 2008.
CAS Registry 1018993-19-5, Entered STN Feb. 5, 2008.
CAS Registry 1018993-20-8, Entered STN Feb. 5, 2008.
CAS Registry 1018997-73-3, Entered STN Feb. 5, 2008.
CAS Registry 1018997-85-7, Entered STN Feb. 5, 2008.
CAS Registry 1018997-90-4, Entered STN Feb. 5, 2008.
CAS Registry 1018998-06-5, Entered STN Feb. 5, 2008.
CAS Registry 1018998-11-2, Entered STN Feb. 5, 2008.
CAS Registry 1018998-14-5, Entered STN Feb. 5, 2008.
CAS Registry 1018998-54-3, Entered STN Feb. 5, 2008.
CAS Registry 1019001-78-5, Entered STN Feb. 5, 2008.
CAS Registry 1019001-81-0, Entered STN Feb. 5, 2008.
CAS Registry 1019001-85-4, Entered STN Feb. 5, 2008.
CAS Registry 1019001-88-7, Entered STN Feb. 5, 2008.
CAS Registry 1019006-25-7, Entered STN Feb. 5, 2008.
CAS Registry 1019006-29-1, Entered STN Feb. 5, 2008.
CAS Registry 1019006-52-0, Entered STN Feb. 5, 2008.
CAS Registry 1019006-57-5, Entered STN Feb. 5, 2008.
CAS Registry 1019006-62-2, Entered STN Feb. 5, 2008.
CAS Registry 1019006-75-7, Entered STN Feb. 5, 2008.
CAS Registry 1019006-78-0, Entered STN Feb. 5, 2008.
CAS Registry 1019006-82-6, Entered STN Feb. 5, 2008.
CAS Registry 1019006-92-8, Entered STN Feb. 5, 2008.
CAS Registry 717817-82-8, Entered STN Jul. 27, 2004.
CAS Registry 903154-09-6, Entered STN Aug. 22, 2006.
CAS Registry 104024-49-9, Entered STN Aug. 30, 1986.

Non-Final Office Action from corresponding U.S. Appl. No. 12/443,177 dated Oct. 29, 2012.

Non-Final Office Action from corresponding U.S. Appl. No. 13/023,473 dated Oct. 30, 2012.

van den Hoogen et al., "Analysis of the genomic sequence of a human metaphenumorivus," Virology 295:119-132, 2002.

The Chemical Society of Japan, Separation of Enantiomers, Quarterly Journal, Chemical Review, 6:5, 1989.

CAS Registry 1018992-94-3, 2008.
CAS Registry 1018993-09-3, 2008.
CAS Registry 1018993-12-8, 2008.
CAS Registry 1018993-14-0, 2008.
CAS Registry 1018993-19-5, 2008.
CAS Registry 1018993-20-8, 2008.
CAS Registry 1018997-73-3, 2008.
CAS Registry 1018997-85-7, 2008.
CAS Registry 1018997-90-4, 2008.
CAS Registry 1018998-06-5, 2008.
CAS Registry 1018998-11-2, 2008.
CAS Registry 1018998-14-5, 2008.
CAS Registry 1018998-54-3, 2008.
CAS Registry 1019001-78-5, 2008.
CAS Registry 1019001-81-0, 2008.
CAS Registry 1019001-85-4, 2008
CAS Registry 1019001-88-7, 2008.
CAS Registry 1019006-25-7, 2008.
CAS Registry 1019006-29-1, 2008.

(56) References Cited

OTHER PUBLICATIONS

CAS Registry 1019006-52-0, 2008
CAS Registry 1019006-57-5, 2008.
CAS Registry 1019006-62-2, 2008
CAS Registry 1019006-75-7, 2008.
CAS Registry 1019006-78-0, 2008.
CAS Registry 1019006-82-6, 2008.
CAS Registry 1019006-92-8, 2008.
CAS Registry 717817-82-8, 2004.
CAS Registry 903154-09-6, 2006.
Chemical Abstract: CA 105:110514 RN104024-49-9, 1986.
Non-Final Office Action dated Apr. 20, 2011, from U.S. Appl. No. 12/443,177.
Final Office Action dated Nov. 8, 2011, from U.S. Appl. No. 12/443,177.
Stephenson, "New HIV prevention strategies urged," *JAMA* 292(10):1163-1164, 2004.
CAS Registry 327979-63-5, Entered STN Mar. 19, 2001.
CAS Registry 477867-90-6, Entered STN Dec. 31, 2002.
CAS Registry 477886-49-0, Entered STN Dec. 31, 2002.
Yamaguchi et al., "Novel antiasthmatic agents with dual activities of thromboxane $A_2$ synthetase inhibition and bronchodilation. 1. 2-[2-(1-Imidazolyl)alkyl]-1(2H)-phthalazinones," J. Med. Chem., 1993, vol. 36, pp. 4052-4060.
Natsugari et al., "Novel, potent, and orally active substance P antagonists: synthesis: and antagonist activity of N-benzylcarboxamide derivatives of pyrido[3,4-b]pyridine," J. Med. Chem., 1995, vol. 38, pp. 3106-3120.
Sulkowski et al., "2,5-Benzodiazocines and intermediates," J. Org. Chem., 1967, vol. 32, pages: 2180-2184.
Aeberli et al., "Anorectic agents. 2. Structural analogs of 5-(p-chlorophenyl)-2.3-dihydro-5H-imidazo[2.1-a]isoindol-5-ol," J. Med. Chem., 1975, vol. 18, pp. 182-185.
Kruse et al., "Some benzyl-substituted imidazoles, triazoles, tetrazoles, pyridinethiones, and structural relatives as multisubstrate inhibitors of dopamine beta-hydroxylase. 4. Structure-activity relationships at the copper binding site," J. Med. Chem., 1990, vol. 33, pp. 781-789.
Watanabe et al., "MTT colorimetric assay system for the screening of anti-orthomyxo- and anti-paramyxoviral agents," J. Virological Methods, 1994, vol. 48, pp. 257-265.
Morton et al., "Structural characterization of respiratory syncytial virus fusion inhibitor escape mutants: homology model of the F protein and a syncytium formation assay," Virology, 2003, vol. 311. pp. 275-288.
Wyde et al., "Short duration aerosols of JNJ 2408068 (R 170591) administered prophylactically or therapeutically protect cotton rats from experimental respiratory syncytial virus infection," Antiviral Res., 2003, vol. 60, pp. 221-231.
Cianci et al., "Orally active fusion inhibitor of respiratory syncytial virus," Antimicrobial Agents and Chemotherapy. 2004, vol. 48, pp. 413-422.
Metlesics et al., "Structure of the reaction product of o-benzoyl-benzoic acid with ethylenediamine," J. Org. Chem., 1967, vol. 32, pp. 2185-2187.
CA abstract 67:43744 and RN 13449-92-8, 1967.
CA abstract 67:43799 and RNs 5810-68-4, 5983-39-1, 5983-45-9, 13450-15-2, 1967.
CA abstract 71:38862 and RNs 5983-38-0, 5983-39-1, 1971.
CA abstract 137:337826 and RN 473998-86-6, 2002.

\* cited by examiner

POLYCYCLIC AGENTS FOR THE TREATMENT OF RESPIRATORY SYNCYTIAL VIRUS INFECTIONS

This application is the U.S. National Stage Application of International Patent Application No. PCT/AU2004/001830, filed on Dec. 24, 2004, which claims priority to Australian Patent Application No. 2003907196, filed on Dec. 24, 2003, all of which are incorporated herein by reference in their entirety.

FIELD OF THE INVENTION

The present invention relates to antiviral compounds, methods for their preparation and compositions containing them, and use at the compounds and composition in the treatment of viral infections. In particular, the invention relates to the use of compounds of formula I for the treatment of respiratory syncytial virus infection.

BACKGROUND ART

Respiratory syncytial virus (RSV) is the leading cause of lower respiratory tract infection in adults and in young children. In the western world approximately all children have been infected by the age of two. In most cases the RSV infections will only cause minor upper respiratory illness with symptoms resembling that of the common cold. However, severe infection with the virus may result in bronchiolitis or pneumonia which may result in hospitalization or death. Infants who have been born prematurely or have a pre-existing lung disease are a high risk of severe infection and complications.

Respiratory syncytial virus (RSV) is a member of the order Mononegalirales, which consists of the non-segmented negative strand RNA viruses in the Families Paramyxoviridae, Rhabdoviridae and Filoviridae. RSV of humans (often termed RSV or HRSV) is a member of the Pneumovirus genus of the sub-family Pneumovirinae within the Family Paramyxoviridae. Other members of the Pneumovirus genus include viruses such as bovine RSV (BRSV), ovine RSV (ORSV) and murine pneumonia virus (MPV) amongst others. The sub-family Pneumovirinae also includes the genus Metapneumovirus which contains the recently identified and important human pathogen human metapneumovirus.

In addition to the genome features described above, Family characteristics include a lipid envelope containing one or more glycoprotein species considered to be associated with attachment and entry, of the host cell. Entry is considered to require a process by which the viral envelope fuses with the membrane of the host cell. Fusion of infected cells with, for example, their neighbours, can also result in the formation of fused multinucleate cells known as syncytia in some cases. The fusion process is believed to be glycoprotein mediated and is a feature shared with diverse enveloped viruses in other taxonomic groups. In the case of the Paramyxoviridae viruses of all genera characteristically express a fusion glycoprotein (F) which mediates membrane fusion The only drug currently approved for the treatment of severe RSV is the antiviral medication, Virazole, also known as Ribavirin. This agent has a broad spectrum antiviral with virustatic effects, and acts by inhibiting RSV replication. It also improves arterial blood oxygenation. Unfortunately, the agent is toxic so that administration of the agent is confined to a hospital setting. Its administration is further complicated by the need to follow a strict procedural process when administering the agent in order to minimise the likelihood of certain adverse affects. The agent has a number of adverse effects including sudden deterioration of respiratory function (bronchiospasm). The efficacy of the agent has remained controversial and thus there is a real need to find an alternative agent for the treatment of RSV infection.

A number of agents are known to inhibit RSV. Published patent applications WO 01/95910 and WO 02/26228 (Bristol Myers Squib Company), the contents of which are incorporated by cross reference, describe a number of different types of compounds which exhibit anti-RSV activity in their description of the background art. Moreover, these applications describe compounds having antiviral activity against RSV of the formula

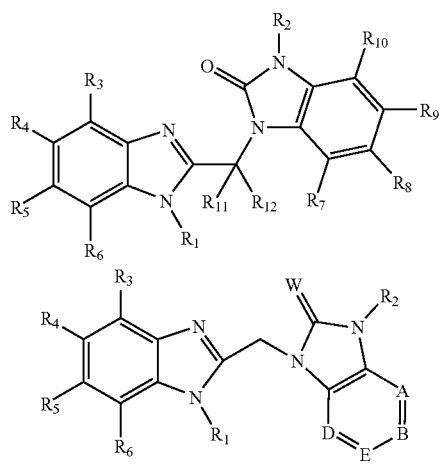

There are also a number of patent specifications that disclose imidazo-[2,1-a]-isoindole derivatives for uses other than treating RSV. U.S. Pat. No. 3,507,863 describes a number of polycyclic compounds that have anti-inflammatory and anti-convulsive activity. These compounds have the following general structure

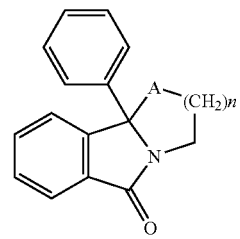

where A is —NH—, —O— or —S—, and n is 1-3.

U.S. Pat. No. 3,770,766 describes polycyclic compounds that have antidepressant activity, and have the following general structure

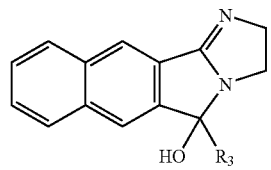

where $R_3$ is selected from various aromatic substituents.

U.S. Pat. No. 4,058,529 discloses anti-inflammatory and anti-convulsive activity polycyclic compounds of the general formula A, and includes compounds of the formula B where $R_2$ is hydrogen or lower alkyl group (including amino substituted groups) and n is 1-3.

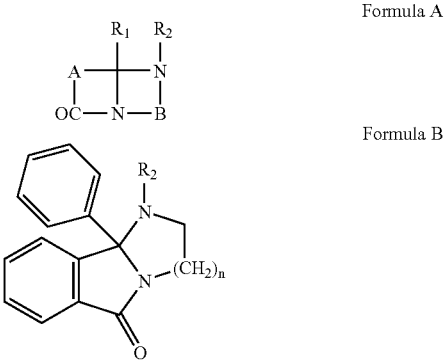

CH 482,697 (Graf) discloses a number of compounds of the general formula B above, where $R_2$ is —CO—CHR—$N_3$ and R is hydrogen or alkyl, and intermediates where $R_2$ is —CO—CHR—$NH_2$, —CO—CHR—OH or hydrogen. Likewise U.S. Pat. No. 3,590,043 (Graf) relates to compounds of the formula B where $R_2$ is —CO—CHR—NR'R". In this document n is 1 to 3, R is H or lower alkyl, R' and R" may be lower alkyl or benzyl or together form a piperidinyl or morpholinyl ring. The Graf compounds may have anti-inflammatory uses.

WO 02/066479 (Banyu Pharmaceutical) lists some compounds of the general formula B, where $R_2$ is lower alkyl, —CO—$C_2H_5$ and selected other moieties. It also appears to suggest a compound of formula B where the fused phenyl ring has been replaced with pyridyl and $R_2$ is methyl. It is not clear whether all of these compounds have been made. The compounds are for use in the treatment of high blood pressure and diabetes.

GB 1,038,735 discloses anti-inflammatory compounds of the general formula B, where n is 1 to 3, $R_2$ is lower alkyl or, for example, an dimethylaminoethyl group.

Canadian patent application no. 2,108,899 (also see family member WO 92/16207) discloses various oxazolo-[2,3-a]-isoindole and imidazo-[2,1-a]-isoindole derivatives for use in antiviral medicaments, particularly for use in the treatment of AIDS and HIV. There are marked differences between HIV and RSV viruses, the diseases they are associated with, and the respective modes of action of the disclosed compounds. The specification generally describes compounds of the structure below where R is $C_1$-$C_6$ alkyl group or $C_1$-$C_6$ acyl group, and specifically discloses compounds where R is —$COCH_3$ or —$CH_3$.

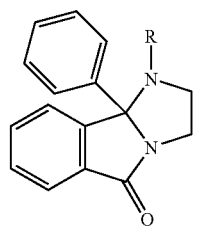

A number of documents disclose compounds of the above formula or substituted forms thereof, where R is hydrogen. See for example the herbicidal compounds disclosed in U.S. Pat. Nos. 4,726,838 and 4,846,876.

SUMMARY OF THE INVENTION

The invention relates to the discovery that certain compounds exhibit favourable anti-RSV activity by inhibition of the RSV virus's essential fusion processes.

This invention provides for the use of a compound of formula I

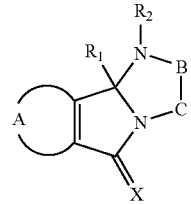

its salts, and pharmaceutically acceptable derivatives thereof, in the treatment of respiratory syncytial virus (RSV) infections, wherein $R_1$ is selected from $C_{1-12}$ alkyl, $C_{2-12}$ alkenyl, $C_{2-12}$ alkynyl, —$(CH_2)_nC_{3-7}$ cycloalkyl, —$(CH_2)_nC_{4-7}$ cycloalkenyl, —$(CH_2)_n$ aryl, —$(CH_2)_n$ aryl$C_{1-12}$ alkyl, —$(CH_2)_n$ aryl$C_{2-12}$ alkenyl, —$(CH_2)_n$ aryl$C_{2-12}$ alkynyl, and —$(CH_2)_n$ heterocyclyl; n is 0-6 and said alkyl, alkenyl, alkynyl, cycloalkyl, cycloalkenyl, aryl and heterocyclyl groups are optionally substituted;

$R_2$ is selected from —$CH_2R_3$, —$C(Y)R_3$, —$C(Y)OR_3$, —$C(Y)N(R_4)R_3$, —$C(Y)CH_2N(R_4)R_3$, —$C(Y)CH_2SR_3$ and —$S(O)_wR_5$, where $R_3$ is selected from hydrogen, $C_{1-12}$ alkyl, $C_{2-12}$ alkenyl, $C_{2-12}$ alkynyl, —$(CH_2)_mC_{3-7}$ cycloalkyl, —$(CH_2)_mC_{4-7}$ cycloalkenyl, —$(CH_2)_m$ aryl, —$(CH_2)_m$ aryl$C_{1-12}$ alkyl, —$(CH_2)_m$ aryl$C_{2-12}$ alkenyl, —$(CH_2)_m$ aryl$C_{2-12}$ alkynyl and —$(CH_2)_m$ heterocyclyl; and when $R_2$ is —$CH_2R_3$, or —$C(Y)R_3$, $R_3$ may also be selected from —S—$R_5$ and —O—$R_5$; m is 0-6; $R_4$ is hydrogen or $C_{1-6}$ alkyl; $R_5$ is $C_{1-6}$ alkyl, $C_{2-6}$ alkenyl, $C_{2-6}$ alkynyl, $C_{3-7}$ cycloalkyl, $C_{4-7}$ cycloalkenyl, benzyl, aryl or heterocyclyl; w is 0, 1 or 2, and the alkyl, alkenyl, alkynyl, cycloalkyl, cycloalkenyl, aryl and heterocyclyl groups are optionally substituted;

X and Y are independently selected from O, S and $NR_6$, where $R_6$ is independently selected from hydrogen, lower alkyl, hydroxy and lower alkoxy;

A together with the atoms to which it is attached, forms an optionally substituted aromatic ring;

B—C together with the atoms to which they are attached, forms an optionally substituted heterocyclic ring having from 5 to 8 ring atoms.

The invention also provides for the use of compounds of formula I, its salts, and pharmaceutically acceptable derivatives thereof, in the treatment of RSV infections by the inhibition of the virus's fusion processes.

The invention also provides novel compounds of formula I, their salts, and pharmaceutically acceptable derivatives thereof.

DESCRIPTION OF PREFERRED EMBODIMENTS

As used herein the term "aromatic" refers to aryl rings or ring systems and aromatic heterocyclic rings or ring systems, as known as heteroaryl or heteroaromatic rings.

As used herein the term "aryl" refers to carbocyclic (non-heterocyclic) aromatic rings or ring systems. The aromatic rings may be mono- or bi-cyclic ring systems. The aromatic rings or ring systems are generally composed of 5 to 10 carbon atoms. Examples of suitable aryl groups include but are not limited to phenyl, biphenyl, naphthyl, tetrahydronaphthyl, and the like.

Preferred aryl groups include phenyl, naphthyl, indenyl, azulenyl, fluorenyl or anthracenyl.

The term "heterocyclic" or "heterocyclyl" as used herein refers to mono or bicyclic rings or ring systems that include one or more heteroatoms selected from N, S and O. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as furyl, thienyl and pyrrolyl rings.

Examples of 5-membered monocyclic heterocycles include furyl, thienyl, pyrrolyl, H-pyrrolyl, pyrrolinyl, pyrrolidinyl, oxazolyl, oxadiazolyl, (including 1,2,3 and 1,2,4 oxadiazolyls) thiazolyl, isoxazolyl, furazanyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls). Examples of 6-membered monocyclic heterocycles include pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino.

The heterocycle may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl, pteridinyl and the like. These heterocycles may be optionally substituted, for example with $C_{1-6}$alkyl, $C_{1-6}$alkoxy, $C_{2-6}$alkenyl, $C_{2-6}$alkynyl, halo, hydroxy, mercapto, trifluoromethyl, amino, cyano or mono or di($C_{1-6}$alkyl)amino.

Examples of preferred heterocyclic radicals include (optionally substituted) isoxazoles, isothiazoles, 1,3,4-oxadiazoles, 1,3,4-thiadiazoles, 1,2,4-oxadiazoles, 1,2,4-thiadiazoles, oxazoles, thiazoles, pyridines, pyridazines, pyrimidines, pyrazines, 1,2,4-triazines, 1,3,5-triazines, benzoxazoles, benzothiazoles, benzisoxazoles, benzisothiazoles, quinolines and quinoxalines. These heterocycles can be optionally substituted with, by example, with $C_{1-6}$alkyl, $C_{1-6}$alkoxy, $C_{2-6}$alkenyl, $C_{2-6}$alkynyl, halo, hydroxy, mercapto, trifluoromethyl, amino, cyano or mono or di($C_{1-6}$alkyl)amino.

Examples of particularly preferred heterocyclic radicals include furyl, thienyl, pyridyl, oxazolyl, thiazolyl, pyrazolyl, furazanyl, isoxazolyl, isothiazolyl, 1,2,3-triazolyl, 1,3,4-triazolyl, 1,2,3-thiadiazolyl, 1,3,4-thiadiazolyl, pyridazinyl, pyrimidinyl, benzo[b]furanyl, benzo[b]thiophenyl and benzoisoxazolyl.

Examples of unsaturated 5-membered heterocyclic rings include oxazole, thiazole, imidazole, 1,2,3-triazole, isoxazole, isothiazole, pyrazole, furan, thiophene and pyrrole. Examples of unsaturated 6-membered heterocyclic rings include pyridine, pyrimidine, pyrazine, pyridazine and 1,2,4-triazine.

In a preferred embodiment, the heterocyclic ring is an aromatic ring. Heteroaryl and heteroaromatic are used herein to refer to this subset of heterocyclic rings. Heteroaryl rings include furyl, thienyl, pyridyl, pyrrolyl, oxazolyl, thiazolyl, imidazolyl, pyrazolyl, isoxazolyl, isothiazolyl, 1,2,3-oxadiazolyl, 1,2,4-oxadiazol-5-one, 1,2,3-triazolyl, 1,3,4-thiadiazolyl, pyridazinyl, pyrimidinyl, pyrazinyl, 1,3,5-triazinyl, 1H thieno[2,3-c]pyrazolyl, thieno[2,3-b]furyl, indolizinyl, indolyl, isoindolyl, 3H-indolyl, indolinyl, benzo[b]furanyl, benzo[b]thiophenyl, 1H-indazolyl, benzimidazolyl, tetrazolyl, uridinyl, and cytosinyl.

More preferably heteroaryl or heteroaromatic is selected from isoxazolyl, oxazolyl, imidazolyl, thiazolyl, thiadiazolyl, isothiazolyl, furazanyl, triazolyl, pyridyl, pyrimidinyl, furyl, pyrazolyl, pyridazinyl, thienyl and aryl fused heteroaromatic rings such as benzfuranyl, benzothiophenyl and benzoisoxazolyl.

In another preferred embodiment, the heterocyclic ring is a non-aromatic ring selected from the group consisting of pyrrolidine, imidazoline, 2-imidazolidone, 2-pyrrolidone, pyrrolin-2-one, tetrahydrofuran, 1,3-dioxolane, piperidine, tetrahydropyran, oxazoline, 1,3-dioxane, 1,4-piperazine, morpholine and thiomorpholine.

The heterocyclic ring containing the linker group B—C may be selected from the above described heterocyclic rings provided the ring meets the requirement of containing at least two nitrogen atoms and excludes aromatic ring systems.

Unless otherwise defined, the term "optionally substituted" as used herein means that a group may include one or more substituents that do not interfere with the binding activity of the compound of formula I. In some instances the substituent may be selected to improve binding. The group may be substituted with one or more substituents selected from halogens, $C_{1-6}$ alkyl, $C_{2-6}$ alkenyl, $C_{2-6}$ alkynyl, —(CH$_2$)$_p$C$_{3-7}$ cycloalkyl, —(CH$_2$)$_p$C$_{4-7}$ cycloalkenyl, —(CH$_2$)$_p$ aryl, —(CH$_2$)$_p$ heterocyclyl, —C$_6$H$_4$S(O)$_1$C$_{1-6}$ alkyl, —C(Ph)$_3$, —(CH$_2$)$_p$Z, —COZ, —CN, —OR, —O—(CH$_2$)$_{1-6}$—R, —O—(CH$_2$)$_{1-6}$—OR, —OCOR, —COR, —COOR, —OCONR'R", —NR'R", —NRCOR', —NRCONR'R", —NRC(S)NR'R", —NRSO$_2$R', —NRCOOR', —C(NR)NR'R", —CRNOR', —C(=NOH)NR'R", —CONR'R", —C(=NCN)—NR'R", —C(=NR)NR'R", —C(=NR')SR", —NR'C(=NCN)SR", —CONRSO$_2$R', —C(S)NR'R", —S(O)$_t$R, —SO$_2$NR'R", —SO$_2$NRCOR', —OS(O)$_2$R, —PO(OR)$_2$ and —NO$_2$; where p is 0-6, t is 0-2, Z is an N-linked amino acid selected from the group consisting of alanine, asparagine, aspartic acid, glutamic acid, glutamine, glycine, pipecolic acid, α-amino-butyric acid, α-amino-propanoic acid, and iminodiacetic acid, Z being linked through a nitrogen atom of said N-linked amino acid to the carbon atom, and each R, R' and R" is independently selected from H, $C_{1-6}$ alkyl, $C_{2-6}$ alkenyl, $C_{2-4}$ alkynyl, $C_{3-7}$ cycloalkyl, $C_{4-7}$ cycloalkenyl, aryl, heterocyclyl, $C_{1-6}$ alkylaryl and $C_{1-4}$ alkylheterocyclyl, wherein the alkyl, alkenyl, alkynyl, cycloalkyl, cycloalkenyl, aryl, heterocyclyl, $C_{1-6}$ alkylaryl or $C_{1-6}$ alkylheterocyclyl, may be optionally substituted with one to six of same or different selected from halogen, hydroxy, lower alkyl, lower alkoxy, —CO$_2$H, CF$_3$, CN, phenyl, NH$_2$ and —NO$_2$; or when R' and R" are attached to the same nitrogen atom, they may, together with the atom to which they are attached, form a 5 to 7 membered nitrogen containing heterocyclic ring.

When the optional substituent is or contains an alkyl, alkenyl, alkynyl, cycloalkyl, cycloalkenyl, aryl or heterocyclyl group, the group may itself be optionally substituted with one to six of the same or different halogen atoms, hydroxy, lower alkyl, lower alkoxy, halo-$C_{1-4}$ alkyl (including —$CF_3$), phenyl, benzyl, —CN, —C(O)—$C_{1-6}$ alkyl, mercapto, —$NH_2$, mono or di (lower alkyl)amino or —$NO_2$.

In relation to nitrogen containing heterocyclic rings, unless otherwise defined optionally substituted includes pyridinium salts and the N-oxide form of suitable ring nitrogens.

In relation to non-aromatic carbocyclic or heterocyclic compounds, unless otherwise defined such compounds may also be optionally substituted with one or two =O groups, instead of or in addition to the above described optional substituents.

Examples of optional substituents include halogens, $C_{1-4}$ alkyl, $C_{2-4}$ alkenyl, $C_{2-4}$ alkynyl, alkoxy, $C_{1-4}$ haloalkyl, —$CF_3$, —OH, phenyl, —$NH_2$, —$NHC_{1-4}$ alkyl, —$N(C_{1-4})_2$, —CN, mercapto, $C_{1-4}$ alkylcarbonyl and $C_{1-4}$ alkoxycarbonyl.

As used herein the term "$C_{1-12}$ alkyl" refers to straight chain or branched saturated hydrocarbon group having from 1 to 12 carbon atoms. Examples of such alkyl groups include methyl, ethyl, n-propyl, isopropyl, n-butyl, isobutyl, sec-butyl or ten-butyl. Similarly "$C_{1-6}$ alkyl" or "lower alkyl" refers to such groups having from 1 to 6 carbon atoms.

As used herein the term "$C_{3-7}$ cycloalkyl" refers to non-aromatic, saturated cyclic groups having from 3 to 7 carbon atoms. Examples include cyclopentyl and cyclohexyl.

As used herein the term "alkoxy" refers to a straight or branched alkyl group covalently bound via an O linkage and the terms "$C_{1-6}$ alkoxy" and "lower alkoxy" refer to such groups containing from one to six carbon atoms, such as methoxy, ethoxy, propoxy, isopropoxy, butoxy, t-butoxy and the like.

As used herein the term "$C_{2-12}$ alkenyl" refers to groups formed from $C_{2-12}$ straight chain or branched non-cyclic hydrocarbon containing one or more double bonds. Examples of $C_{2-12}$ alkenyl include allyl, 1-methylvinyl, butenyl, iso-butenyl, 1,3-butadienyl, 3-methyl-2-butenyl, 1,3-butadienyl, 1,4-pentadienyl, 1-pentenyl, 1-hexenyl, 3-hexenyl, 1,3-hexadienyl, 1,4-hexadienyl and 1,3,5-hexatrienyl.

As used herein the term "$C_{4-7}$ cycloalkenyl" refers to non aromatic carbocycles having 4 to 7 carbon atoms and having one or more double carbon bonds. Examples include cyclopentenyl, 1-methyl-cyclopentenyl, cyclohexenyl, 1,3-cyclopentadienyl, 1,3-cyclohexadienyl and 1,4-cyclohexadienyl.

As used herein the term "$C_{2-12}$ alkynyl" refers to $C_{2-12}$ straight or branched non-cyclic hydrocarbon containing one or more triple bonds, preferably one or two triple bonds. Examples include 2-propynyl and 2- or 3-butynyl.

The term "aryl $C_{1-12}$ alkyl" refers to carbocyclic aromatic rings or ring systems as previously described and substituted by a $C_{1-12}$ alkyl group, also as previously described. Likewise the terms "aryl $C_{2-12}$ alkenyl" and "aryl $C_{2-12}$ alkynyl" refer to carbocyclic aromatic rings or ring systems as previously described and substituted by a $C_{2-12}$ alkenyl or $C_{2-12}$ alkynyl group, as previously described.

The aryl group and the alkyl, alkenyl or alkynyl group may be optionally substituted. Preferably the aryl group is not optionally substituted.

Preferably the alkyl, alkenyl or alkynyl group is optionally substituted, and more preferably with a substituent selected from halogens, —CN, —NR'R'', —COR, —COOR, or —CONR'R''. Preferably R, R' and R'' are independently selected from hydrogen or lower alkyl.

As used herein the term "halo" or "halogen" refers to fluoro, chloro, bromo and iodo groups.

As used herein a "halo alkyl" group has one or more of the hydrogen atoms on an alkyl group replaced with halogens. An example includes —$CF_3$.

Particularly preferred compounds of the invention include those compounds where A is a bivalent link of 3 or 4 atoms selected from C, N, O and S. In that arrangement A and the atoms to which they are attached together form an aromatic ring having five or six ring atoms. When the linking atoms are all carbon, the ring formed is a carbocyclic aromatic ring or ring system. When the linking atoms include one or more of N, O or S then the ring formed is an aromatic heterocyclic ring. Examples include where the substructure is: —

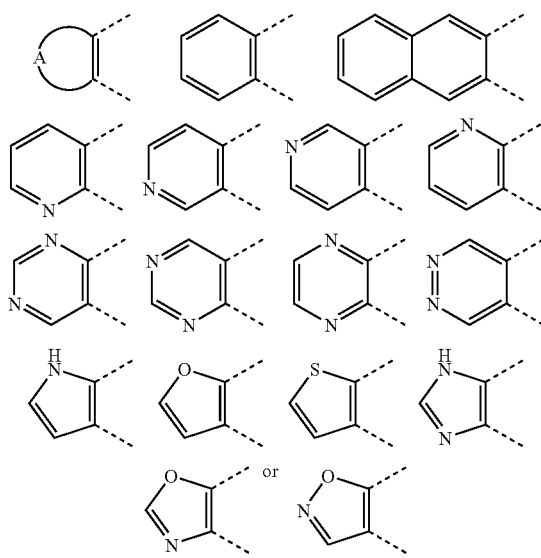

Preferably ring A is an optionally substituted aryl or heteroaryl ring, more preferably a phenyl, pyridyl, pyridazinyl, pyrimidinyl or pyrazinyl ring, and most preferably a phenyl or pyridyl ring. The optionally substituents include N-oxides of the ring nitrogen atoms.

The aromatic rings may be optionally substituted, preferably by no more than 3 substituents. Of the optional substituents, it is particular preferred to use 1 to 3 substituents selected from halo, lower alkyl, halogenated forms of lower alkyl, hydroxy, lower alkoxy, nitro, amino, loweralkylamino, carboxy, carboxamido, phenyl and benzyl. N-oxide forms of the nitrogen atoms of nitrogen containing rings are also preferred. When A is a pyridyl ring, the ring nitrogen may be in a N-oxide form, or the ring may be in the form of a pyridinium salt.

In respect of the heterocyclic ring formed by B—C, it will be understood that this ring can not be selected from all of the heterocyclic rings discussed earlier in relation to the meaning of the term due to the atoms to which B—C are attached. This ring is limited to monocyclic, non-aromatic heterocyclic rings that include at least two nitrogen atoms. The ring may include additional hetero atoms and may be partially unsaturated.

Particularly preferred are compounds in which B—C represents a bivalent link of 1 to 3 atoms. The link B—C together with the atoms to which it is attached forms a non-aromatic heterocyclic ring. Examples include where the substructure: is:

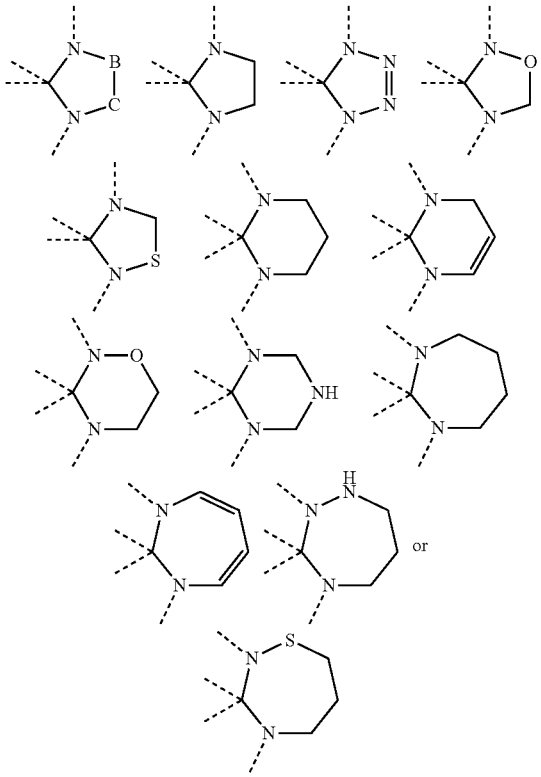

In a preferred form of the invention, B—C represents —CH$_2$—(CH$_2$)$_z$—, where z is 1-4, more preferably 1, 2 or 3, more preferably 1 or 2 and most preferably z is 1.

The atoms forming the link B—C may be optionally substituted, preferably by no more than 3 substituents. A broad range of substituents are possible and include halo, lower alkyl, hydroxy, lower alkoxy, phenyl and benzyl.

A preferred form of the invention includes those compounds where B—C represents —CH$_2$CH$_2$—.

Preferably X is oxygen or sulphur, more preferably X is oxygen.

In an embodiment of the invention fused ring A and the ring containing the bivalent link B—C are optionally substituted with one or two substituents independently selected from halogen and C$_{1-6}$ alkyl. Preferably fused ring A and the ring containing the bivalent link B—C are not substituted.

R$_1$ may be an optionally substituted aryl, alkyl or heterocyclyl. Preferably R$_1$ is an optionally substituted aryl or heterocyclyl group, more preferably a phenyl, thienyl, pyrrolyl or pyridyl ring. R$_1$ may also be a —C$_{1-6}$ alkylphenyl group. The rings of R$_1$ may b optional substituted with halo, hydroxy, nitro, —NR'R" (where R' and R" are independently selected from hydrogen, lower alkyl and —C(O)R, where R is C$_{1-6}$ alkyl, phenyl or heterocyclyl), C$_{1-12}$alkyl, phenyl and —O—R$_a$, where R$_a$ is —C$_{1-12}$alkyl, —C$_{3-7}$cycloalkyl, —C$_{1-12}$alkylC$_{3-7}$cycloalkyl, phenyl or —C$_{1-12}$alkylphenyl; and the C$_{1-12}$alkyl, phenyl or R$_a$ group may be optionally substituted with halo, —CN, —NR'R", —CO$_2$R or —CONR'R", where R, R' and R" are independently selected from hydrogen or lower alkyl. Preferably, the ring is phenyl and is optionally substituted in the para or 4-position.

R$_1$ may be -phenyl substituted with C$_{1-10}$ alkyl chain, where the alkyl chain is substituted with halo, —CN, —NR'R", —CO$_2$R or —CONR'R", where R, R' and R" are independently selected from hydrogen or lower alkyl. More preferably the alkyl chain is in the 4-position of the phenyl ring, and substituents are attached to the carbon at the free end of the alkyl group.

R$_1$ may be phenyl optionally substituted with a substituent selected from halo, —C$_{1-6}$alkyl, —C$_{1-6}$alkylhalo, —C$_{1-6}$alkylCN, —OC$_{1-6}$alkyl, —OC$_{1-6}$alkylhalo, —OC$_{1-6}$alkylCO$_2$NH$_2$, —OC$_{1-6}$alkylCN, —OC$_{1-6}$alkylC$_{3-7}$cycloalkyl, —OC$_{1-6}$alkylC$_6$H$_5$, —OC$_{1-6}$alkylOCH$_3$, —OC$_6$H$_5$, —OC$_6$H$_4$halo, —CF$_3$, —OCF$_3$, —NR'R" (where R' and R" are independently selected from hydrogen, —C(O)C$_{1-6}$alkyl, —C(O)C$_6$H$_5$, —C(O)CH=CHCO$_2$H, —C(O)C$_{1-6}$ alkylCO$_2$H, —C(O)C$_{1-6}$alkylCO$_2$CH$_3$, —C(O)C$_{1-6}$alkylC$_6$H$_5$, —C(O)C$_{1-6}$alkylC$_6$H$_4$CH$_3$, —C(O)C$_{1-6}$alkylC$_6$H$_4$OCH$_3$ and —C(O)C$_{1-6}$alkylC$_6$H$_4$halo), —CO$_2$H, —CO$_2$C$_{1-6}$alkyl, —NO$_2$, —OH, —C$_6$H$_5$, —C$_6$H$_4$C$_{1-6}$alkyl, —C$_6$H$_4$halo and —OC(O)C$_{1-6}$alkyl.

Preferably R$_1$ is halophenyl, most preferably 4-chlorophenyl.

Compounds where R$_2$ is hydrogen do not form part of the present invention. These compounds are useful as intermediates for the production of compounds of the invention in which R$_2$ is not hydrogen.

Preferably R$_2$ is not an unsubstituted —C$_{1-6}$alkyl or =substituted —C(O)—C$_{1-6}$alkyl.

When R$_2$ is —CH$_2$—R$_3$, it is preferred that R$_3$ is —(CH$_2$)$_m$ aryl or —(CH$_2$)$_m$ heterocyclyl, where m is 0 to 3. R$_3$ may be benzyl (m=1). The ring atoms may by optionally substituted with a broad range of substituents. Preferred substituents are selected from halo, lower alkyl, hydroxy, lower alkoxy and phenyl.

When R$_2$ is —C(Y)—R$_3$, it is preferred that Y is O. It is also preferred that R$_3$ is —(CH$_2$)$_m$ aryl or —(CH$_2$)$_m$ heteroaryl, where m is 0 to 3. It is particularly preferred for R$_3$ to be aryl or heteroaryl (m=0), and more preferably a 5 or 6 membered monocyclic heterocycle or 9 or 10 membered bicyclic heterocycle or an aryl group.

When R$_2$ is —C(Y)CH$_2$N(R$_4$)R$_3$ or —C(Y)CH$_2$SR$_3$, R$_3$ is preferably —(CH$_2$)$_m$ aryl or —(CH$_2$)$_m$ heterocyclyl where m is 0 to 3. The heterocycyl may itself be substituted with an oxo group, hydroxy or lower alkyl.

More preferably R$_3$ is phenyl, naphthyl, furyl, thienyl, pyrrolyl, H-pyrrolyl, pyrrolinyl, pyrrolidinyl, oxazolyl, oxadiazolyl, (including 1,2,3 and 1,2,4 oxadiazolyls) thiazolyl, isoxazolyl, furazanyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, triazinyl, 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl or pteridinyl.

The heterocyclic ring may be fused to a carbocyclic ring such as phenyl, naphthyl, indenyl, azulenyl, fluorenyl, and anthracenyl.

The aryl or heterocyclic may be optionally substituted with a broad range of substituents, and preferably with C$_{1-6}$ alkyl, C$_{1-6}$ alkoxy, C$_{2-6}$ alkenyl, C$_{2-6}$ alkynyl, halo, hydroxy, mercapto, trifluoromethyl, amino, nitro, cyano and mono or di($C_{1-6}$alkyl)amino. The substituents also include phenyl, benzyl and heterocyclyl.

Most preferably $R_3$ is selected from phenyl, furyl, thienyl, pyridyl, oxazolyl, thiazolyl, pyrazolyl, furazanyl, isoxazolyl, isothiazolyl, 1,3,4-triazolyl, 1,2,3-thiadiazolyl, 1,3,4-thiadiazolyl, pyridazinyl, pyrimidinyl, benzo[b]furanyl, benzo[b]thiophenyl and benzoisoxazolyl.

When $R_2$ is —$COR_3$, it is also preferred for $R_3$ to be -phenyl$C_{1-10}$alkyl, where the alkyl is substituted with halo, —CN, —NR'R", —$CO_2$R or —CONR'R", where R, R' and R" are independently selected from hydrogen or lower alkyl. More preferably the alkyl chain is in the 4-position of the phenyl ring, and substituents are attached to the carbon at the free end of the alkyl group.

When $R_2$ is —$CON(R_4)R_3$ it is preferred for $R_4$ to be hydrogen and $R_3$ to be —$(CH_2)_m$aryl or —$(CH_2)_m$heteroaryl. Preferably m is 0 to 2, more preferably 0 to 1. The aryl and heteroaryl ring atoms may be optionally substituted with a broad range of substituents. Preferred substituents include halo, lower alkyl, hydroxy, lower alkoxy and phenyl.

Another preferred embodiment of the invention are those compounds where $R_2$ is —$COR_3$ and fused ring A contains at least one ring nitrogen atom.

When the invention relates to compounds of formula I per se, it is preferred that when $R_1$ is unsubstituted phenyl, X is O, A together with the atoms to which it is attached forms an unsubstituted phenyl ring and B—C is —$CH_2CH_2$—, $R_2$ is not unsubstituted $C_{1-6}$ alkyl or —$C(O)C_{1-6}$alkyl.

It will be appreciated that compound of formula I and some derivatives thereof may have at least one asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms and all isomeric forms of the compounds being included in the present invention.

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts.

The term "pharmaceutically acceptable derivatives" includes pharmaceutically acceptable esters, prodrugs, solvates and hydrates, and pharmaceutically acceptable addition salts of the compounds or the derivatives. Pharmaceutically acceptable derivatives may include any pharmaceutically acceptable salt, solvate, hydrate or any other compound or prodrug which, upon administration to a subject, is capable of providing (directly or indirectly) a compound of formula I or an antivirally active metabolite or residue thereof.

The pharmaceutically acceptable salts include acid addition salts, base addition salts, salts of pharmaceutically acceptable esters and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicyclic, sulfamic, or tartaric acids. The counter ion of quarternary amines and pyridiniums include chloride, bromide, iodide, sulfate, phosphate, methansulfonate, citrate, acetate, malonate, fumarate, sulfamate, and tartate. The base addition salts include but are not limited to salts such as sodium, potassium, calcium, lithium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of the invention may be in crystalline form or as solvates (e.g. hydrates) and it is intended that both forms be within the scope of the present invention. The term "solvate" is a complex of variable stoichiometry formed by a solute (in this invention, a compound of the invention) and a solvent. Such solvents should not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine. Any compound that is a prodrug of a compound of the invention is within the scope and spirit of the invention. Conventional procedures for the preparation of suitable prodrugs according to the invention are described in text books, such as "Design of Prodrugs" Ed. H. Bundgaard, Elsevier, 1985.

The term "pharmaceutically acceptable ester" includes biologically acceptable esters of compound of the invention such as sulphonic, phosphonic and carboxylic acid derivatives.

Thus, in another aspect of the invention, there is provided a prodrug or pharmaceutically acceptable ester of a compound of formula I.

In another aspect of the invention, there is provided a pharmaceutical composition that comprises a therapeutically effective amount of one or more of the aforementioned anti-RSV compounds of formula I, including pharmaceutically derivatives thereof, and optionally a pharmaceutically acceptable carrier or diluent.

Unless otherwise specified the terms "treatment" or "treating", in the context of a method or use of the invention, includes both therapeutic and prophylactic treatments.

In further aspect of the present invention, there is provided the use of a compound of formula I, its salts or pharmaceutically acceptable derivatives thereof in the preparation of a medicament for the treatment (therapeutic or prophylactic) of RSV infections.

In another aspect of the invention, there is provided a method of treating RSV by the administration of a compound of formula I, including the administration of pharmaceutically acceptable salts, or derivatives such as prodrugs of formula I, or a composition containing at least one compound of formula I, to a patient in need to treatment.

In another aspect of the invention, there is provided a method for treating mammals infected with RSV, and in need thereof, which comprises administering to said mammal a therapeutically effective amount of one or more of the aforementioned compounds of formula I or pharmaceutically acceptable derivatives thereof.

In another aspect of the invention, there is provided a method for preventing the infection of mammals with RSV, which comprises administering to said mammal a therapeutically effective amount of one or more of the aforementioned compounds of formula I, or pharmaceutically acceptable derivatives thereof.

Although the invention has been described with reference to treating RSV, and in particularly human RSV, it will be appreciated that the invention may also be useful in the treatment of other viruses of the sub-family Pneumovirinae, more particularly, the genera Pneumovirus and Metapneumovirus, more particularly animal and human strains of RSV and metapneumovirus.

In a further form of the invention there is provided a process for the production of compounds of formula I. These compounds may be prepared using the procedure outlined in the following methods.

Scheme 1 depicts a general process for manufacture of compounds of formula III. Compounds of formula III are intermediates, similar to formula I but where $R_2$ is H.

Compounds of formula III may be prepared via appropriate starting materials of formula II. General methods for the preparation of 2-(aroyl)benzoic acids and 3-(aroyl)pyridine-2-carboxylic acids of formula II are described by Yamaguchi, M. et. al, J. Med. Chem. 1993, 36, 4052-4060 and Natsugari, H. et. al, J. Med. Chem. 1995, 38, 3106-3120.

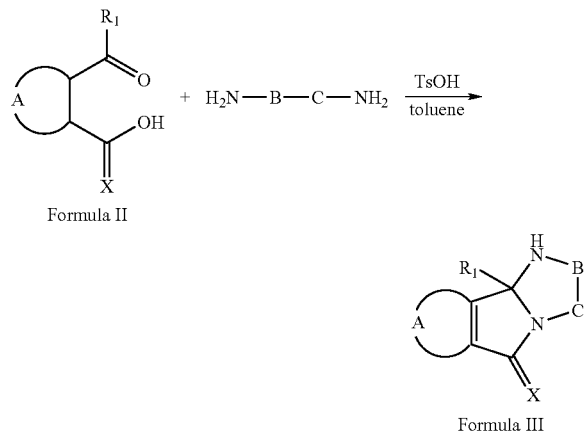

Scheme 1

Formula II

Formula III

In general, one equivalent of an appropriate keto-acid of formula II is reacted with approximately 3 equivalents of an appropriate diamine of the general formula H₂N—B—C—NH₂. The mixture is heated under reflux in an inert solvent, such as toluene or xylene, with a Dean-Stark apparatus for 3-10 h. A catalyst, such as an acid tosylate, can be used. After this time the reaction is allowed to cool and the product filtered and recrystallised from an appropriate solvent. If no precipitate forms the solvent is evaporated in-vacuo and the residue recrystallised or purified using flash chromatography or preparative HPLC.

Compounds of formula III can also be produced by the methods described in U.S. Pat. No. 4,058,529, Sulkowski, T. S., et. al, J. Org. Chem. 1967, 32, 2180-2184 and Houlihan, W. J., et. al, J. Med. Chem. 1975, 18, 182-185. Other (novel) compounds of formula I may be obtained by acylating compounds of formula III as described in Scheme 2.

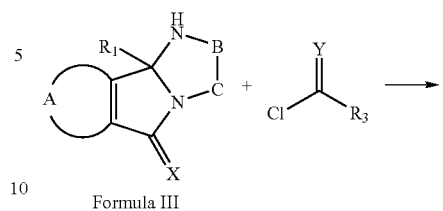

Scheme 2

Formula III

Formula I

In one method, two equivalents of diisopropylethylamine or triethylamine are added to one equivalent of a compound of formula III in THF at 0° C. An acid chloride, or other acylating agent, is added to the mixture and the reaction monitored by HPLC. When the reaction is complete the reaction is quenched with water and the product extracted into a suitable organic solvent and worked up according to standard methods. Similar acylation may also be carried out by reacting one equivalent of the compound of formula III with one equivalent of the appropriate acid chloride in xylene at 120° C. for 1-24 h. The reaction is then allowed to cool and the product isolated. Alternatively, compounds of formula III may be treated with approximately 2.2 equivalents of an appropriate acid chloride or anhydride in pyridine at approximately −5° C. The mixture is allowed to arm to room temperature and after stirring for 2-24 h the product is isolated by standard methods. Acylation may also be achieved by treating the appropriate compound of formula III with the appropriate carboxylic acid (3 equivalents), TFFH (3.3 equivalents) and DIEA (3.3 equivalents) in DMF and heating to 45° C. for approximately 14 days. After this time the product is isolated by standard methods.

N-alkylated and N-sulfonylated compounds of Formula I are best obtained using suitable N-substituted diamines. These may be prepared by known methods for example that described by Kruse L. I., et. al, J. Med. Chem. 1990, 33.781-789.

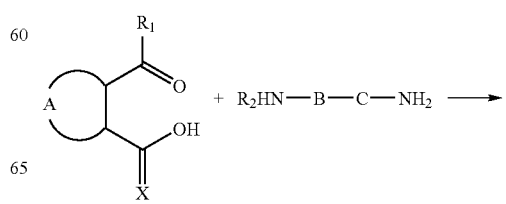

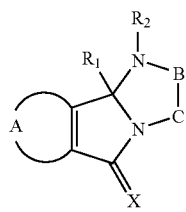

In which $R_2$ is —$CHR_3$ or —$S(O)_2R_5$, as earlier defined in the summary of the invention.

Hence, the appropriate keto-acid (2 equivalents) and N-substituted diamine (1 equivalent) in chlorobenzene, toluene or xylene are placed in a flask equipped with a stirrer and Dean-Stark water separator and heated at reflux until no further water is seen to separate (1-8 h). The solvent is then removed by distillation and the residue cooled. The residue can be purified using standard methods.

Compounds of Formula I where $R_2$ is a urea or thiourea are prepared using the following method.

One equivalent of the appropriate compound of formula III is reacted with one equivalent of the appropriate isocyanate or isothiocyanate in THF or xylene at a temperature ranging from 20-120° C. for 1-24 h. The reaction is then allowed to cool and the product filtered, washed and generally recrystallised from an appropriate solvent. If no precipitate is formed the product can be purified using standard chromatographic methods.

Other compounds of formula I can be prepared by the addition, removal or modification of existing substituents. This could be achieved by using standard techniques for functional group inter-conversion, well known in the industry such as those described in Comprehensive organic transformations: a guide to functional group preparations by Larock R C, New York, VCH Publishers, Inc. 1989.

Examples of functional group inter-conversions are: —C(O)NR'R" from —$CO_2CH_3$ by heating with or without catalytic metal cyanide, e.g. NaCN, and HNR'R" in $CH_3OH$; —OC(O)R from —OH with e.g., ClC(O)R in pyridine; —NC(S)NR'R" from —NHR with an alkylisothiocyanate or thiocyanic acid; —NRC(O)OR' from —NHR with alkyl chloroformate; —NRC(O)NR'R" from —NHR by treatment with an isocyanate, e.g. HN=C=O or RN=C=O; —NRC(O)R' from —NHR by treatment with ClC(O)R' in pyridine; —C(=NR)NR'R" from —C(NR'R')SR with $H_3NR^+OAc^-$ by heating in alcohol; —C(NR'R")SR from —C(S)NR'R" with R—I in an inert solvent, e.g. acetone; —C(S)NR'R" (where R' or R" is not hydrogen) from —$C(S)NH_2$ with HNR'R"; —C(=NCN)—NR'R" from —C(=NR'R")—SR with $NH_2CN$ by heating in anhydrous alcohol, alternatively from —C(=NH)—NR'R" by treatment with BrCN and NaOEt in EtOH; —NR—C(=NCN)SR from —NHR' by treatment with $(RS)_2C=NCN$; —$NR"SO_2R$ from —NHR' by treatment with $ClSO_2R$ by heating in pyridine; —NR'C(S)R from —NR'C(O)R by treatment with Lawesson's reagent [2,4-bis(4-methoxyphenyl)-1,3,2,4-dithiadiphosphetane-2,4-disulfide]; —$NRSO_2CF_3$ from —NHR with triflic anhydride and base, —$CH(NH_2)CHO$ from —$CH(NH_2)$ $C(O)OR'$ with Na(Hg) and HCl/EtOH; —$CH_2C(O)OH$ from —C(O)OH by treatment with $SOCl_2$ then $CH_2N_2$ then $H_2O/Ag_2O$; —C(O)OH from —$CH_2C(O)OCH_3$ by treatment with PhMgX/HX then acetic anhydride then $CrO_3$; R—OC(O)R' from RC(O)R' by R"$CO_3H$; —$CCH_2OH$ from —C(O)R' with Na/R'OH; —$CHCH_2$ from —$CH_2CH_2OH$ by the Chugaev reaction; —$NH_2$ from —C(O)OH by the Curtius reaction; —$NH_2$ from —C(O)NHOH with TsCl/base then $H_2O$; —CHC(O)CHR from —CHCHOHCHR by using the Dess-Martin Periodinane regent or $CrO_3/aqH_2SO_4$/acetone; —$C_6H_5CHO$ from —$C_6H_5CH_3$ with $CrO_2Cl_2$; —CHO from —CN with $SnCl_2$/HCl; —CN from —C(O)NHR with $PCl_5$; —$CH_2R$ from —C(O)R with $N_2H_4$/KOH.

During the reactions a number of the moieties may need to be protected. Suitable protecting groups are well known in industry and have been described in many references such as Protecting Groups in Organic Synthesis, Greene T W, Wiley-Interscience, New York, 1981.

The abbreviations that may be used herein, including in Schemes I-II, and experimental section are as follows unless indicated otherwise:

DCM: dichloromethane
DIEA: diisopropylethylamine
DMF: dimethylformamide
Et: ethyl
EtOAc: ethyl acetate
Me: methyl
MeOH: methyl alcohol
MS: mass spectrometry
NMR: nuclear magnetic resonance
Ph: phenyl
HPLC: high performance liquid chromatography
TEA: triethylamine
TFA: Trifluoroacetic acid
TFFH: Fluoro-N,N,N",N"-tetramethylformamidinium hexafluorophosphate
THF: tetrahydrofuran
TsCl: Tosyl chloride
TsOH: Toluenesulphonic acid The invention also pertains to therapeutic compositions containing at least one compound of formula I including pharmaceutical acceptable salts or prodrugs.

The compositions may further contain one or more other compounds having anti-viral activity in respect of RSV, such as Virazole, or other agents such as RespiGam or Synagis.

The compositions may further contain or be administered in combination with other drugs to treat symptoms of the disease, such as for example anti-inflammatory medicaments.

The term "composition" is intended to include the formulation of an active ingredient with conventional carriers and excipients, and also with encapsulating materials as the carrier, to give a capsule in which the active ingredient (with or without other carriers) is surrounded by the encapsulation carrier.

As will be readily appreciated by those skilled in the art, the route of administration and the nature of the pharmaceutically acceptable carrier will depend on the nature of the condition and the animal to be treated. It is believed that the choice of a particular carrier or delivery system, and route of administration could be readily determined by a person skilled in the art. In the preparation of any formulation containing the compounds care should be taken to ensure that the activity of the compound is not destroyed in the process and that the compound is able to reach its site of action without being destroyed. In some circumstances it may be necessary to protect the compound by means known in the art, such as, for example, micro encapsulation. Similarly the route of administration chosen should be such that the compound reaches its site of action.

The pharmaceutical compositions or formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

It is envisaged that the compositions should be provided in a form suitable for oral or nasal administration or by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compositions according to the present invention may thus be formulated for parenteral administration (e.g. by injection, for example bolus injection or continuous infusion) and may be presented in unit dose form in ampoules, prefilled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, eg. sterile, pyrogen-free water, before use.

Pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

Those skilled in the art may readily determine appropriate formulations for the compounds of the present invention using conventional approaches. Identification of preferred pH ranges and suitable excipients, for example antioxidants, is routine in the art (see for example Cleland et al, 1993). Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

The solvent or dispersion medium for the injectable solution or dispersion may contain any of the conventional solvent or carrier systems for the compounds, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolality, for example, sugars or sodium chloride. Preferably, the formulation for injection will be isotonic with blood. Prolonged absorption of the injectable compositions can be brought about by the use in the compositions of agents delaying absorption, for example, aluminium monostearate and gelatin. Pharmaceutical forms suitable for injectable use may be delivered by any appropriate route including intravenous, intramuscular, intracerebral, intrathecal, epidural injection or infusion.

Sterile injectable solutions are prepared by incorporating the active compounds in the required amount in the appropriate solvent with various other ingredients such as these enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations preferably contain at least 1% by weight of active compound. The percentage of the compositions and preparations may, of course, be varied and may conveniently be between about 5 to about 80% of the weight of the unit. The amount of active compound in therapeutically useful compositions should be sufficient that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations, including those that allow specific delivery of the active peptide to specific regions of the gut.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except in so far as any conventional media or agent is incompatible with the active ingredient, use thereof in the therapeutic compositions is contemplated. Supplementary active ingredients can also be incorporated into the compositions.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The invention also includes the compounds in the absence of carrier where the compounds are in unit dosage form.

The amount of compound of formula I administered may be in the range from about 10 mg to 2000 mg per day, depending on the activity of the compound and the disease to be treated.

Liquids or powders for intranasal administration, tablets or capsules for oral administration and liquids for intravenous administration are the preferred compositions.

Experimental Data $^1$H NMR spectra were recorded on either a Bruker Avance DRX 400, AC 200 or AM 300 spectrometer. Spectra were recorded in CDCl$_3$, d$_6$-acetone, CD$_3$OD or d$_6$-DMSO using the residual solvent peak as a reference. Chemical shifts are reported on the δ scale in parts per million (ppm) using the following conventions to assign the multiplicity: s (singlet), d (doublet), t (triplet), q (quartet) m (multiples) and prefixed b (broad). Mass spectra (ESI) were recorded on either a Micromass Platform QMS or Finnigan LCQ Advantage spectrometer. Flash chromatography was performed on 40-63 μm silica gel 60 (Merck No. 9385). Analytical HPLC was carried out using a Waters 600 Pump, Waters 717 Autosampler and a Waters 490E UV detector. Preparative HPLC was carried out using a Gilson 322 pump with a Gilson 215 liquid handler and a HP1100 PDA detector. Both HPLC systems employed Phenomonex C8(2) columns using either acetonitrile or acetonitrile containing 0.06% TFA in water or water containing 0.1% TFA.

Method A

One equivalent of an appropriate keto-acid of formula II, is reacted with approximately 3 equivalents of an appropriate diamine of the general formula H$_2$N—B—C—NH$_2$. The mixture is heated under reflux in an inert solvent, such as toluene or xylene, with a Dean-Stark apparatus for 3-10 h. A catalyst, such as an acid tosylate, can be used. After this time the reaction is allowed to cool and the product filtered and recrystallised from an appropriate solvent. If no precipitate forms the solvent is evaporated in-vacuo and the residue recrystallised or purified using flash chromatography or preparative HPLC.

Compound 1

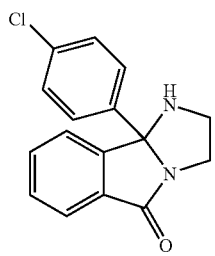 [SMILES: O=C1c2ccccc2C2(c3ccc(Cl)cc3)NCCN12]

Compound 1 was prepared using Method A employing 2-(4-chlorobenzoyl)benzoic acid and ethylene diamine.

$^1$H NMR (300 MHz, CDCl$_3$) δ 2.05 (bs, 1H), 3.11-3.26 (m, 2H), 3.61-3.68 (m, 1H), 3.76-3.84 (m, 1H), 7.22-7.26 (m, 1H), 7.30 (d, J=8.9 Hz, 2H), 7.42-7.48 (m, 2H), 7.62 (d, J=8.8 Hz, 2H), 7.74-7.80 (m, 1H).

MS m/z 285 ([M+H$^+$]

Compound 2

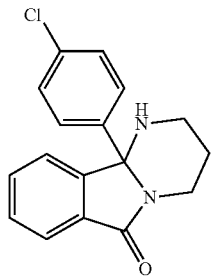 [SMILES: O=C1c2ccccc2C2(c3ccc(Cl)cc3)NCCCN12]

Compound 2 was prepared using Method A from 2-(4-chlorobenzoyl)benzoic acid and 1,3-diaminopropane.

$^1$H NMR (300 MHz, CDCl$_3$) δ 1.48-1.62 (m, 2H), 2.83-2.96 (m, 1H), 2.97-3.13 (m, 2H), 4.47-4.60 (m, 1H), 7.22-7.29 (m, 1H), 7.31-7.37 (m, 2H), 7.38-7.47 (m, 2H), 7.48-7.56 (m, 2H), 7.82-7.89 (m, 1H).

MS m/z ([M+H$^+$] 299

Compound 7

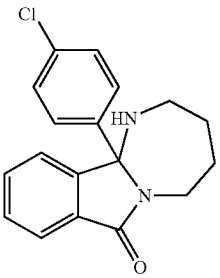 [SMILES: O=C1c2ccccc2C2(c3ccc(Cl)cc3)NCCCCN12]

Compound 7 was prepared using Method A from 2-(4-chlorobenzoyl)benzoic acid and 1,4-diaminobutane.

$^1$H NMR (300 MHz, CDCl$_3$) δ 1.13-1.32 (m, 2H), 1.33-1.57 (m, 2H), 2.15-2.44 (m, 2H), 2.73-2.90 (m, 1H), 3.32-

3.49 (m, 1H), 7.10-7.20 (m, 1H), 7.21-7.34 (m, 4H), 7.35-7.49 (m, 2H), 7.60-7.71 (m, 1H).

MS m/z ([M+H$^+$] 313

The methods for forming compounds of formula III are based on those described in U.S. Pat. No. 4,058,529, Sulkowski, T. S., et. al, J. Org. Chem. 1967, 32, 2180-2184 and Houlihan, W. J., et. al, J. Med. Chem. 1975, 18, 182-185.

Method B

Two equivalents of diisopropylethylamine or triethylamine are added to one equivalent of compound of formula III in THF at 0° C. An acid chloride, or other acylating agent, is added to the mixture and the reaction monitored by HPLC. When the reaction is complete the reaction is quenched with water and the product extracted into EtOAc. The EtOAc is subsequently washed with a 1:1 solution of sat. NH$_4$Cl$_{(aq)}$:water, 1:1 sat. Na$_2$CO$_{3(aq)}$:water and sat. Na$_2$CO$_{3(aq)}$. The EtOAc was dried (Na$_2$SO$_4$), the solvent evaporated in vacuo and the residue either crystallised or purified by flash chromatography using EtOAc/hexanes or by preparative HPLC.

Method C

One equivalent of the appropriate compound of formula III is reacted with one equivalent of the appropriate acid chloride in xylene at 120° C. for 1-24 h. The reaction is then allowed to cool and the product filtered and recrystallised from an appropriate solvent. If no precipitate is formed the reaction is purified using flash chromatography or preparative HPLC.

Method D

N-alkylated diamines may be prepared according to the procedure outlined in Kruse L. I., et. al, J. Med. Chem. 1990, 33, 781-789.

Appropriate keto-acid (2 equivalents) and N-substituted diamine(1 equivalent) in chlorobenzene, toluene or xylene are placed in a flask equipped with a stirrer and Dean-Stark water separator. The mixture is refluxed until no further water is seen to separate (1-8 h) after which time the solvent is then distilled off and the residue cooled. The residue is purified using flash chromatography or preparative HPLC.

Method E

One equivalent of the appropriate compound of formula III is reacted with one equivalent of the appropriate isocyanate or isothiocyanate in THF or xylene at a temperature ranging from 20-120° C. for 1-24 h. The reaction is then allowed to cool and the product filtered, washed and recrystallised from an appropriate solvent. If no precipitate was formed the reaction was purified using flash chromatography or preparative HPLC.

Compound 12

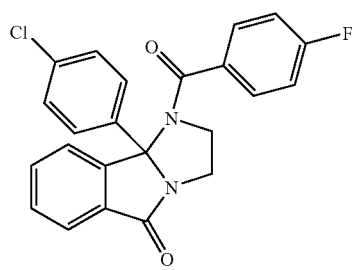 [SMILES: O=C(c1ccc(F)cc1)N1CCN2C(=O)c3ccccc3C12c1ccc(Cl)cc1]

Compound 12 was prepared using Method C using Compound 1 and 4-fluorobenzoyl chloride.

$^1$H NMR (300 MHz, CDCl$_3$) δ 3.22-3.34 (m, 1H), 3.73-3.82 (m, 1H), 3.91-4.03 (m, 1H), 4.28-4.36 (m, 1H), 7.05-7.13 (m, 2H), 7.17 (d, J=7.8 Hz, 2H), 7.33 (d, J=7.8 Hz, 2H), 7.43-7.52 (m, 2H), 7.54-7.65 (m, 2H), 7.84-7.90 (m, 1H), 8.00-8.06 (m, 1H).

MS m/z 407 ([M+H$^+$]

Compound 13

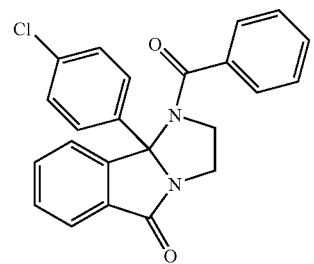 [SMILES: O=C(c1ccccc1)N1CCN2C(=O)c3ccccc3C12c1ccc(Cl)cc1]

Compound 13 was prepared using Method C using Compound 1 and benzoyl chloride. $^1$H NMR (300 MHz, CDCl$_3$) δ 3.21-3.31 (m, 1H), 3.72-3.79 (m, 1H), 3.91-4.00 (m, 1H), 4.26-4.33 (m, 1H), 7.20 (d, J=8.8 Hz, 2H), 7.34 (d, J=8.8 Hz, 2H), 7.38-7.48 (m, 5H), 7.56-7.61 (m, 2H), 7.85-7.88 (m, 1H), 8.04-8.07 (m, 1H).

MS m/z 389 ([M+H$^+$]

Compound 23

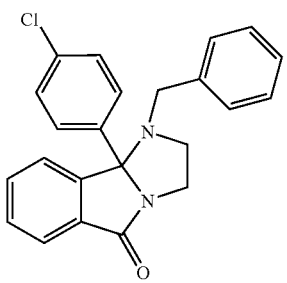 [SMILES: O=C1c2ccccc2C2(c3ccc(Cl)cc3)N(Cc3ccccc3)CCN12]

Compound 23 was prepared using Method D from 2-(4-chlorobenzoyl)benzoic acid and N-benzyl ethylenediamine.

$^1$H NMR (300 MHz, CDCl$_3$) δ 2.97 (d, J$_{AB}$ 13 Hz, 1H), 3.07-3.32 (m, 3H), 3.42 (d, J$_{AB}$ 13 Hz, 1H), 3.83-3.96 (m, 1H), 7.04-7.09 (m, 1H), 7.17-7.38 (m, 8H), 7.39-7.46 (m, 1H), 7.66-7.73 (m, 2H), 7.81-7.86 (m, 1H).

MS m/z ([M+H$^+$] 375

Compound 24

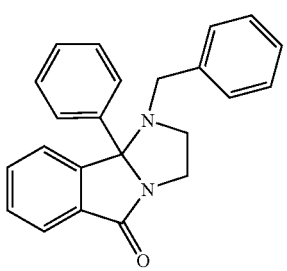 [SMILES: O=C1c2ccccc2C2(c3ccccc3)N(Cc3ccccc3)CCN12]

Compound 24 was prepared using Method D from 2-benzoylbenzoic acid and N-benzyl ethylenediamine.

$^1$H NMR (300 MHz, CDCl$_3$) δ 2.99 (d, J$_{AB}$ 13 Hz, 1H), 3.10-3.29 (m, 3H), 3.44 (d, J$_{AB}$ 13 Hz, 1H), 3.84-3.99 (m, 1H), 7.07-7.13 (m, 1H), 7.18-7.44 (m, 10H), 7.73-7.81 (m, 2H), 7.82-7.87 (m, 1H).

MS m/z ([M+H$^+$] 341

Compound 25

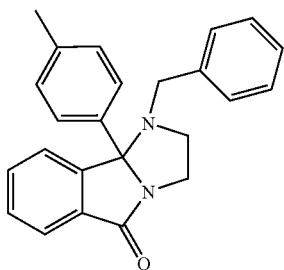 [SMILES: Cc1ccc(C23c4ccccc4C(=O)N2CCN3Cc2ccccc2)cc1]

Compound 25 was prepared using Method D from 2-(4-toluoyl)benzoic acid and N-benzyl ethylenediamine.

$^1$H NMR (300 MHz, CDCl$_3$) δ 2.36 (s, 3H), 3.00 (d, J$_{AB}$ 13 Hz, 1H), 3.11-3.29 (m, 3H), 3.45 (d, J$_{AB}$ 13 Hz, 1H), 3.86-3.98 (m, 1H), 7.08-7.14 (m, 1H), 7.15-7.21 (m, 2H), 7.22-7.44 (m, 7H), 7.63-7.69 (m, 2H), 7.81-7.86 (m, 1H).

MS m/z ([M+H$^+$] 355

Compound 106

Compound 106 was prepared using Method A employing 3-bromo-(4-chlorobenzoyl)benzoic acid and ethylene diamine.

1H NMR (300 MHz, CDCl$_3$): δ 3.12-3.25 (m, 2H), 3.64-3.71 (m, 1H), 3.76-3.83 (m, 1H), 7.13, (dd, J 8.1, 0.6 Hz, 1H), 7.33 (d, J 8.7 Hz, 2H), 7.57-7.61 (m, 3H), 7.91 (dd, J 1.8, 0.6 Hz, 1H).

MS m/z ([M+H]+) 365

Compound 107

Compound 107 was prepared using Method A employing 4-bromo-(4-chlorobenzoyl)benzoic acid and ethylene diamine.

1H NMR (300 MHz, CDCl$_3$): δ 3.11-3.24 (m, 2H), 3.69-3.63 (m, 1H), 3.76-3.82 (m, 1H), 7.34, (d, J 8.7 Hz, 1H), 7.39 (dd, J 1.5, 0.6 Hz, 7.59-7.66 (m, 4H).

MS m/z ([M+H]+) 365

Method F

Two equivalents of boronic acid or ester, five equivalents of Na$_2$CO$_3$ and palladium on charcoal (catalytic) or 0.1 equivalents of [PdCl$_2$(dppf)] (dichloro[1,1'-bis (diphenylphosphino)ferrocene]palladium (II) dichloromethane adduct) are added to the appropriate bromo-substituted compound of formula III in DME/H2O (93:7). The reaction is heated to 50° C. for 1-4-h. The reaction is then cooled, filtered and evaporated in vacuo to give a solid or oily residue. The residue is then either recrystallised or purified by flash chromatography using EtOAc/hexanes or by preparative HPLC.

Method G

Three equivalents of boronic acid or ester, six equivalents of K$_2$CO$_3$ and 0.3 equivalents of tetrakis(tripheynylphosphine)palladium are added to the appropriate bromo-substituted compound of formula III in toluene. The reaction is heated to 100° C. for 1-24 h. The reaction is then quenched with CH$_2$Cl$_2$ and washed with water. The CH$_2$Cl$_2$ layer was dried (Na$_2$SO$_4$) and evaporated in vacuo to give a solid or oily residue. The residue is then either recrystallised or purified by flash chromatography using EtOAc/hexanes or by preparative HPLC.

Method H

The acid chloride or anhydride or isocyanate or isothiocyanate (2.2 eq) is added directly for liquids or as a solution in pyridine (~1M) for solids to a solution of the appropriate compound of formula III (0.1 mmol) in pyridine (500 µL) at −5° C. The reaction is stirred and allowed to warm to room temperature for between 2-24 h after which time the starting material has been consumed. The reaction is subsequently diluted with water and extracted with CH$_2$Cl$_2$ (3×). The combined CH$_2$Cl$_2$ extracts are washed with 1N NaOH (3×) and 10% HCl (3×). In the case of basic products the acid wash is omitted and in the case of acidic products the basic wash is omitted. For neutral or basic products the crude purity is improved markedly by stirring the combined CH$_2$Cl$_2$ extract in the presence of a carbonate resin (MP-Carbonate ~3 eq) for 0.5-12 h. The CH$_2$Cl$_2$ extracts are dried (MgSO$_4$) and the solvent evaporated in-vacuo. The crude products are subsequently purified by flash chromatography using a EtOAc/Hexane solvent system.

Compound 120

Compound 120 was prepared using Method F employing compound 107 and 4-tolylboronic acid.

1H NMR (300 MHz, CDCl$_3$): δ 3.19-3.26 (m, 2H), 3.65-3.72 (m, 1H), 3.86-3.89 (m, 1H), 7.23, (d, J 8.1 Hz, 2H), 7.34 (d, J 8.7 Hz, 2H), 7.39-7.45 (m, 3H), 7.65-7.71 (m, 3H), 7.82 (dd, J 8.1, 0.6 Hz, 4H).

MS m/z ([M+H]+) 375

Compound 132

Compound 132 was prepared using Method G employing compound 107 and n-butylboronic acid.

1H NMR (300 MHz, CDCl$_3$): δ 0.89 (1, J 7.5 Hz, 3H), 1.23-1.37 (m, 3H), 1.48-1.56 (m, 2H), 2.59 (t, J 7.8 Hz, 2H), 3.12-3.26 (m, 2H), 3.62-3.69 (m, 1H), 3.83-3.78 (m, 1H), 7.26-7.35 (m, 3H), 7.62-7.69 (m, 3H).

MS m/z ([M+H]+) 341

Method I

A mixture of an appropriate carboxylic acid (3 eq) and TFFH (3.3 eq) was suspended in anhydrous DMF (0.25M) and DMA (3.3 eq) under nitrogen. The mixture was heated at 45° C. for 30 min. This solution was added to the appropriate compound of Formula III (1 eq) under nitrogen and heated at 45° C. for 14 days. The reaction mixture was transferred to a 10 mL tube and diluted with CH$_2$Cl$_2$ (2 mL). The organic phase was washed with 10% citric acid (2 mL), sat. NaHCO$_3$ (aq) (2 mL) and evaporated to dryness. The residue was purified by flash chromatography over silica, using 0.4% methanol/CH$_2$Cl$_2$ as eluent, to isolate the desired product.

Method J

This method is an adaptation of the method described by Copéret, C. et al., J. Org. Chem., 1998, 63, 1740-1741.30% Hydrogen peroxide (10 eq) was added to a solution of either an appropriate compound of Formula I or Formula III (1 eq) and trioxorhenium 2.5 mol % in CH$_2$Cl$_2$ (4× volume of hydrogen peroxide solution) at rt. The mixture was stirred overnight after which time the mixture was diluted with water and stirred for a further 30 mins. After this time the CH$_2$Cl$_2$ was separated and the aqueous layer extracted further with CH$_2$Cl$_2$ (2×). The combined extracts were dried and the solvent evaporated in-vacuo to yield the desired product which was purified by crystallisation or chromatography as required.

Method K

An appropriate substrate of Formula I, wherein R$_2$=6-fluoronicotinoyl or 6-chloronicotinoyl, was produced using Method H. To this substrate was added an excess of an appropriate amine. In a suitable solvent, such as THF or ethanol, the mixture was heated in a sealed vessel to approximately 150° C. for 1-5 h (or 60° C. for 72 h in the case where the nucleophile was hydrazine). After this time the solvent was evaporated and the residue purified using flash chromatography or preparative HPLC.

Method L

A suitable phenolic compound of formula III was acylated according to Method H. Ester hydrolysis was then effected by dissolving the product in a minimal volume of methanol and treating with an excess of 1M NaOH (aq) at ambient temperature. The reaction mixture was then acidified, extracted with dichloromethane and purified by flash chromatography to yield a phenolic compound of formula I.

If desired, conversion of this phenol to a phenyl ether was then performed using standard techniques known in the industry such as those described in Vogel's Textbook of Practical Organic Chemistry by B. S. Furniss et al., Harlow, Longman Scientific & Technical, 1989 or Mitsunobu, O. Synthesis 1981, 1. The crude products were subsequently purified using flash chromatography or preparative HPLC.

Compound 239

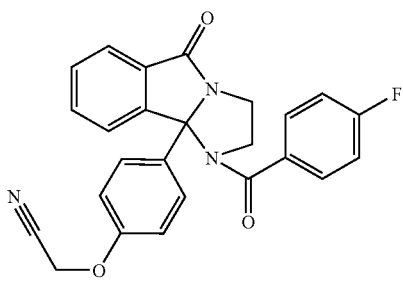 [SMILES: N#CCOc1ccc(C23c4ccccc4C(=O)N2CCN3C(=O)c2ccc(F)cc2)cc1]

Compound 239 was prepared from 9b-(4-hydroxyphenyl)-1,2,3,9b-tetrahydroimidazo[2,1-a]isoindol-5-one using Method L. The tetrahydroimidazoisoindolone was bis-acylated with 4-fluorobenzoyl chloride according to Method H and the resulting phenolic ester function was converted to a phenol by basic hydrolysis. The product was then treated with chloroacetonitrile and $K_2CO_3$ in acetone and heated to reflux for 30 h to yield phenyl ether compound 239.

$^1$H NMR (300 MHz, $d_6$-acetone) δ 3.28-3.38 (m, 1H), 3.91-3.97 (m, 1H), 4.09-4.27 (m, 2H), 5.12 (s, 2H), 7.08 (d, J 9.0 Hz, 2H), 7.17-7.26 (m, 2H), 7.30 (d, J 9.0 Hz, 2H), 7.61-7.71 (m, 4H), 7.79-7.82 (m, 1H), 8.05-8.08 (m, 1H).

Method M

This method involves nucleophilic displacement of $R_2$ when it represents 2-haloethanoyl. A solution or suspension of an appropriate compound of Formula I (R2=COCH2Br) (1 eq) and an appropriate amine (3 eq) were allow to stand at room temperature for 3 days. The mixture was allowed to evaporate to dryness, the residue lyophilised from 30% acetonitrile/water and the resultant crude product purified by preparative HPLC.

Method N

This method was used to prepare compound 153.

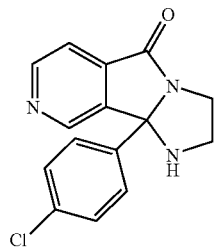 [SMILES: O=C1c2ccncc2C2(c3ccc(Cl)cc3)NCCN12]

Aluminium chloride (2.88 mol) was added to a stirred suspension of 3,4-pyridine anhydride (1.31 mol) in chlorobenzene (1.21) at RT to give an orange suspension and heated to 110° C. for 5 h. The mixture was cooled and carefully hydrolysed with water (21), heated to reflux for 1 h, filtered when hot and dried to give a brown solid. The solid was suspended in water (3.51) and basified with 10% NaOH solution (350 ml). The resulting solution was filtered, acidified to pH=3.1 with 2N HCl. The precipitate formed was filtered and refluxed with ethanol (21) to give a white solid (67 g). This material was dissolved in 10% NaOH (400 ml), acidified to pH 6.3 with 2N HCl and filtered to yield 3-(4-Chloro-benzoyl)-isonicotinic acid (53 g) as a white solid.

$^1$H-NMR (400 MHz, DMSO-$d_6$) δ 7.59 (d, J 8.6 Hz, 2H), 7.68 (d, J 8.6 Hz, 2H), 7.88 (dd, J 0.7, 5.0 Hz, 1H), 8.74 (d, J 0.7 Hz, 1H), 8.93 (d, J 5.0 Hz, 1H), 13.9 (bs, 1H) ppm.

3-(4-Chloro-benzoyl)-isonicotinic acid (53 g) and ethylene diamine (67.7 ml) in xylenes (1.81) were refluxed for 4 h. The solution was filtered when hot and the filtrate evaporated under reduced pressure to give a yellow solid (58 g). This material was recrystallised from ethanol to give Compound 153 as a white solid (46.4 g).

$^1$H-NMR (400 MHz, CDCl$_3$) δ 2.12 (bs, 1H, NH), 3.19 (m, 1H), 3.21 (m, 1H), 3.71 (m, 1H), 3.83 (m, 1H), 7.36 (d, J 8.8 Hz, 2H), 7.63 (d, J 8.8 Hz, 2H), 7.66 (dd, J 1.1, 4.9 Hz, 1H), 8.64 (d, J 1.1 Hz, 1H), 8.79 (d, J 4.9 Hz, 1H) ppm. MS m/z ([M+H]) 286

The above described methods were used to make the compounds described in tables 1 to 3 below. All compounds depicted in the tables were obtained. The tables set out a compound reference number, structure, observed mass (not calculated) and the method used to make the compound (based on correspondingly varied starting materials). The observed mass for the two compounds marked with * has not been included.

TABLE 1

Compounds of Formula III (Intermediates).

| No | Structure | m/z M + H$^+$ | Mtd |
|---|---|---|---|
| 1 | 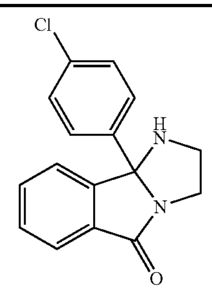 | 285 | A |
| 2 | 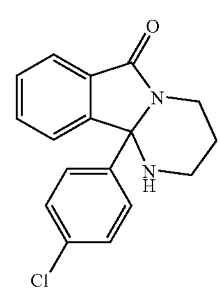 [SMILES: O=C1c2ccccc2C2(c3ccc(Cl)cc3)NCCCN12] | 299 | A |

TABLE 1-continued

Compounds of Formula III (Intermediates).

| No | Structure | m/z M + H+ | Mtd |
|---|---|---|---|
| 3 | 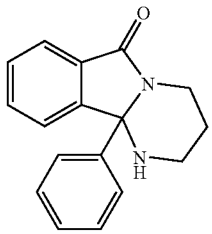 [SMILES: O=C1c2ccccc2C2(c3ccccc3)NCCCN12] | 265 | A |
| 4 | 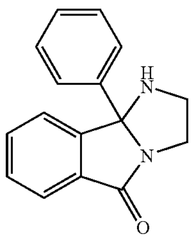 [SMILES: O=C1c2ccccc2C2(c3ccccc3)NCCN12] | 251 | A |
| 5 | 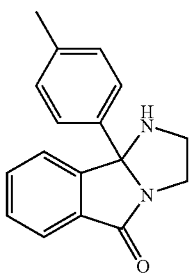 [SMILES: Cc1ccc(C23NCCN2C(=O)c2ccccc23)cc1] | 265 | A |
| 6 | 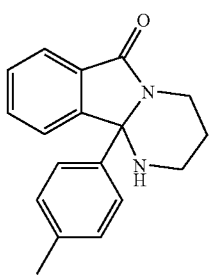 [SMILES: Cc1ccc(C23NCCCN2C(=O)c2ccccc23)cc1] | 279 | A |
| 7 | | 313 | A |
| 8 | 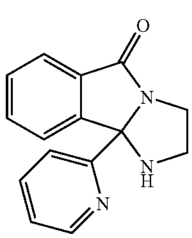 [SMILES: O=C1c2ccccc2C2(c3ccccn3)NCCN12] | 252 | A |
| 9 | | 286 | A |
| 10 | | 286 | A |
| 11 | | 252 | A |
| 96 | | 331 | A |
| 7 | | 331 | A |
| 100 | | 257 | A |

TABLE 1-continued

Compounds of Formula III (Intermediates).

| No | Structure | m/z M + H+ | Mtd |
|---|---|---|---|
| 102 | 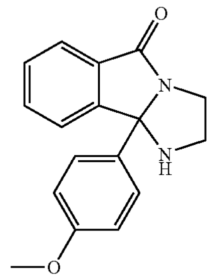 [SMILES: COc1ccc(C23NCCN2C(=O)c2ccccc23)cc1] | 281 | A |
| 103 | 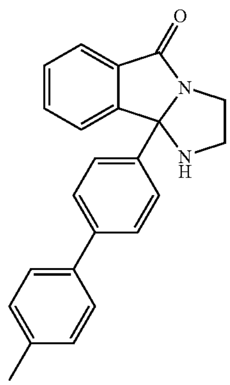 [SMILES: Cc1ccc(-c2ccc(C34NCCN3C(=O)c3ccccc34)cc2)cc1] | 341 | F |
| 106 | 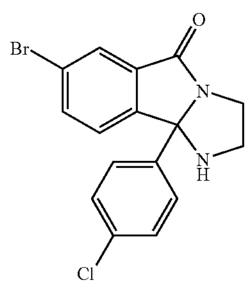 [SMILES: O=C1c2cc(Br)ccc2C2(c3ccc(Cl)cc3)NCCN12] | 365 | A |
| 107 | 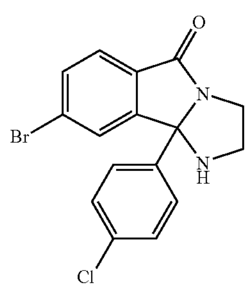 [SMILES: O=C1c2ccc(Br)cc2C2(c3ccc(Cl)cc3)NCCN12] | 365 | A |
| 110 | 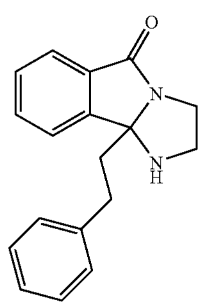 [SMILES: O=C1c2ccccc2C2(CCc3ccccc3)NCCN12] | 279 | A |
| 111 | | 296 | A |
| 112 | | 266 | A |
| 115 | | 308 | H |
| 116 | | 388 | H |

TABLE 1-continued

Compounds of Formula III (Intermediates).

| No | Structure | m/z M + H⁺ | Mtd |
|---|---|---|---|
| 120 | 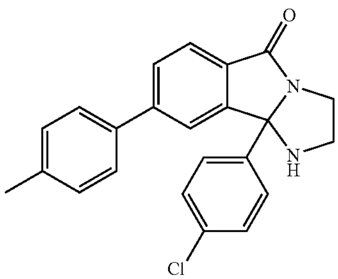 [SMILES: Cc1ccc(-c2ccc3c(c2)C2(c4ccc(Cl)cc4)NCCN2C3=O)cc1] | 375 | F |
| 121 | 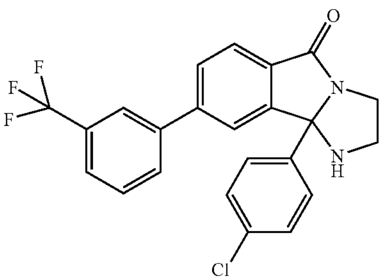 [SMILES: O=C1c2ccc(-c3cccc(C(F)(F)F)c3)cc2C2(c3ccc(Cl)cc3)NCCN12] | 429 | F |
| 122 | 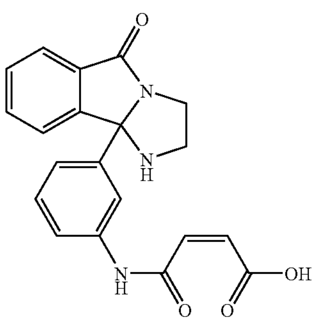 [SMILES: O=C(O)/C=C\C(=O)Nc1cccc(C23NCCN2C(=O)c2ccccc23)c1] | 364 | H |
| 126 | 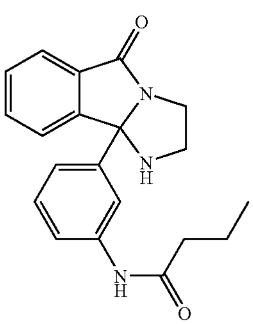 [SMILES: CCCC(=O)Nc1cccc(C23NCCN2C(=O)c2ccccc23)c1] | 336 | H |
| 127 | 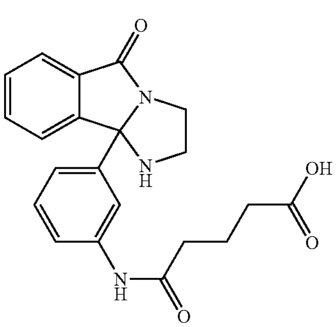 [SMILES: O=C(O)CCCC(=O)Nc1cccc(C23NCCN2C(=O)c2ccccc23)c1] | 380 | H |
| 128 | | 366 | H |
| 130 | | 414 | B |
| 131 | | 350 | H |
| 132 | | 341 | G |
| 133 | | 362 | F |

TABLE 1-continued

Compounds of Formula III (Intermediates).

| No | Structure | m/z M + H+ | Mtd |
|---|---|---|---|
| 134 | 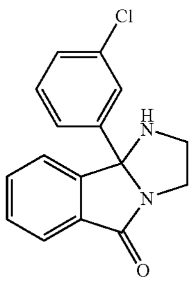 [SMILES: O=C1c2ccccc2C2(c3cccc(Cl)c3)NCCN12] | 285 | A |
| 136 | 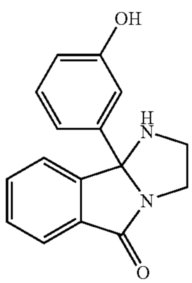 [SMILES: O=C1c2ccccc2C2(c3cccc(O)c3)NCCN12] | 267 | A |
| 140 | 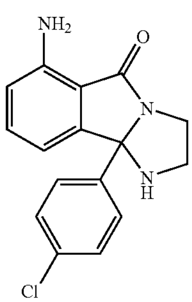 [SMILES: Nc1cccc2c1C(=O)N1CCNC21c1ccc(Cl)cc1] | 300 | A |
| 142 | 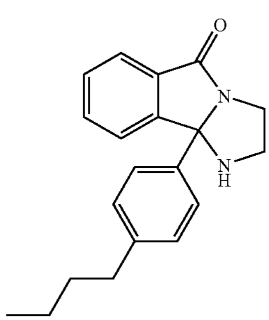 [SMILES: CCCCc1ccc(C23NCCN2C(=O)c2ccccc23)cc1] | 307 | A |
| 150 | 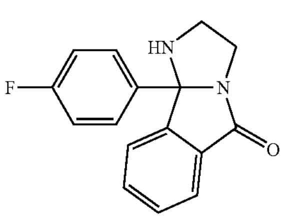 [SMILES: O=C1c2ccccc2C2(c3ccc(F)cc3)NCCN12] | 269 | A |
| 151 | 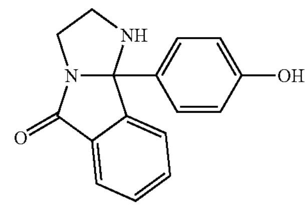 [SMILES: O=C1c2ccccc2C2(c3ccc(O)cc3)NCCN12] | 267 | A |
| 152 | 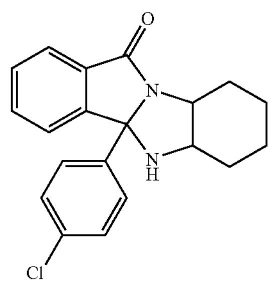 [SMILES: O=C1c2ccccc2C2(c3ccc(Cl)cc3)NC3CCCCC3N12] | 339 | A |
| 153 | 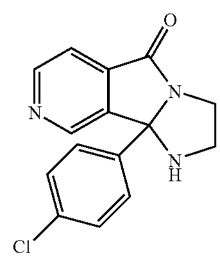 [SMILES: O=C1c2ccncc2C2(c3ccc(Cl)cc3)NCCN12] | 286 | N |
| 154 | 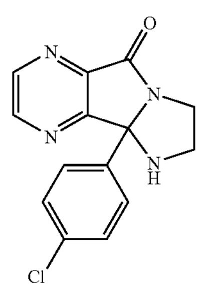 [SMILES: O=C1c2nccnc2C2(c3ccc(Cl)cc3)NCCN12] | 287 | A |
| 155 | 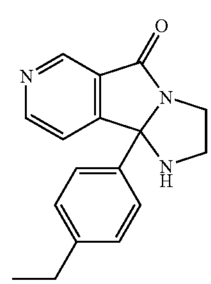 [SMILES: CCc1ccc(C23NCCN2C(=O)c2cnccc23)cc1] | 280 | A |

TABLE 1-continued

Compounds of Formula III (Intermediates).

| No | Structure | m/z M + H+ | Mtd |
|----|-----------|------------|-----|
| 156 | 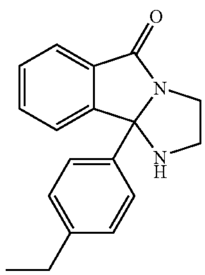 [SMILES: CCc1ccc(C23NCCN2C(=O)c2ccccc23)cc1] | 279 | A |
| 157 | 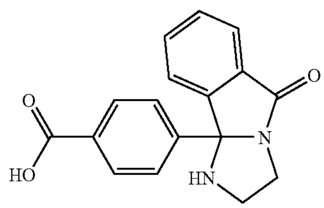 [SMILES: O=C(O)c1ccc(C23NCCN2C(=O)c2ccccc23)cc1] | * | A |
| 158 | 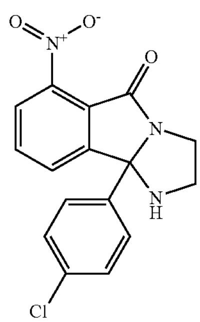 [SMILES: O=C1c2c([N+](=O)[O-])cccc2C2(c3ccc(Cl)cc3)NCCN12] | 330 | A |
| 159 | 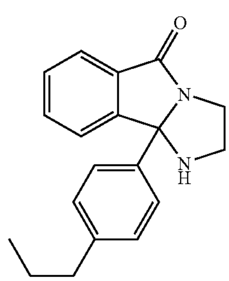 [SMILES: CCCc1ccc(C23NCCN2C(=O)c2ccccc23)cc1] | 293 | A |
| 160 | 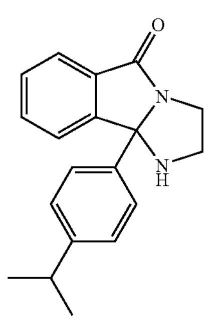 [SMILES: CC(C)c1ccc(C23NCCN2C(=O)c2ccccc23)cc1] | 293 | A |
| 161 | | 329 | A |
| 162 | | 286 | A |
| 163 | | 319 | A |
| 164 | | 320 | A |
| 165 | | 287 | A |

TABLE 1-continued

Compounds of Formula III (Intermediates).

| No | Structure | m/z M + H+ | Mtd |
|---|---|---|---|
| 166 | 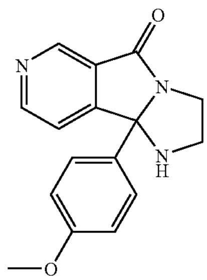 | 282 | A |
| 167 | 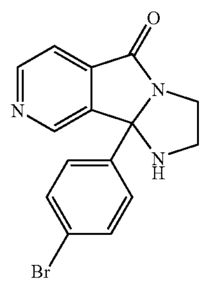 [SMILES: O=C1c2ccncc2C2(c3ccc(Br)cc3)NCCN12] | 332 | A |
| 168 | 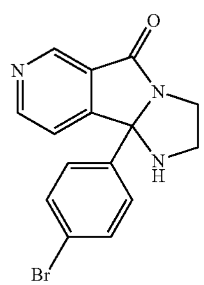 [SMILES: O=C1c2cnccc2C2(c3ccc(Br)cc3)NCCN12] | 332 | A |
| 169 | 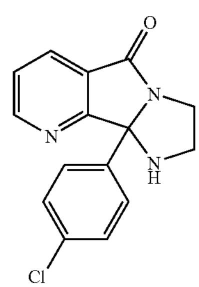 [SMILES: O=C1c2cccnc2C2(c3ccc(Cl)cc3)NCCN12] | 286 | A |
| 170 | 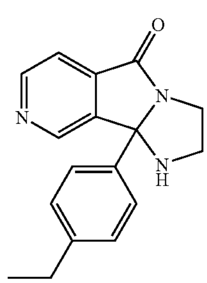 | 280 | A |
| 171 | 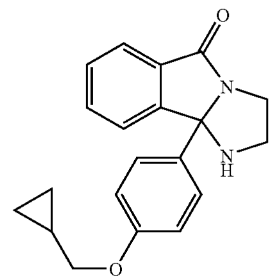 [SMILES: O=C1c2ccccc2C2(c3ccc(OCC4CC4)cc3)NCCN12] | 321 | A |
| 176 | 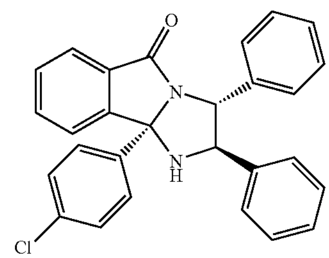 [SMILES: O=C1c2ccccc2[C@]2(c3ccc(Cl)cc3)N[C@H](c3ccccc3)[C@@H](c3ccccc3)N12] | 437 | A |
| 177 | 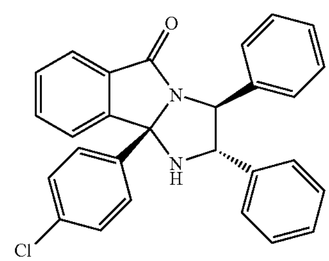 [SMILES: O=C1c2ccccc2[C@@]2(c3ccc(Cl)cc3)N[C@@H](c3ccccc3)[C@H](c3ccccc3)N12] | 437 | A |

TABLE 2

Compounds of the Invention (Formula I where A is Aryl)

| No. | Structure | m/z M + H+ | Mtd |
|---|---|---|---|
| 12 | 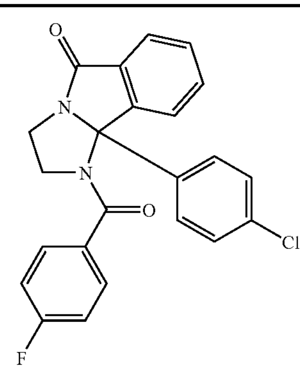 | 407 | B |

TABLE 2-continued

Compounds of the Invention (Formula I where A is Aryl)

| No. | Structure | m/z M + H⁺ | Mtd |
|---|---|---|---|
| 13 | 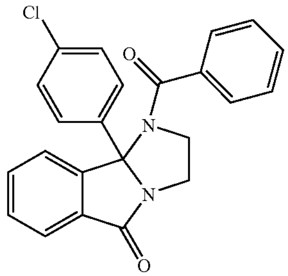 [SMILES: O=C(c1ccccc1)N1CCN2C(=O)c3ccccc3C12c1ccc(Cl)cc1] | 389 | B |
| 14 | 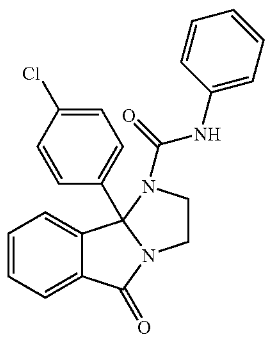 [SMILES: O=C(Nc1ccccc1)N1CCN2C(=O)c3ccccc3C12c1ccc(Cl)cc1] | 404 | E |
| 15 | 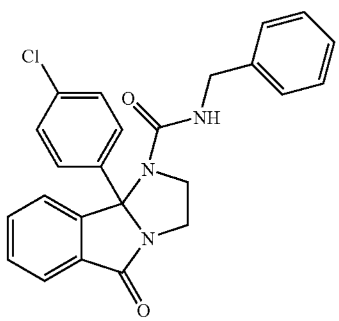 [SMILES: O=C(NCc1ccccc1)N1CCN2C(=O)c3ccccc3C12c1ccc(Cl)cc1] | 418 | E |
| 16 | 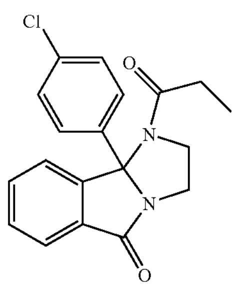 [SMILES: CCC(=O)N1CCN2C(=O)c3ccccc3C12c1ccc(Cl)cc1] | 341 | B |
| 17 | 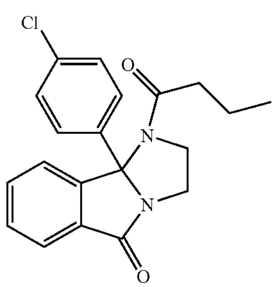 | 355 | B |
| 18 | 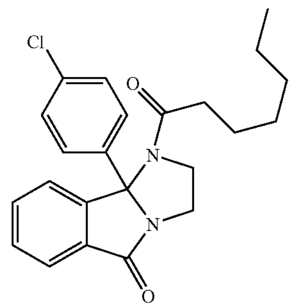 | 397 | B |
| 19 | 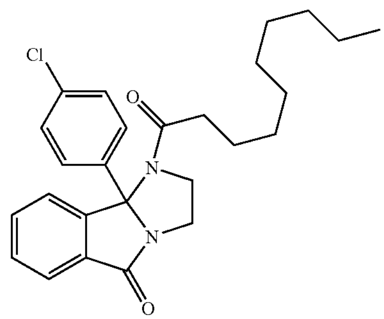 [SMILES: CCCCCCCCCC(=O)N1CCN2C(=O)c3ccccc3C12c1ccc(Cl)cc1] | 439 | B |
| 20 | 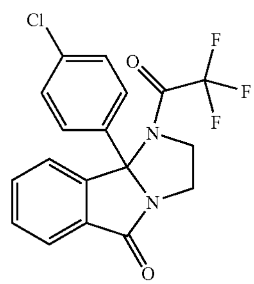 [SMILES: O=C1c2ccccc2C2(c3ccc(Cl)cc3)N1CCN2C(=O)C(F)(F)F] | 381 | B |
| 21 | 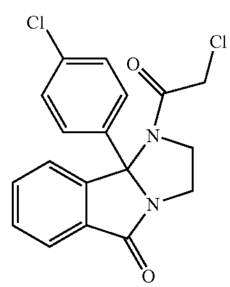 [SMILES: O=C(CCl)N1CCN2C(=O)c3ccccc3C12c1ccc(Cl)cc1] | 361 | B |
| 22 | 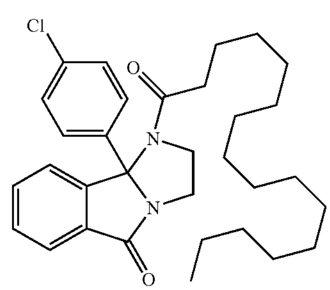 [SMILES: CCCCCCCCCCCCCCCC(=O)N1CCN2C(=O)c3ccccc3C12c1ccc(Cl)cc1] | 523 | B |

TABLE 2-continued
Compounds of the Invention (Formula I where A is Aryl)
| No. | Structure | m/z M+H+ | Mtd |
|---|---|---|---|
| 23 | 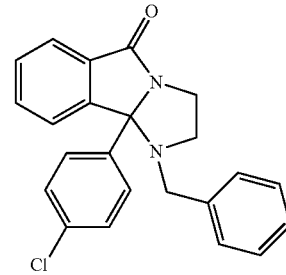 | 375 | D |
| 24 | 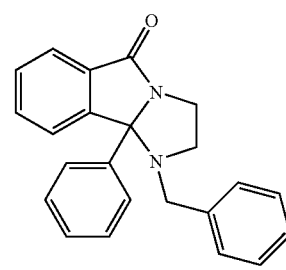 | 341 | D |
| 25 | 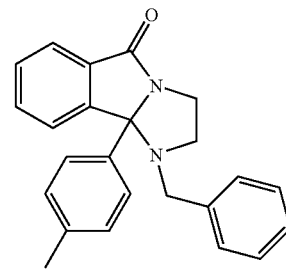 | 355 | D |
| 26 | 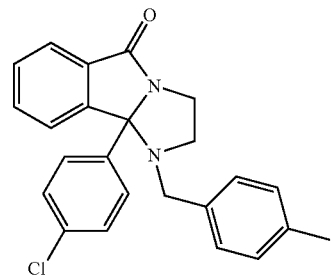 [SMILES: Cc1ccc(CN2CCN3C(=O)c4ccccc4C23c2ccc(Cl)cc2)cc1] | 389 | D |
| 27 | 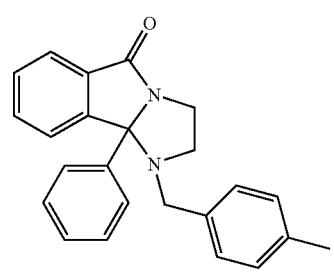 [SMILES: Cc1ccc(CN2CCN3C(=O)c4ccccc4C23c2ccccc2)cc1] | 355 | D |
| 28 | 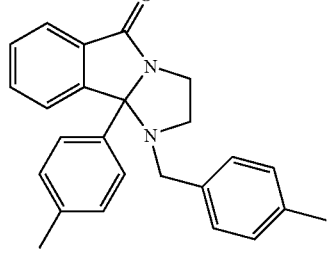 | 369 | D |
| 29 | 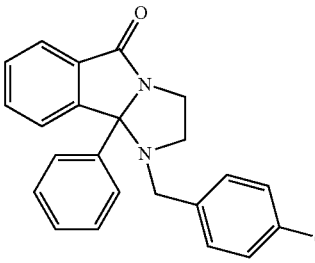 | 375 | D |
| 30 | 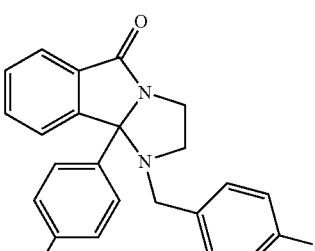 | 409 | D |
| 31 | 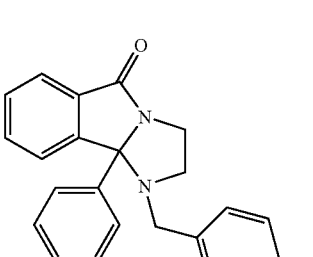 | 389 | D |
| 32 | 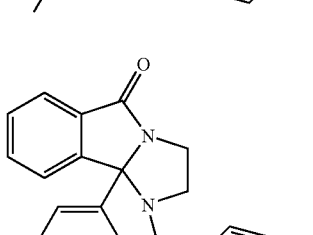 | 393 | D |

TABLE 2-continued

Compounds of the Invention (Formula I where A is Aryl)

| No. | Structure | m/z M+H+ | Mtd |
|-----|-----------|----------|-----|
| 33 | 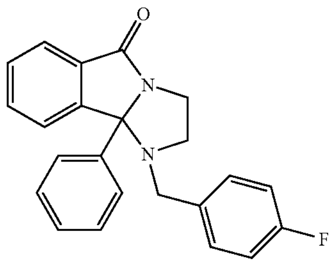 [SMILES: O=C1c2ccccc2C2(c3ccccc3)N(Cc3ccc(F)cc3)CCN12] | 359 | D |
| 34 | 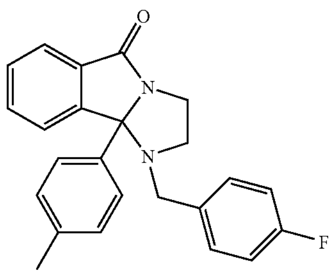 [SMILES: Cc1ccc(C23c4ccccc4C(=O)N2CCN3Cc2ccc(F)cc2)cc1] | 373 | D |
| 35 | 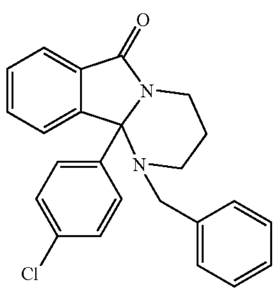 [SMILES: O=C1c2ccccc2C2(c3ccc(Cl)cc3)N(Cc3ccccc3)CCCN12] | 389 | D |
| 36 | 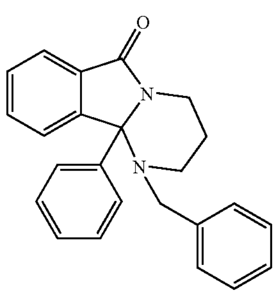 [SMILES: O=C1c2ccccc2C2(c3ccccc3)N(Cc3ccccc3)CCCN12] | 355 | D |
| 37 | 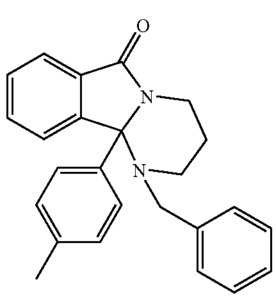 [SMILES: Cc1ccc(C23c4ccccc4C(=O)N2CCCN3Cc2ccccc2)cc1] | 369 | D |
| 38 | | 407 | D |
| 39 | | 373 | D |
| 40 | | 387 | D |
| 41 | | 469 | C |
| 42 | | 515 | C |

TABLE 2-continued

Compounds of the Invention (Formula I where A is Aryl)

| No. | Structure | m/z M + H⁺ | Mtd |
|---|---|---|---|
| 43 | 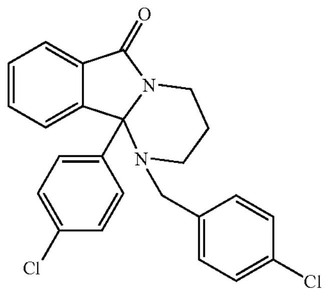 [SMILES: O=C1c2ccccc2C2(c3ccc(Cl)cc3)N(Cc3ccc(Cl)cc3)CCCN12] | 423 | D |
| 44 | 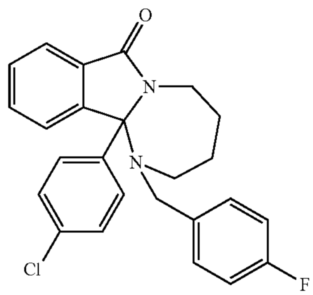 [SMILES: O=C1c2ccccc2C2(c3ccc(Cl)cc3)N(Cc3ccc(F)cc3)CCCCN12] | 421 | D |
| 45 | 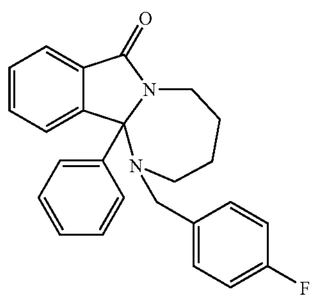 [SMILES: O=C1c2ccccc2C2(c3ccccc3)N(Cc3ccc(F)cc3)CCCCN12] | 387 | D |
| 46 | 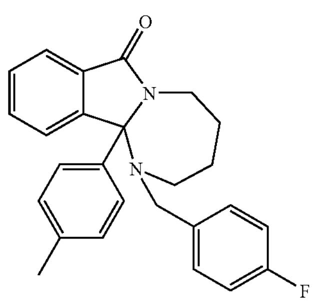 [SMILES: Cc1ccc(C23c4ccccc4C(=O)N2CCCCN3Cc2ccc(F)cc2)cc1] | 401 | D |
| 47 | 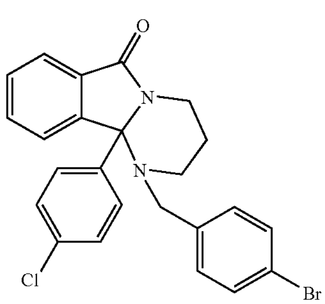 [SMILES: O=C1c2ccccc2C2(c3ccc(Cl)cc3)N(Cc3ccc(Br)cc3)CCCN12] | 468 | D |
| 48 | | 403 | D |
| 49 | | 423 | C |
| 50 | | 403 | C |
| 51 | | 419 | C |
| 52 | | 473 | C |

TABLE 2-continued
Compounds of the Invention (Formula I where A is Aryl)
| No. | Structure | m/z M+H+ | Mtd |
|---|---|---|---|
| 53 | 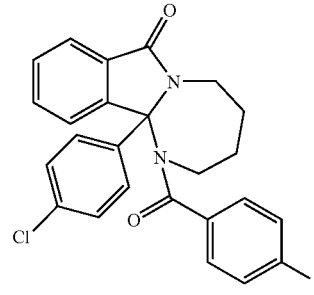 | 457 | C |
| 54 | | 495 | C |
| 55 | | 481 | C |
| 56 | | 431 | C |
| 57 | 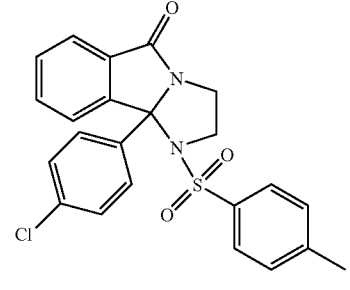 | 435 | C |
| 58 | 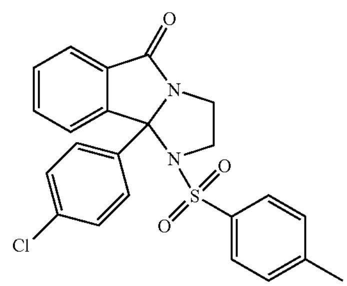 [SMILES: Cc1ccc(S(=O)(=O)N2CCN3C(=O)c4ccccc4C32c2ccc(Cl)cc2)cc1] | 439 | D |
| 59 | 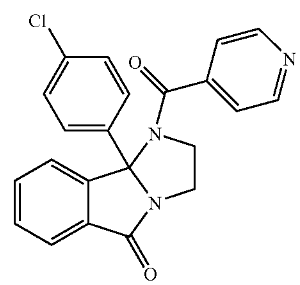 [SMILES: O=C(c1ccncc1)N1CCN2C(=O)c3ccccc3C12c1ccc(Cl)cc1] | 390 | C |
| 60 | 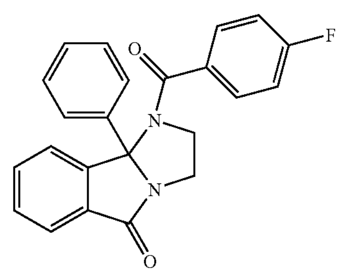 [SMILES: O=C(c1ccc(F)cc1)N1CCN2C(=O)c3ccccc3C12c1ccccc1] | 373 | C |
| 61 | 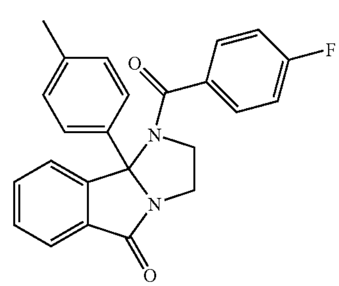 [SMILES: Cc1ccc(C23c4ccccc4C(=O)N2CCN3C(=O)c2ccc(F)cc2)cc1] | 387 | C |

TABLE 2-continued
Compounds of the Invention (Formula I where A is Aryl)
| No. | Structure | m/z M+H+ | Mtd |
|---|---|---|---|
| 62 | 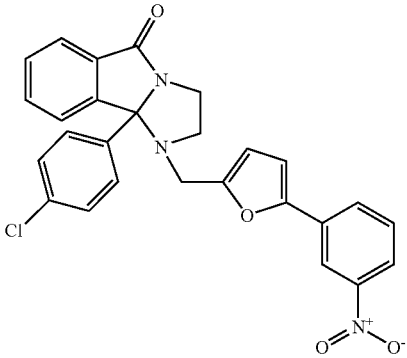 [SMILES: O=C1c2ccccc2C2(c3ccc(Cl)cc3)N(Cc3ccc(-c4cccc([N+](=O)[O-])c4)o3)CCN12] | 486 | D |
| 64 | 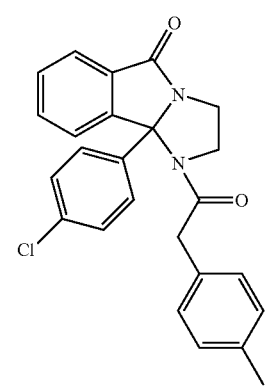 [SMILES: Cc1ccc(CC(=O)N2CCN3C(=O)c4ccccc4C23c2ccc(Cl)cc2)cc1] | 417 | C |
| 65 | 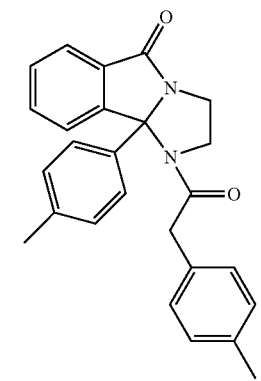 | 397 | C |
| 66 | 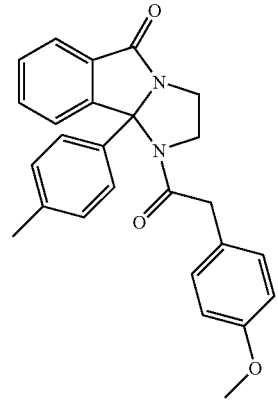 [SMILES: COc1ccc(CC(=O)N2CCN3C(=O)c4ccccc4C23c2ccc(C)cc2)cc1] | 413 | C |
| 67 | | 433 | C |
| 68 | 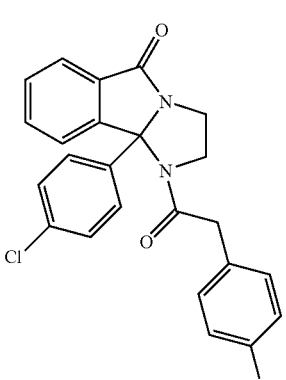 | 417 | C |

TABLE 2-continued

Compounds of the Invention (Formula I where A is Aryl)

| No. | Structure | m/z M + H⁺ | Mtd |
|---|---|---|---|
| 69 | 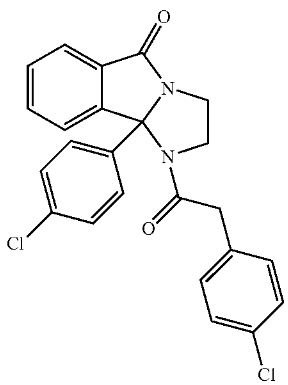 [SMILES: O=C(Cc1ccc(Cl)cc1)N1CCN2C(=O)c3ccccc3C12c1ccc(Cl)cc1] | 437 | C |
| 70 | 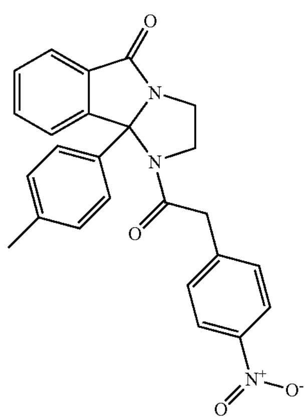 [SMILES: Cc1ccc(C23c4ccccc4C(=O)N2CCN3C(=O)Cc2ccc([N+](=O)[O-])cc2)cc1] | 428 | C |
| 71 | 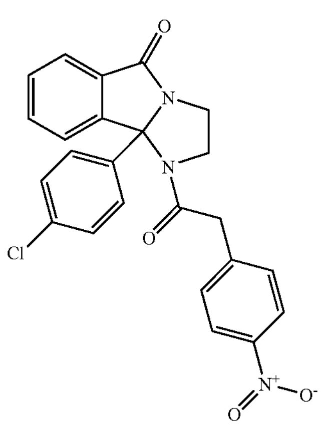 [SMILES: O=C(Cc1ccc([N+](=O)[O-])cc1)N1CCN2C(=O)c3ccccc3C12c1ccc(Cl)cc1] | 448 | C |
| 72 | 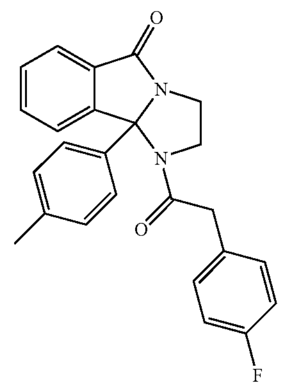 [SMILES: Cc1ccc(C23c4ccccc4C(=O)N2CCN3C(=O)Cc2ccc(F)cc2)cc1] | 401 | C |
| 73 | 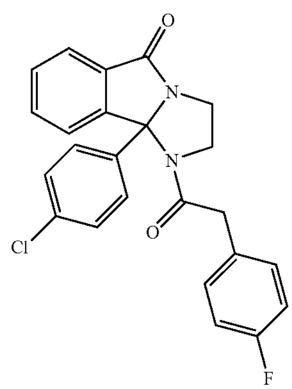 [SMILES: O=C(Cc1ccc(F)cc1)N1CCN2C(=O)c3ccccc3C12c1ccc(Cl)cc1] | 421 | C |
| 74 | 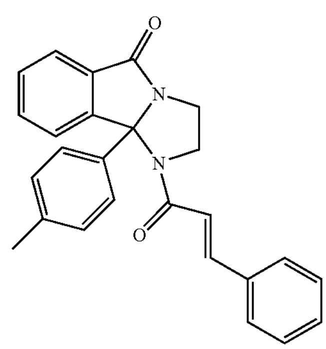 [SMILES: Cc1ccc(C23c4ccccc4C(=O)N2CCN3C(=O)/C=C/c2ccccc2)cc1] | 395 | C |
| 75 | 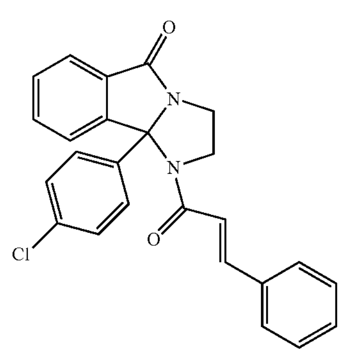 [SMILES: O=C(/C=C/c1ccccc1)N1CCN2C(=O)c3ccccc3C12c1ccc(Cl)cc1] | 415 | C |

TABLE 2-continued

Compounds of the Invention (Formula I where A is Aryl)

| No. | Structure | m/z M+H+ | Mtd |
|---|---|---|---|
| 76 | 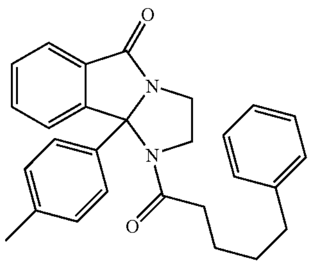 [SMILES: Cc1ccc(C23c4ccccc4C(=O)N2CCN3C(=O)CCCCc2ccccc2)cc1] | 425 | C |
| 77 | 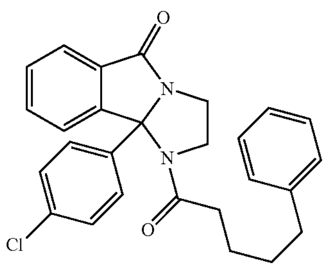 [SMILES: O=C(CCCCc1ccccc1)N1CCN2C(=O)c3ccccc3C12c1ccc(Cl)cc1] | 445 | C |
| 79 | 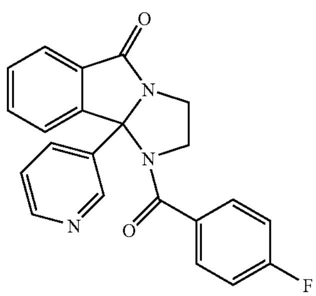 [SMILES: O=C(c1ccc(F)cc1)N1CCN2C(=O)c3ccccc3C12c1cccnc1] | 374 | C |
| 80 | 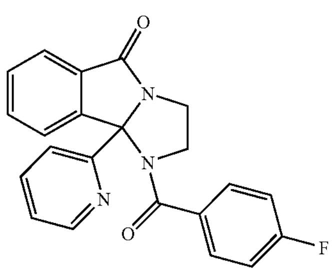 [SMILES: O=C(c1ccc(F)cc1)N1CCN2C(=O)c3ccccc3C12c1ccccn1] | 374 | C |
| 81 | 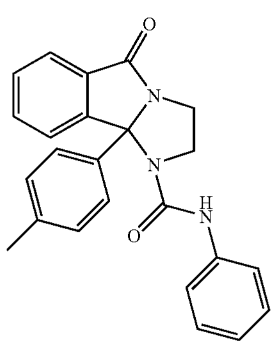 [SMILES: Cc1ccc(C23c4ccccc4C(=O)N2CCN3C(=O)Nc2ccccc2)cc1] | 384 | E |
| 82 | | 398 | E |
| 83 | | 477 | E |
| 84 | | 497 | E |
| 85 | | 434 | E |

TABLE 2-continued

Compounds of the Invention (Formula I where A is Aryl)

| No. | Structure | m/z M+H⁺ | Mtd |
|---|---|---|---|
| 86 | | 414 | E |
| 87 | | 436 | E |
| 88 | | 416 | E |
| 89 | | 432 | E |
| 91 | 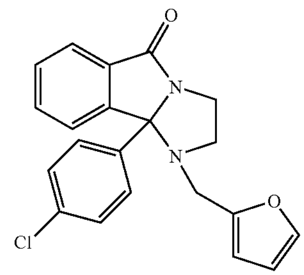 [SMILES: O=C1c2ccccc2C2(c3ccc(Cl)cc3)N(Cc3ccco3)CCN12] | 365 | D |
| 94 | 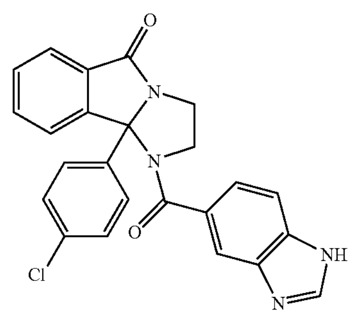 [SMILES: O=C(c1ccc2[nH]cnc2c1)N1CCN2C(=O)c3ccccc3C12c1ccc(Cl)cc1] | 429 | B |
| 98 | 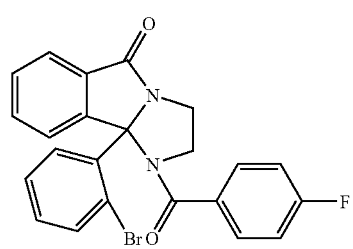 [SMILES: O=C(c1ccc(F)cc1)N1CCN2C(=O)c3ccccc3C12c1ccccc1Br] | 453 | B |
| 99 | 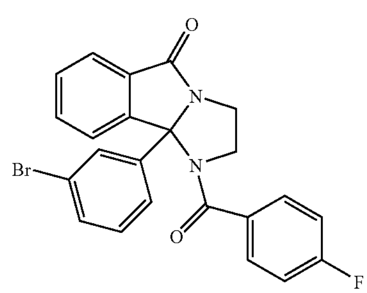 [SMILES: O=C(c1ccc(F)cc1)N1CCN2C(=O)c3ccccc3C12c1cccc(Br)c1] | 453 | B |
| 101 | 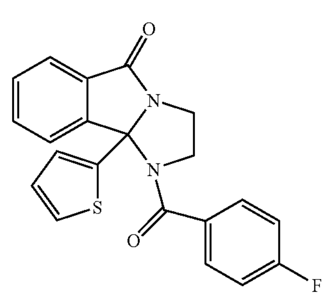 [SMILES: O=C(c1ccc(F)cc1)N1CCN2C(=O)c3ccccc3C12c1cccs1] | 379 | B |

TABLE 2-continued

Compounds of the Invention (Formula I where A is Aryl)

| No. | Structure | m/z M+H+ | Mtd |
|---|---|---|---|
| 104 | 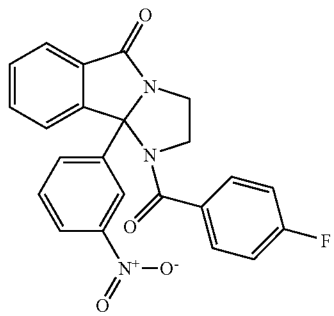 [SMILES: O=C(c1ccc(F)cc1)N1CCN2C(=O)c3ccccc3C12c1cccc([N+](=O)[O-])c1] | 418 | B |
| 105 | 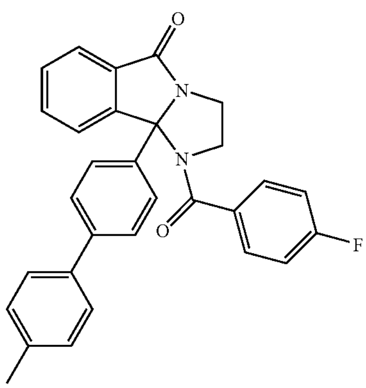 [SMILES: Cc1ccc(-c2ccc(C34c5ccccc5C(=O)N3CCN4C(=O)c3ccc(F)cc3)cc2)cc1] | 463 | B |
| 108 | 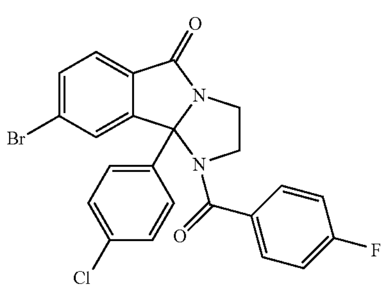 [SMILES: O=C(c1ccc(F)cc1)N1CCN2C(=O)c3ccc(Br)cc3C12c1ccc(Cl)cc1] | 487 | C |
| 109 | 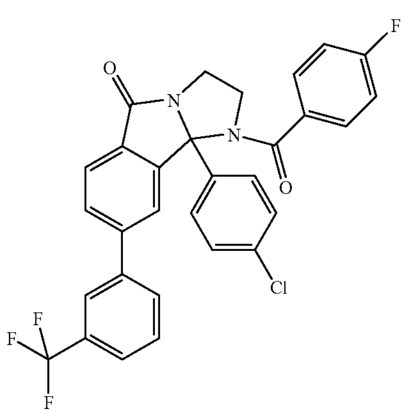 [SMILES: O=C(c1ccc(F)cc1)N1CCN2C(=O)c3ccc(-c4cccc(C(F)(F)F)c4)cc3C12c1ccc(Cl)cc1] | 551 | H |
| 114 | 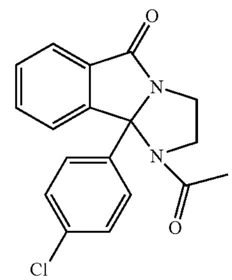 [SMILES: CC(=O)N1CCN2C(=O)c3ccccc3C12c1ccc(Cl)cc1] | 327 | H |
| 117 | 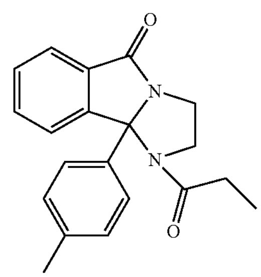 [SMILES: CCC(=O)N1CCN2C(=O)c3ccccc3C12c1ccc(C)cc1] | 321 | B |
| 118 | 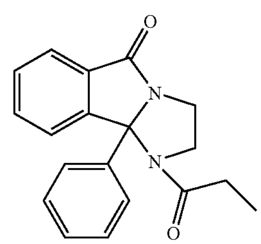 [SMILES: CCC(=O)N1CCN2C(=O)c3ccccc3C12c1ccccc1] | 307 | B |
| 124 | 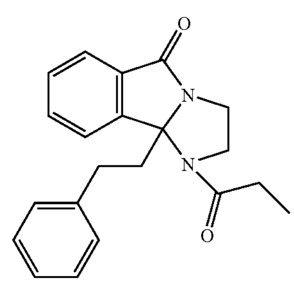 [SMILES: CCC(=O)N1CCN2C(=O)c3ccccc3C12CCc1ccccc1] | 335 | H |
| 125 | 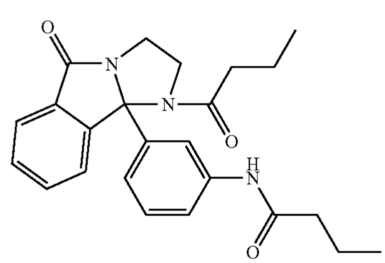 [SMILES: CCCC(=O)Nc1cccc(C23c4ccccc4C(=O)N2CCN3C(=O)CCC)c1] | 406 | H |

TABLE 2-continued

Compounds of the Invention (Formula I where A is Aryl)

| No. | Structure | m/z M+H⁺ | Mtd |
|---|---|---|---|
| 129 | 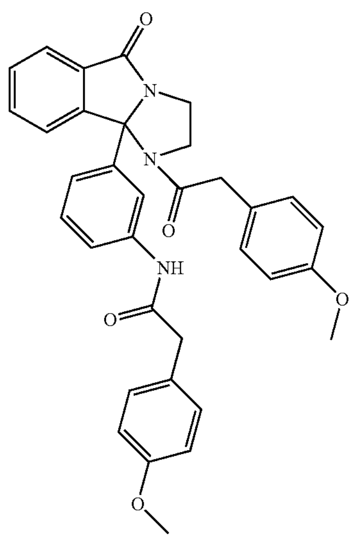 [SMILES: COc1ccc(CC(=O)Nc2cccc(C34c5ccccc5C(=O)N3CCN4C(=O)Cc3ccc(OC)cc3)c2)cc1] | 562 | H |
| 135 | 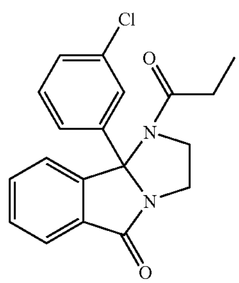 [SMILES: CCC(=O)N1CCN2C(=O)c3ccccc3C12c1cccc(Cl)c1] | 341 | H |
| 137 | 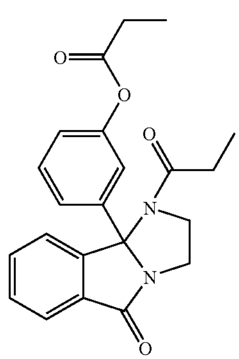 [SMILES: CCC(=O)Oc1cccc(C23c4ccccc4C(=O)N2CCN3C(=O)CC)c1] | 379 | H |
| 138 | 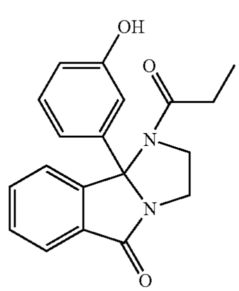 | 323 | L |
| 139 | | 484 | C |
| 143 | | 350 | H |
| 144 | | 407 | H |
| 145 | | 429 | H |

TABLE 2-continued

Compounds of the Invention (Formula I where A is Aryl)

| No. | Structure | m/z M+H⁺ | Mtd |
|---|---|---|---|
| 146 | 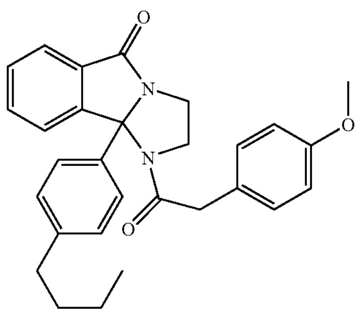 [SMILES: CCCCc1ccc(C23c4ccccc4C(=O)N2CCN3C(=O)Cc2ccc(OC)cc2)cc1] | 455 | H |
| 147 | 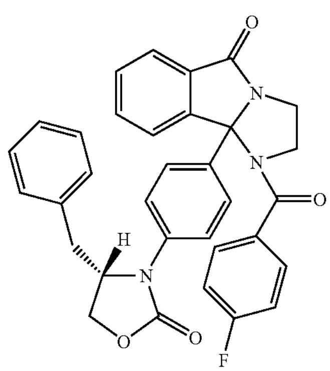 [SMILES: O=C1OC[C@H](Cc2ccccc2)N1c1ccc(C23c4ccccc4C(=O)N2CCN3C(=O)c2ccc(F)cc2)cc1] | 548 | H |
| 172 | 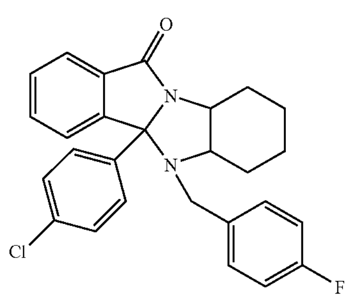 [SMILES: O=C1c2ccccc2C2(c3ccc(Cl)cc3)N(Cc3ccc(F)cc3)C3CCCCC3N12] | 447 | D |
| 173 | 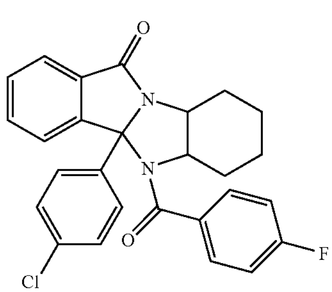 [SMILES: O=C(c1ccc(F)cc1)N1C2CCCCC2N2C(=O)c3ccccc3C12c1ccc(Cl)cc1] | 461 | C |
| 174 | 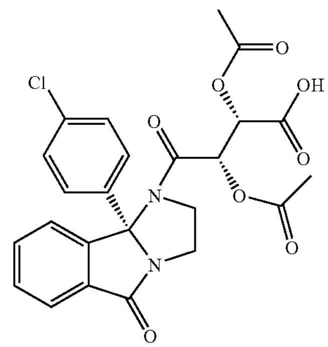 [SMILES: CC(=O)O[C@H](C(=O)O)[C@H](OC(C)=O)C(=O)N1CCN2C(=O)c3ccccc3[C@]21c1ccc(Cl)cc1] | 501 | B |
| 175 | 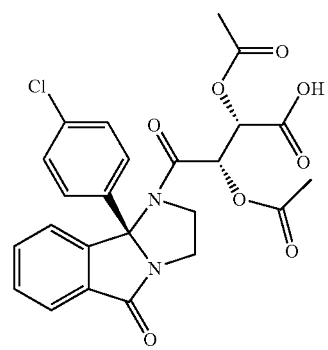 [SMILES: CC(=O)O[C@H](C(=O)O)[C@H](OC(C)=O)C(=O)N1CCN2C(=O)c3ccccc3[C@@]21c1ccc(Cl)cc1] | 501 | B |
| 178 | 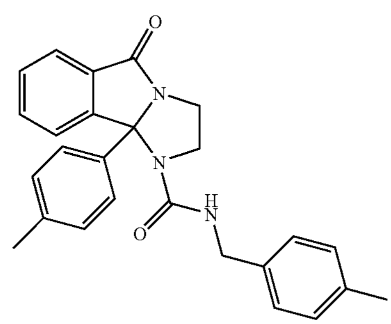 | 412 | E |
| 179 | 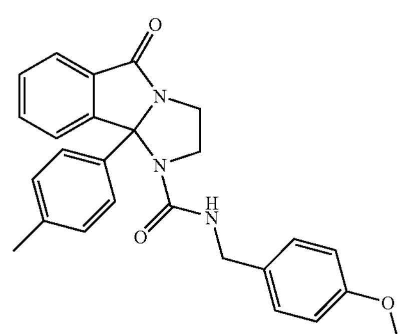 | 428 | E |

TABLE 2-continued
Compounds of the Invention (Formula I where A is Aryl)
| No. | Structure | m/z M+H⁺ | Mtd |
|---|---|---|---|
| 180 | 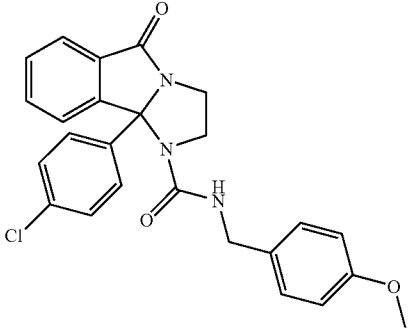 [SMILES: COc1ccc(CNC(=O)N2CCN3C(=O)c4ccccc4C23c2ccc(Cl)cc2)cc1] | 448 | E |
| 181 | 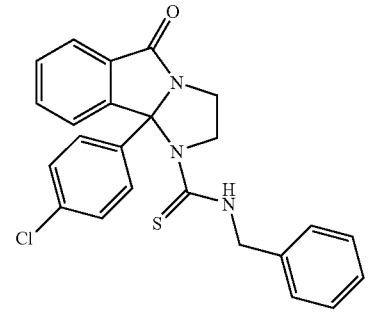 [SMILES: O=C1c2ccccc2C2(c3ccc(Cl)cc3)N1CCN2C(=S)NCc1ccccc1] | 434 | E |
| 182 | 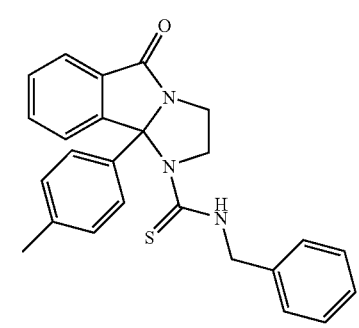 | 414 | E |
| 183 | 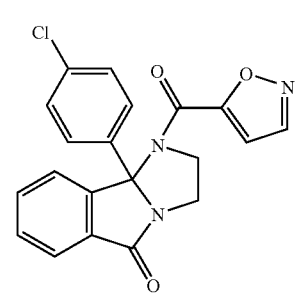 [SMILES: O=C(c1ccno1)N1CCN2C(=O)c3ccccc3C12c1ccc(Cl)cc1] | 380 | H |
| 184 | 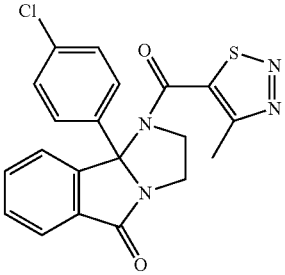 | 411 | H |
| 185 | 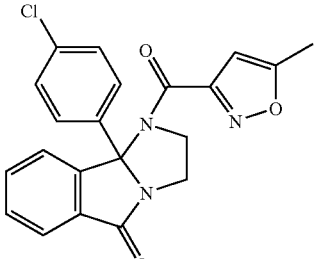 | 394 | H |
| 186 | 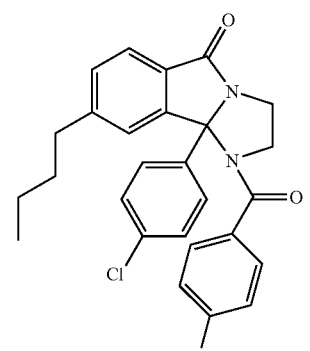 | 463 | H |
| 187 | 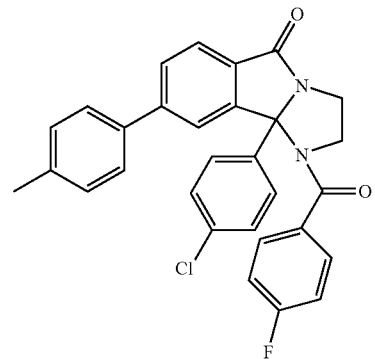 [SMILES: Cc1ccc(-c2ccc3c(c2)C2(c4ccc(Cl)cc4)N(C(=O)c4ccc(F)cc4)CCN2C3=O)cc1] | 497 | H |

TABLE 2-continued

Compounds of the Invention (Formula I where A is Aryl)

| No. | Structure | m/z M+H⁺ | Mtd |
|---|---|---|---|
| 188 | 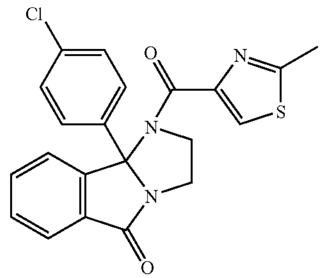 [SMILES: Cc1nc(C(=O)N2CCN3C(=O)c4ccccc4C23c2ccc(Cl)cc2)cs1] | 410 | H |
| 189 | 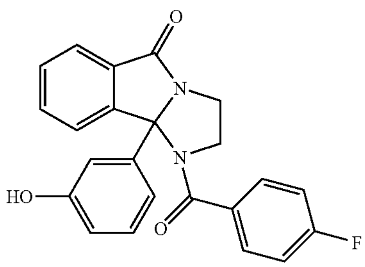 [SMILES: O=C(c1ccc(F)cc1)N1CCN2C(=O)c3ccccc3C12c1cccc(O)c1] | 389 | L |
| 190 | 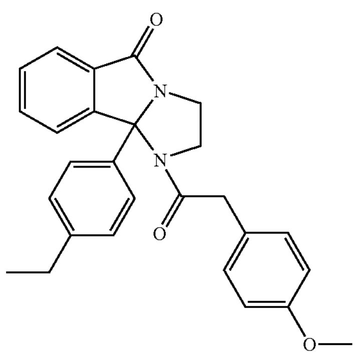 [SMILES: CCc1ccc(C23c4ccccc4C(=O)N2CCN3C(=O)Cc2ccc(OC)cc2)cc1] | 427 | H |
| 191 | 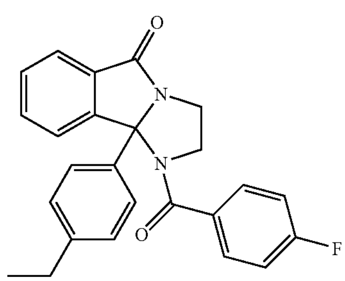 [SMILES: CCc1ccc(C23c4ccccc4C(=O)N2CCN3C(=O)c2ccc(F)cc2)cc1] | 401 | H |
| 192 | 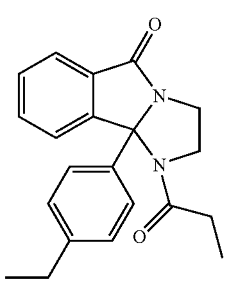 [SMILES: CCC(=O)N1CCN2C(=O)c3ccccc3C12c1ccc(CC)cc1] | 335 | H |
| 193 | | 337 | H |
| 194 | | 403 | H |
| 195 | | 429 | H |
| 196 | | 492 | H |

TABLE 2-continued

Compounds of the Invention (Formula I where A is Aryl)

| No. | Structure | m/z M+H⁺ | Mtd |
|---|---|---|---|
| 197 | 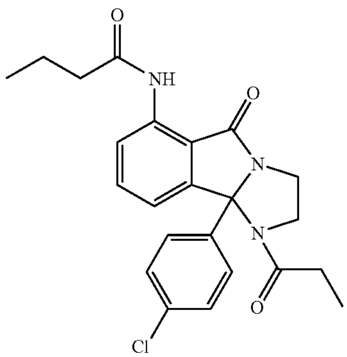 [SMILES: CCCC(=O)Nc1cccc2c1C(=O)N1CCN(C(=O)CC)C21c1ccc(Cl)cc1] | 426 | H |
| 198 | 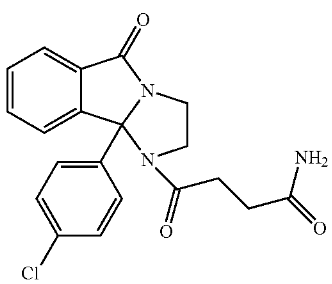 [SMILES: NC(=O)CCC(=O)N1CCN2C(=O)c3ccccc3C12c1ccc(Cl)cc1] | 384 | H |
| 199 | 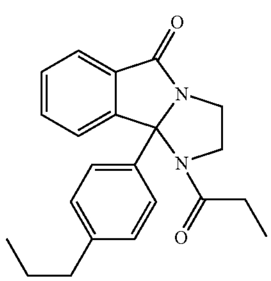 [SMILES: CCCc1ccc(C23c4ccccc4C(=O)N2CCN3C(=O)CC)cc1] | 349 | H |
| 200 | 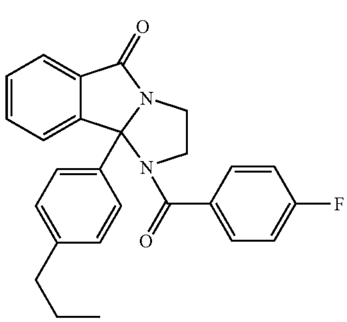 [SMILES: CCCc1ccc(C23c4ccccc4C(=O)N2CCN3C(=O)c2ccc(F)cc2)cc1] | 415 | H |
| 201 | 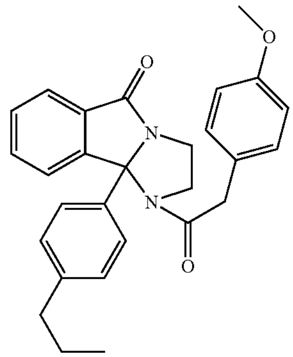 [SMILES: CCCc1ccc(C23c4ccccc4C(=O)N2CCN3C(=O)Cc2ccc(OC)cc2)cc1] | 441 | H |
| 202 | 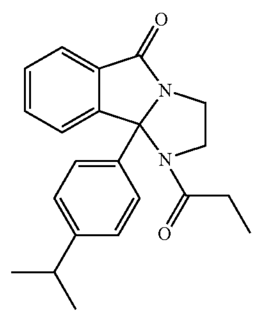 [SMILES: CCC(=O)N1CCN2C(=O)c3ccccc3C12c1ccc(C(C)C)cc1] | 349 | H |
| 203 | 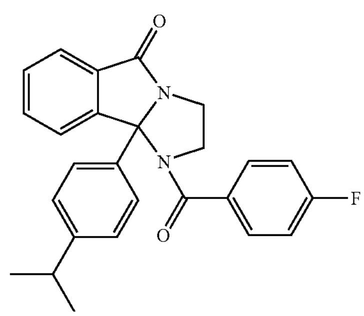 | 415 | H |
| 204 | 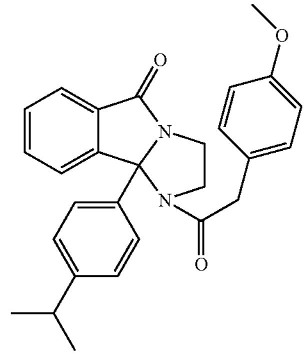 [SMILES: COc1ccc(CC(=O)N2CCN3C(=O)c4ccccc4C23c2ccc(C(C)C)cc2)cc1] | 441 | H |

TABLE 2-continued

Compounds of the Invention (Formula I where A is Aryl)

| No. | Structure | m/z M+H⁺ | Mtd |
|---|---|---|---|
| 205 | 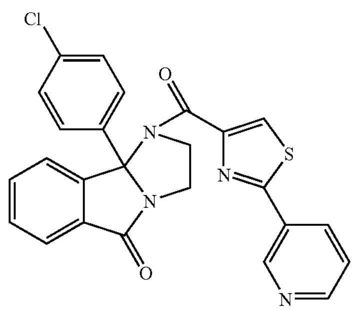 [SMILES: O=C(c1csc(-c2cccnc2)n1)N1CCN2C(=O)c3ccccc3C12c1ccc(Cl)cc1] | 473 | C |
| 206 | 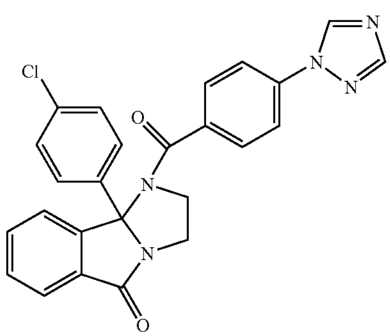 [SMILES: O=C(c1ccc(-n2cncn2)cc1)N1CCN2C(=O)c3ccccc3C12c1ccc(Cl)cc1] | 456 | C |
| 207 | 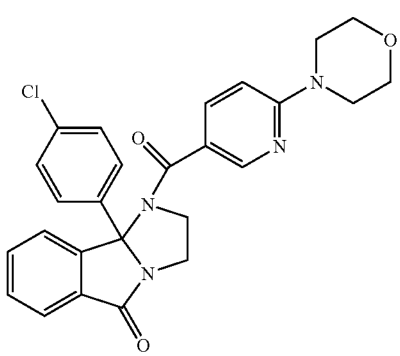 [SMILES: O=C(c1ccc(N2CCOCC2)nc1)N1CCN2C(=O)c3ccccc3C12c1ccc(Cl)cc1] | 475 | C |
| 208 | 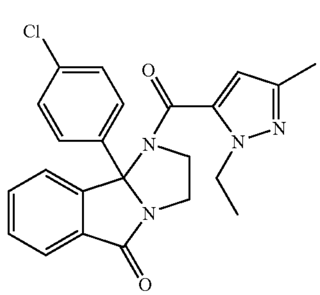 [SMILES: CCn1nc(C)cc1C(=O)N1CCN2C(=O)c3ccccc3C21c1ccc(Cl)cc1] | 421 | C |
| 209 | 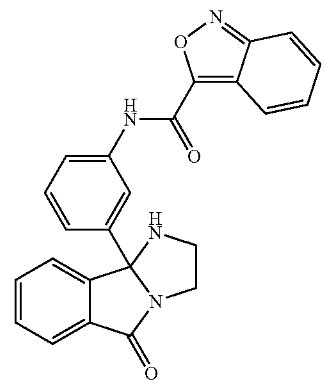 [SMILES: O=C(Nc1cccc(C23NCCN2C(=O)c2ccccc23)c1)c1onc2ccccc12] | 411 | I |
| 210 | 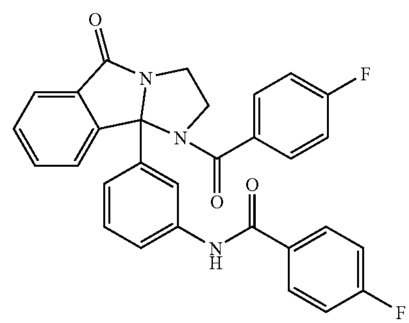 [SMILES: O=C(Nc1cccc(C23c4ccccc4C(=O)N2CCN3C(=O)c2ccc(F)cc2)c1)c1ccc(F)cc1] | 510 | I |
| 211 | 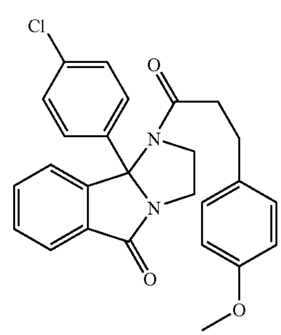 [SMILES: COc1ccc(CCC(=O)N2CCN3C(=O)c4ccccc4C23c2ccc(Cl)cc2)cc1] | 447 | I |
| 212 | 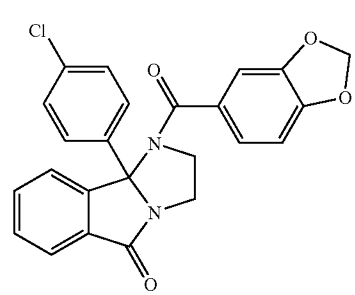 [SMILES: O=C(c1ccc2c(c1)OCO2)N1CCN2C(=O)c3ccccc3C12c1ccc(Cl)cc1] | 433 | I |

TABLE 2-continued

Compounds of the Invention (Formula I where A is Aryl)

| No. | Structure | m/z M+H+ | Mtd |
|---|---|---|---|
| 213 | 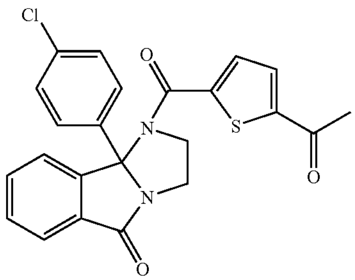 [SMILES: CC(=O)c1ccc(C(=O)N2CCN3C(=O)c4ccccc4C23c2ccc(Cl)cc2)s1] | 437 | I |
| 214 | 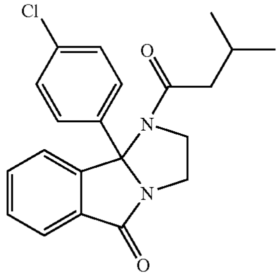 [SMILES: CC(C)CC(=O)N1CCN2C(=O)c3ccccc3C12c1ccc(Cl)cc1] | 369 | I |
| 215 | 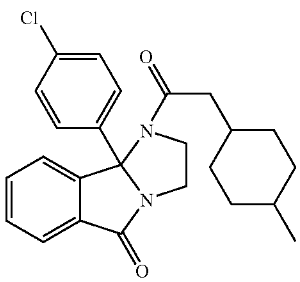 [SMILES: CC1CCC(CC(=O)N2CCN3C(=O)c4ccccc4C23c2ccc(Cl)cc2)CC1] | 423 | I |
| 216 | 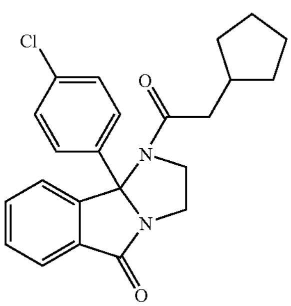 [SMILES: O=C(CC1CCCC1)N1CCN2C(=O)c3ccccc3C12c1ccc(Cl)cc1] | 395 | I |
| 217 | 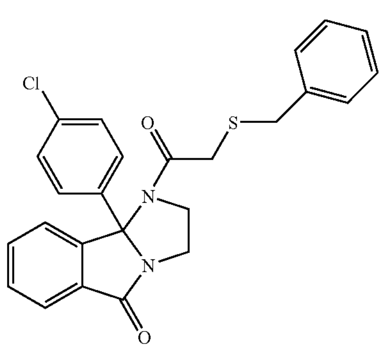 [SMILES: O=C(CSCc1ccccc1)N1CCN2C(=O)c3ccccc3C12c1ccc(Cl)cc1] | 449 | I |
| 218 | | 415 | I |
| 219 | | 379 | I |
| 220 | | 367 | I |
| 221 | | 353 | I |
| 222 | | 383 | I |

TABLE 2-continued

Compounds of the Invention (Formula I where A is Aryl)

| No. | Structure | m/z M+H⁺ | Mtd |
|---|---|---|---|
| 223 | 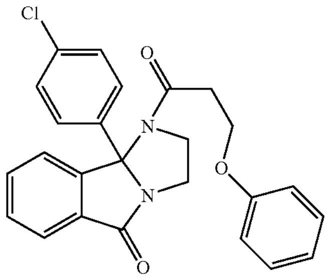 [SMILES: O=C(CCOc1ccccc1)N1CCN2C(=O)c3ccccc3C12c1ccc(Cl)cc1] | 433 | I |
| 224 | 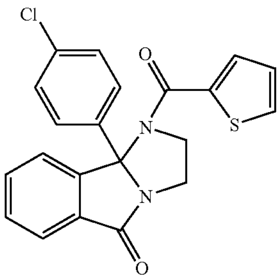 [SMILES: O=C(c1cccs1)N1CCN2C(=O)c3ccccc3C12c1ccc(Cl)cc1] | 395 | I |
| 225 | 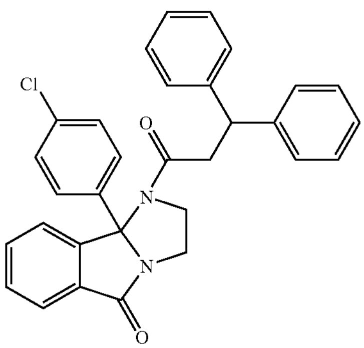 [SMILES: O=C(CC(c1ccccc1)c1ccccc1)N1CCN2C(=O)c3ccccc3C12c1ccc(Cl)cc1] | 493 | I |
| 226 | 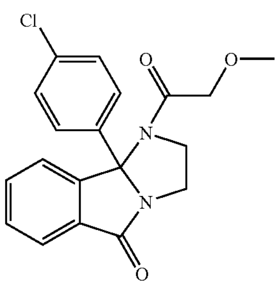 [SMILES: COCC(=O)N1CCN2C(=O)c3ccccc3C12c1ccc(Cl)cc1] | 357 | I |
| 227 | 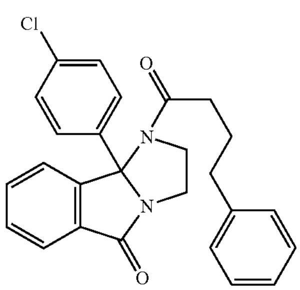 [SMILES: O=C(CCCc1ccccc1)N1CCN2C(=O)c3ccccc3C12c1ccc(Cl)cc1] | 431 | I |
| 228 | | 470 | I |
| 229 | | 401 | I |
| 230 | | 390 | H |
| 231 | | 391 | H |

TABLE 2-continued
Compounds of the Invention (Formula I where A is Aryl)
| No. | Structure | m/z M+H+ | Mtd |
|---|---|---|---|
| 232 | 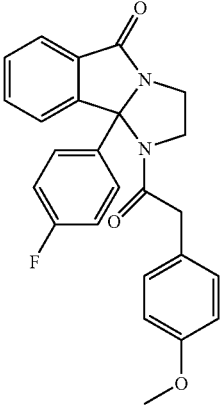 [SMILES: COc1ccc(CC(=O)N2CCN3C(=O)c4ccccc4C23c2ccc(F)cc2)cc1] | 417 | H |
| 233 | 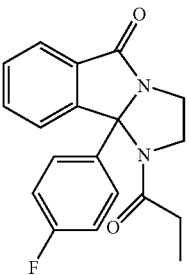 [SMILES: CCC(=O)N1CCN2C(=O)c3ccccc3C12c1ccc(F)cc1] | 325 | H |
| 234 | 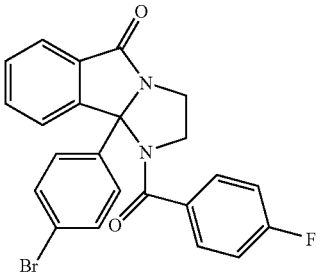 [SMILES: O=C(c1ccc(F)cc1)N1CCN2C(=O)c3ccccc3C12c1ccc(Br)cc1] | 453 | H |
| 235 | 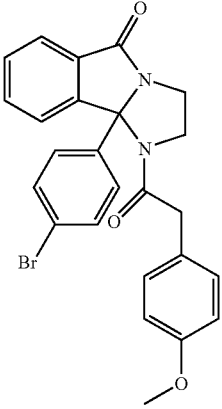 [SMILES: COc1ccc(CC(=O)N2CCN3C(=O)c4ccccc4C23c2ccc(Br)cc2)cc1] | 479 | H |
| 236 | 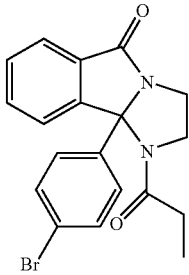 [SMILES: CCC(=O)N1CCN2C(=O)c3ccccc3C12c1ccc(Br)cc1] | 387 | H |
| 237 | 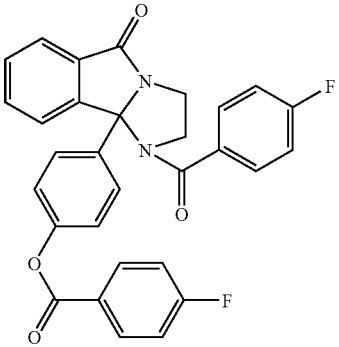 [SMILES: O=C(Oc1ccc(C23c4ccccc4C(=O)N2CCN3C(=O)c2ccc(F)cc2)cc1)c1ccc(F)cc1] | 511 | H |
| 238 | 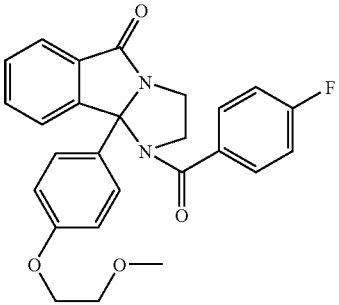 [SMILES: COCCOc1ccc(C23c4ccccc4C(=O)N2CCN3C(=O)c2ccc(F)cc2)cc1] | 447 | L |
| 239 | 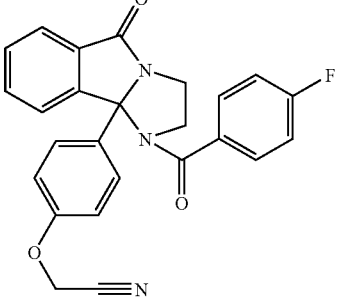 | 428 | L |

TABLE 2-continued

Compounds of the Invention (Formula I where A is Aryl)

| No. | Structure | m/z M + H+ | Mtd |
|---|---|---|---|
| 240 | 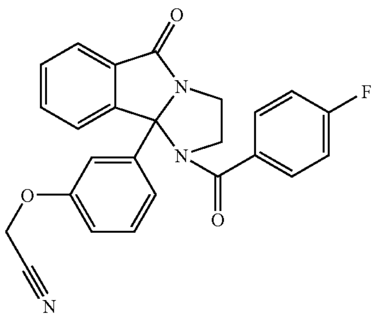 [SMILES: N#CCOc1cccc(C23c4ccccc4C(=O)N2CCN3C(=O)c2ccc(F)cc2)c1] | 428 | L |
| 241 | 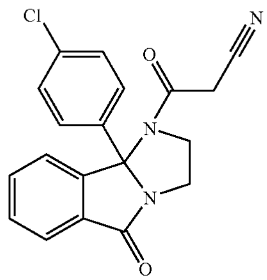 [SMILES: N#CCC(=O)N1CCN2C(=O)c3ccccc3C12c1ccc(Cl)cc1] | 352 | I |
| 242 | 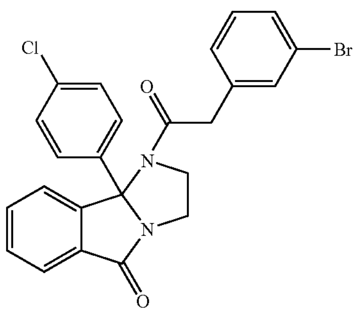 [SMILES: O=C(Cc1cccc(Br)c1)N1CCN2C(=O)c3ccccc3C12c1ccc(Cl)cc1] | 481 | I |
| 243 | 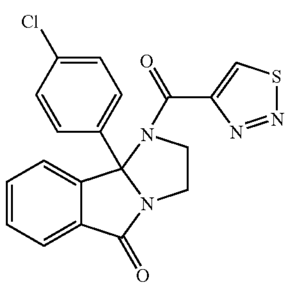 [SMILES: O=C(c1csnn1)N1CCN2C(=O)c3ccccc3C12c1ccc(Cl)cc1] | 397 | I |
| 244 | 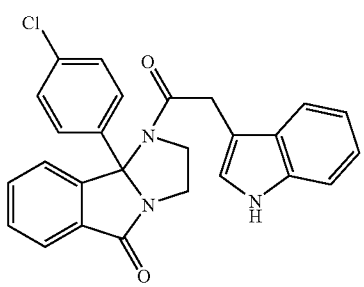 [SMILES: O=C(Cc1c[nH]c2ccccc12)N1CCN2C(=O)c3ccccc3C12c1ccc(Cl)cc1] | 442 | I |
| 245 | 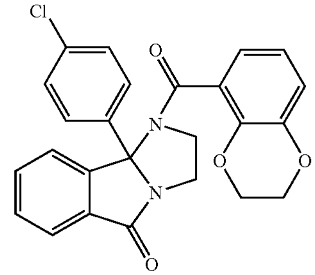 [SMILES: O=C1c2ccccc2C2(c3ccc(Cl)cc3)N1CCN2C(=O)c1cccc2c1OCCO2] | 447 | I |
| 246 | 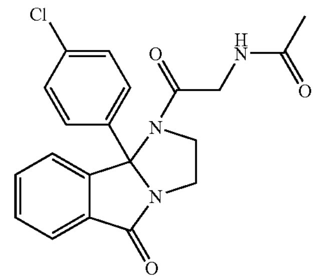 [SMILES: CC(=O)NCC(=O)N1CCN2C(=O)c3ccccc3C12c1ccc(Cl)cc1] | 384 | I |
| 247 | 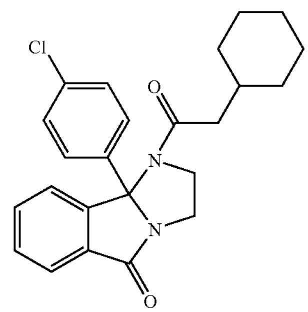 [SMILES: O=C(CC1CCCCC1)N1CCN2C(=O)c3ccccc3C12c1ccc(Cl)cc1] | 409 | I |
| 248 | 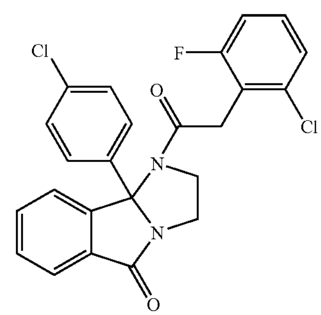 | 455 | I |
| 249 | 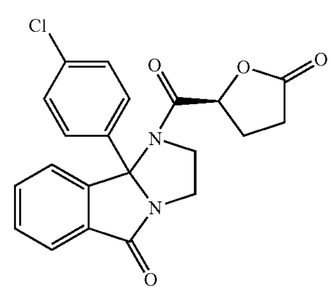 [SMILES: O=C1CC[C@@H](C(=O)N2CCN3C(=O)c4ccccc4C32c2ccc(Cl)cc2)O1] | 397 | I |

TABLE 2-continued

Compounds of the Invention (Formula I where A is Aryl)

| No. | Structure | m/z M+H+ | Mtd |
|---|---|---|---|
| 250 | 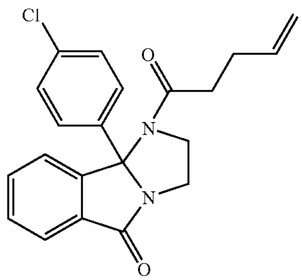 [SMILES: C=CCCC(=O)N1CCN2C(=O)c3ccccc3C12c1ccc(Cl)cc1] | 367 | I |
| 251 | 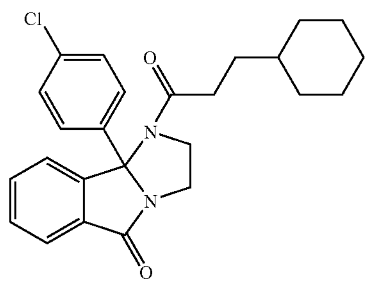 [SMILES: O=C(CCC1CCCCC1)N1CCN2C(=O)c3ccccc3C12c1ccc(Cl)cc1] | 423 | I |
| 252 | 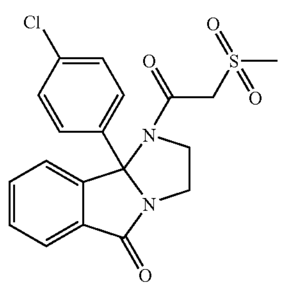 [SMILES: CS(=O)(=O)CC(=O)N1CCN2C(=O)c3ccccc3C12c1ccc(Cl)cc1] | 405 | I |
| 253 | 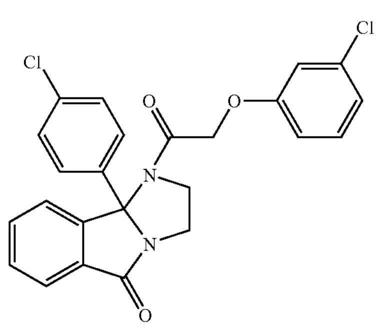 [SMILES: O=C(COc1cccc(Cl)c1)N1CCN2C(=O)c3ccccc3C12c1ccc(Cl)cc1] | 453 | I |
| 254 | | 443 | I |
| 255 | | 451 | I |
| 256 | | 509 | I |
| 257 | | 389 | L |

TABLE 2-continued
Compounds of the Invention (Formula I where A is Aryl)
| No. | Structure | m/z M+H⁺ | Mtd |
|---|---|---|---|
| 258 | 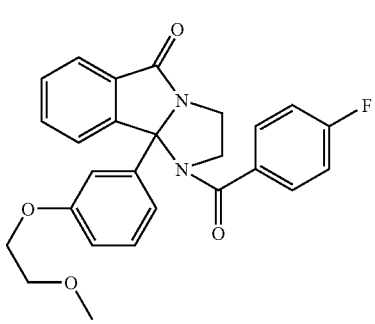 [SMILES: COCCOc1cccc(C23c4ccccc4C(=O)N2CCN3C(=O)c2ccc(F)cc2)c1] | 447 | L |
| 259 | 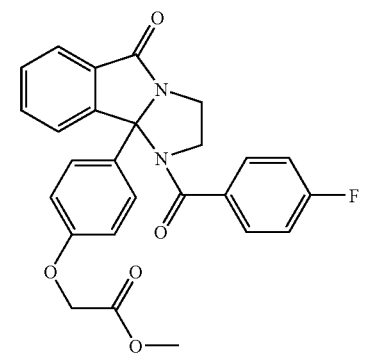 [SMILES: COC(=O)COc1ccc(C23c4ccccc4C(=O)N2CCN3C(=O)c2ccc(F)cc2)cc1] | 461 | L |
| 260 | 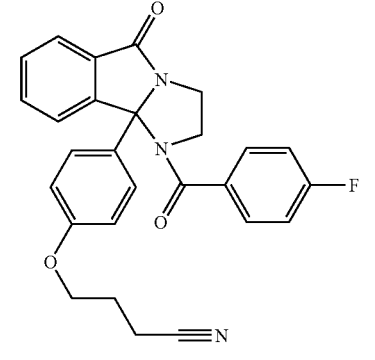 [SMILES: N#CCCCOc1ccc(C23c4ccccc4C(=O)N2CCN3C(=O)c2ccc(F)cc2)cc1] | 456 | L |
| 261 | 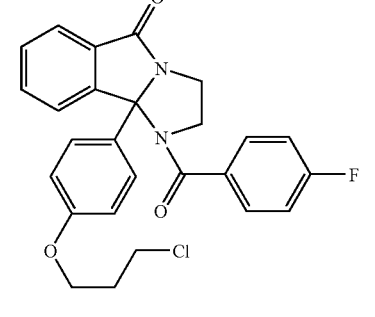 | 465 | L |
| 262 | 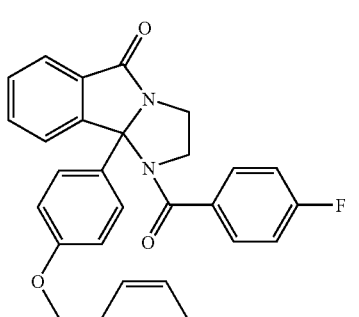 | 479 | L |
| 263 | 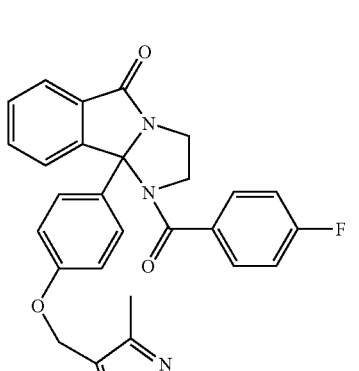 | 498 | L |
| 264 | 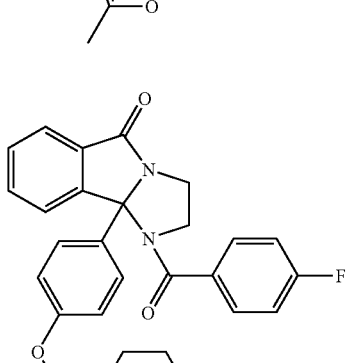 | 479 | L |
| 265 | 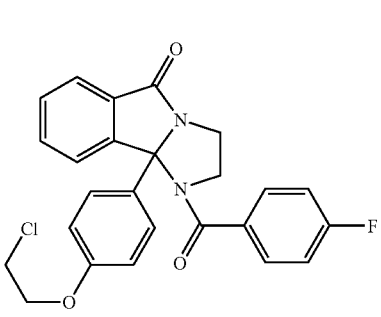 [SMILES: O=C(c1ccc(F)cc1)N1CCN2C(=O)c3ccccc3C12c1ccc(OCCCl)cc1] | 451 | L |

TABLE 2-continued

Compounds of the Invention (Formula I where A is Aryl)

| No. | Structure | m/z M+H⁺ | Mtd |
|---|---|---|---|
| 266 | | 446 | L |
| 267 | | 443 | L |
| 268 | | 445 | L |
| 269 | | 447 | L |
| 270 | 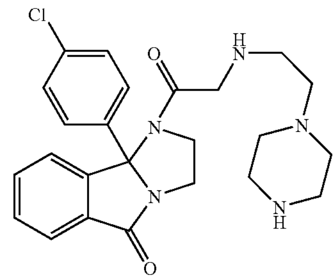 | 454 | M |
| 271 | 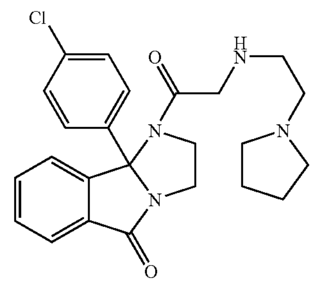 [SMILES: O=C(CNCCN1CCCC1)N1CCN2C(=O)c3ccccc3C12c1ccc(Cl)cc1] | 439 | M |
| 272 | 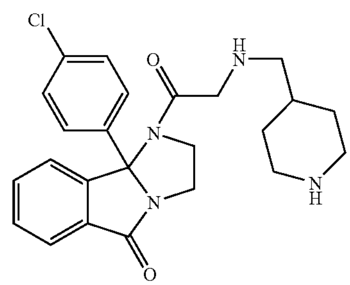 [SMILES: O=C(CNCC1CCNCC1)N1CCN2C(=O)c3ccccc3C12c1ccc(Cl)cc1] | 439 | M |
| 273 | 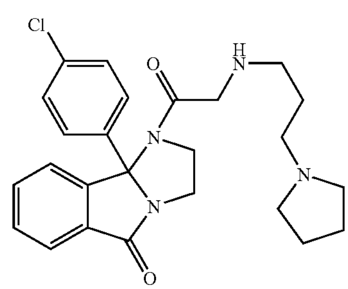 [SMILES: O=C(CNCCCN1CCCC1)N1CCN2C(=O)c3ccccc3C12c1ccc(Cl)cc1] | 453 | M |
| 274 | 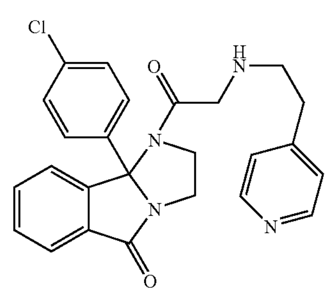 [SMILES: O=C(CNCCc1ccncc1)N1CCN2C(=O)c3ccccc3C12c1ccc(Cl)cc1] | 447 | M |

TABLE 2-continued

Compounds of the Invention (Formula I where A is Aryl)

| No. | Structure | m/z M+H+ | Mtd |
|---|---|---|---|
| 275 | 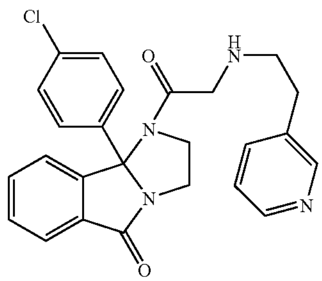 [SMILES: O=C(CNCCc1cccnc1)N1CCN2C(=O)c3ccccc3C12c1ccc(Cl)cc1] | 447 | M |
| 276 | 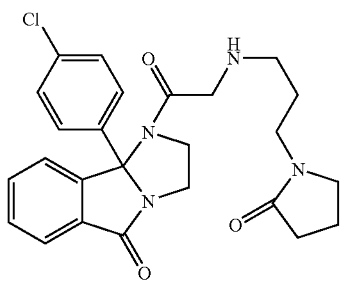 [SMILES: O=C1CCCN1CCCNCC(=O)N1CCN2C(=O)c3ccccc3C12c1ccc(Cl)cc1] | 467 | M |
| 277 | 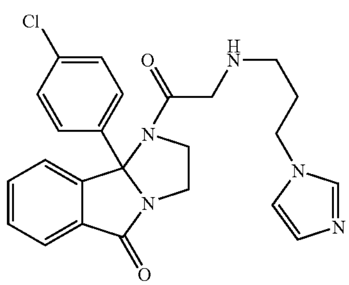 [SMILES: O=C(CNCCCn1ccnc1)N1CCN2C(=O)c3ccccc3C12c1ccc(Cl)cc1] | 450 | M |
| 278 | 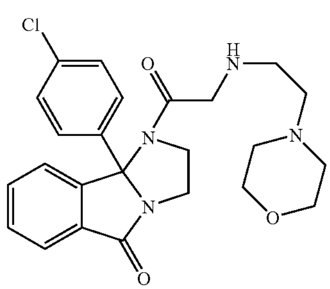 [SMILES: O=C(CNCCN1CCOCC1)N1CCN2C(=O)c3ccccc3C12c1ccc(Cl)cc1] | 455 | M |
| 279 | 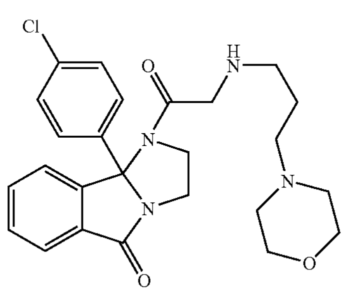 [SMILES: O=C(CNCCCN1CCOCC1)N1CCN2C(=O)c3ccccc3C12c1ccc(Cl)cc1] | 469 | M |
| 280 | | 447 | M |
| 281 | | 433 | M |
| 282 | | 490 | M |
| 283 | | 433 | M |

TABLE 2-continued

Compounds of the Invention (Formula I where A is Aryl)

| No. | Structure | m/z M+H⁺ | Mtd |
|---|---|---|---|
| 284 | 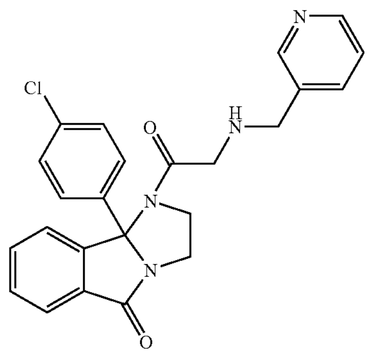 [SMILES: O=C(CNCc1cccnc1)N1CCN2C(=O)c3ccccc3C12c1ccc(Cl)cc1] | 433 | M |
| 285 | 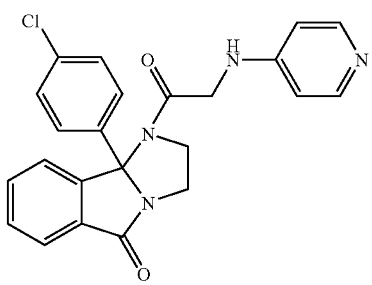 [SMILES: O=C(CNc1ccncc1)N1CCN2C(=O)c3ccccc3C12c1ccc(Cl)cc1] | 419 | M |
| 286 | 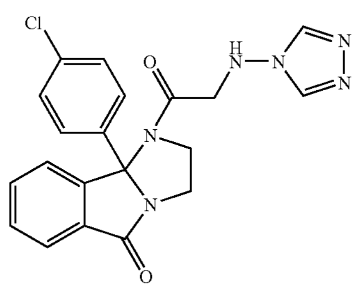 [SMILES: O=C(CNn1cnnc1)N1CCN2C(=O)c3ccccc3C12c1ccc(Cl)cc1] | 409 | M |
| 287 | 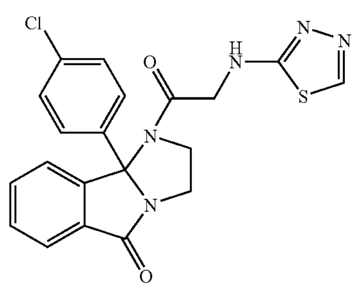 [SMILES: O=C(CNc1nncs1)N1CCN2C(=O)c3ccccc3C12c1ccc(Cl)cc1] | 426 | M |
| 288 | 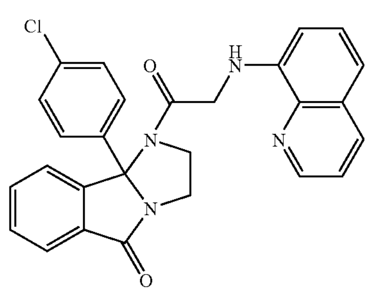 [SMILES: O=C(CNc1cccc2cccnc12)N1CCN2C(=O)c3ccccc3C12c1ccc(Cl)cc1] | 469 | M |
| 289 | | 425 | M |
| 290 | | 419 | M |
| 291 | | 419 | M |
| 292 | | 420 | M |
| 293 | | 409 | M |

TABLE 2-continued

Compounds of the Invention (Formula I where A is Aryl)

| No. | Structure | m/z M+H+ | Mtd |
|---|---|---|---|
| 294 | 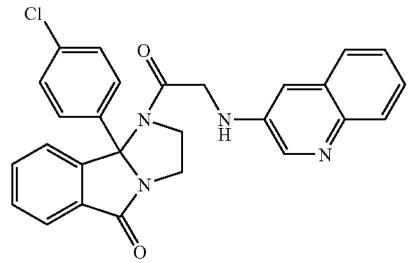 [SMILES: O=C(CNc1cnc2ccccc2c1)N1CCN2C(=O)c3ccccc3C12c1ccc(Cl)cc1] | 469 | M |
| 295 | 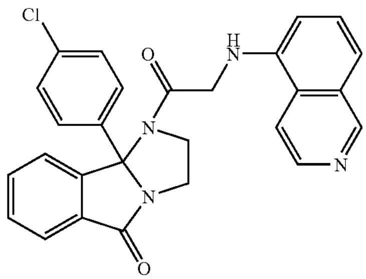 [SMILES: O=C(CNc1cccc2cnccc12)N1CCN2C(=O)c3ccccc3C12c1ccc(Cl)cc1] | 469 | M |
| 296 | 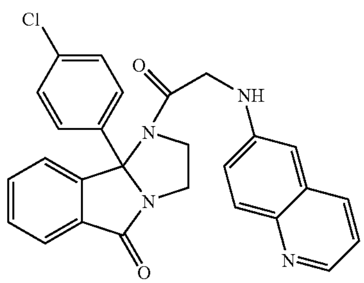 [SMILES: O=C(CNc1ccc2ncccc2c1)N1CCN2C(=O)c3ccccc3C12c1ccc(Cl)cc1] | 469 | M |
| 297 | 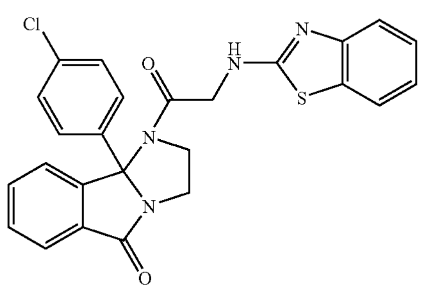 [SMILES: O=C(CNc1nc2ccccc2s1)N1CCN2C(=O)c3ccccc3C12c1ccc(Cl)cc1] | 475 | M |
| 298 | 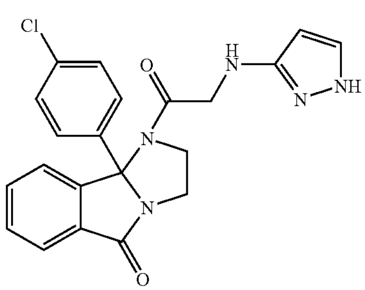 [SMILES: O=C(CNc1cc[nH]n1)N1CCN2C(=O)c3ccccc3C12c1ccc(Cl)cc1] | 408 | M |
| 299 | | 436 | M |
| 300 | | 475 | M |
| 301 | | 492 | M |
| 302 | | 425 | M |
| 303 | | 437 | M |

TABLE 2-continued
Compounds of the Invention (Formula I where A is Aryl)
| No. | Structure | m/z M + H⁺ | Mtd |
|---|---|---|---|
| 304 | 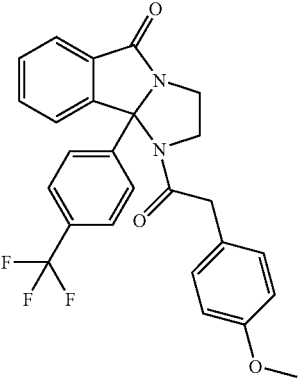 [SMILES: COc1ccc(CC(=O)N2CCN3C(=O)c4ccccc4C23c2ccc(C(F)(F)F)cc2)cc1] | 467 | H |
| 305 | 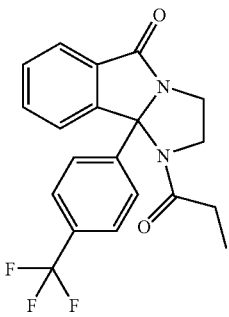 [SMILES: CCC(=O)N1CCN2C(=O)c3ccccc3C12c1ccc(C(F)(F)F)cc1] | 375 | H |
| 306 | 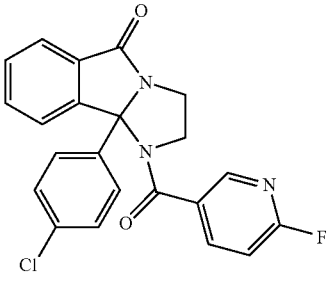 [SMILES: O=C(c1ccc(F)nc1)N1CCN2C(=O)c3ccccc3C12c1ccc(Cl)cc1] | 408 | H |
| 307 | 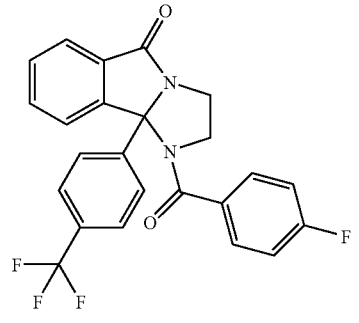 [SMILES: O=C(c1ccc(F)cc1)N1CCN2C(=O)c3ccccc3C12c1ccc(C(F)(F)F)cc1] | 441 | H |
| 308 | 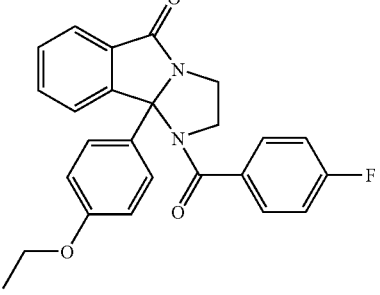 | 417 | L |
| 309 | 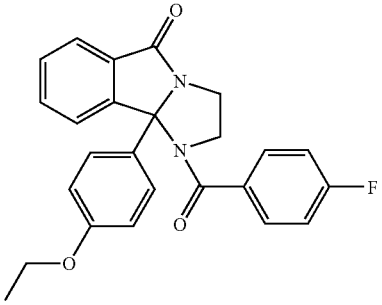 [SMILES: CCOc1ccc(C23c4ccccc4C(=O)N2CCN3C(=O)c2ccc(F)cc2)cc1] | 459 | L |
| 310 | 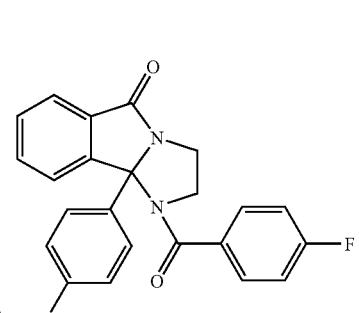 | 431 | L |
| 311 | 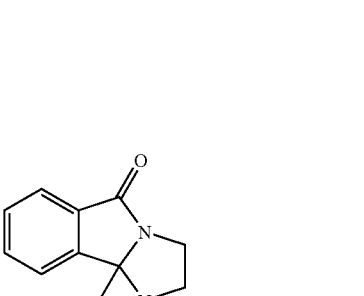 | 431 | L |

TABLE 2-continued

Compounds of the Invention (Formula I where A is Aryl)

| No. | Structure | m/z M+H⁺ | Mtd |
|---|---|---|---|
| 312 | 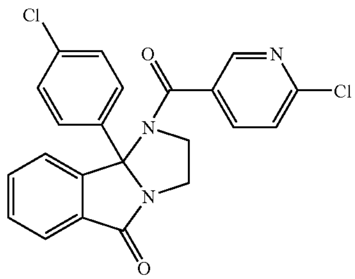 [SMILES: O=C(c1ccc(Cl)nc1)N1CCN2C(=O)c3ccccc3C12c1ccc(Cl)cc1] | 424 | H |
| 313 | 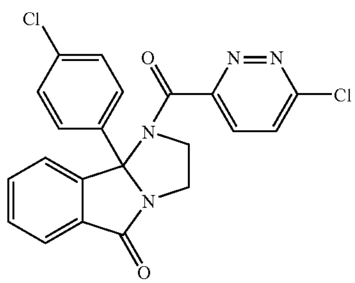 [SMILES: O=C(c1ccc(Cl)nn1)N1CCN2C(=O)c3ccccc3C12c1ccc(Cl)cc1] | 425 | H |
| 314 | 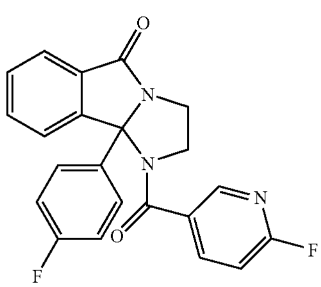 [SMILES: O=C(c1ccc(F)nc1)N1CCN2C(=O)c3ccccc3C12c1ccc(F)cc1] | 392 | H |
| 315 | 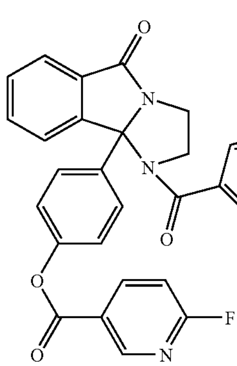 | 513 | H |
| 316 | 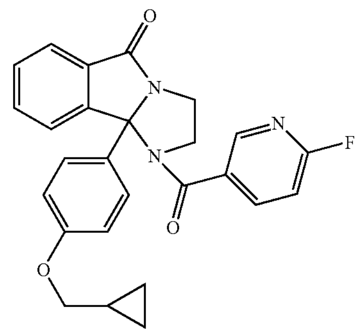 [SMILES: O=C(c1ccc(F)nc1)N1CCN2C(=O)c3ccccc3C12c1ccc(OCC2CC2)cc1] | 444 | H |
| 317 | 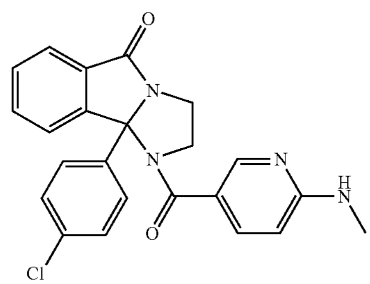 [SMILES: CNc1ccc(C(=O)N2CCN3C(=O)c4ccccc4C23c2ccc(Cl)cc2)cn1] | 419 | K |
| 318 | 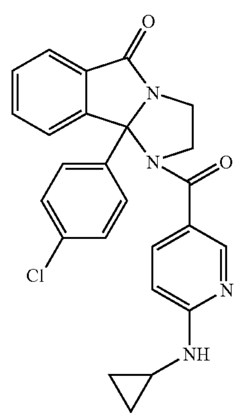 [SMILES: O=C(c1ccc(NC2CC2)nc1)N1CCN2C(=O)c3ccccc3C12c1ccc(Cl)cc1] | 445 | K |
| 319 | 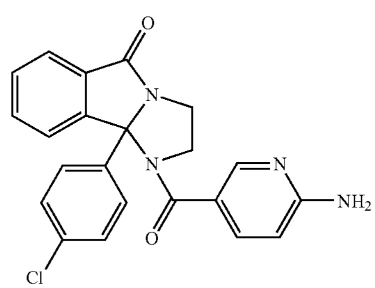 [SMILES: Nc1ccc(C(=O)N2CCN3C(=O)c4ccccc4C23c2ccc(Cl)cc2)cn1] | 405 | K |

TABLE 2-continued

Compounds of the Invention (Formula I where A is Aryl)

| No. | Structure | m/z M+H+ | Mtd |
|---|---|---|---|
| 320 | 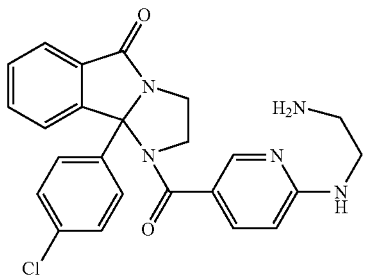 [SMILES: NCCNc1ccc(C(=O)N2CCN3C(=O)c4ccccc4C23c2ccc(Cl)cc2)cn1] | 448 | K |
| 321 | 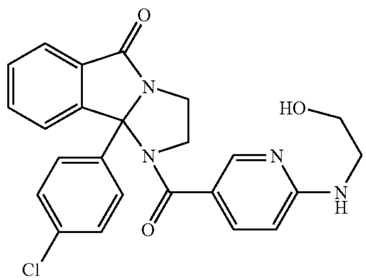 [SMILES: O=C(c1ccc(NCCO)nc1)N1CCN2C(=O)c3ccccc3C12c1ccc(Cl)cc1] | 449 | K |
| 322 | 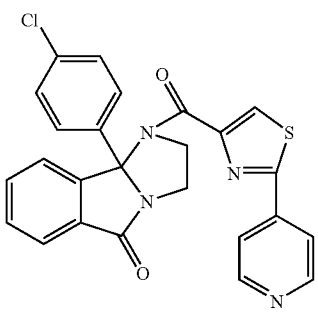 [SMILES: O=C(c1csc(-c2ccncc2)n1)N1CCN2C(=O)c3ccccc3C12c1ccc(Cl)cc1] | 473 | H |
| 323 | 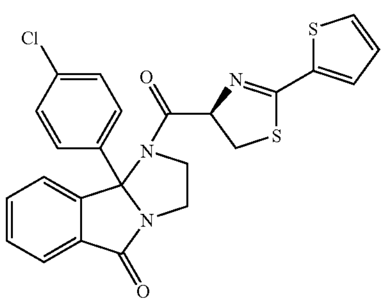 [SMILES: O=C1c2ccccc2C2(c3ccc(Cl)cc3)N1CCN2C(=O)[C@@H]1CSC(c2cccs2)=N1] | 480 | H |
| 324 | 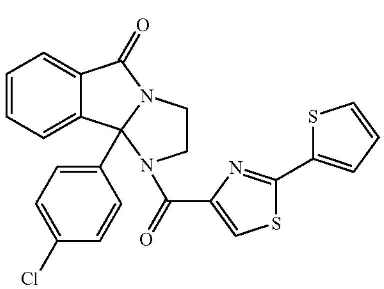 [SMILES: O=C(c1csc(-c2cccs2)n1)N1CCN2C(=O)c3ccccc3C12c1ccc(Cl)cc1] | 478 | H |
| 325 | | 407 | H |
| 326 | | 379 | H |
| 327 | | 395 | H |
| 328 | | 429 | H |
| 329 | | 439 | H |

TABLE 2-continued

Compounds of the Invention (Formula I where A is Aryl)

| No. | Structure | m/z M+H⁺ | Mtd |
|---|---|---|---|
| 330 | 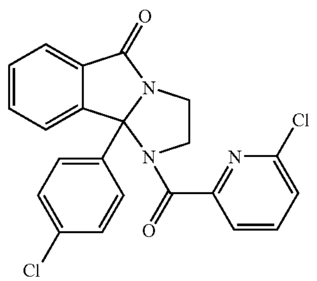 [SMILES: O=C(c1cccc(Cl)n1)N1CCN2C(=O)c3ccccc3C12c1ccc(Cl)cc1] | 424 | H |
| 331 | 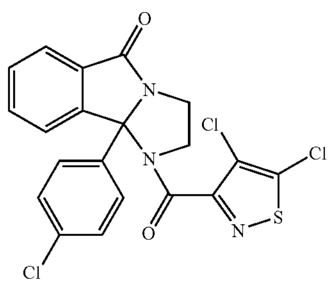 [SMILES: O=C1c2ccccc2C2(c3ccc(Cl)cc3)N1CCN2C(=O)c1nsc(Cl)c1Cl] | 466 | H |
| 332 | 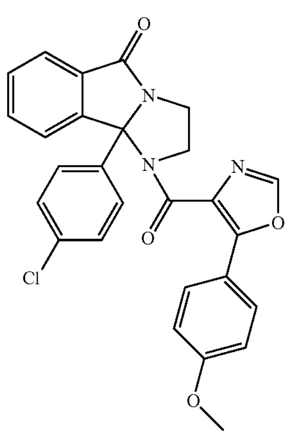 [SMILES: COc1ccc(-c2ocnc2C(=O)N2CCN3C(=O)c4ccccc4C32c2ccc(Cl)cc2)cc1] | 486 | H |
| 333 | 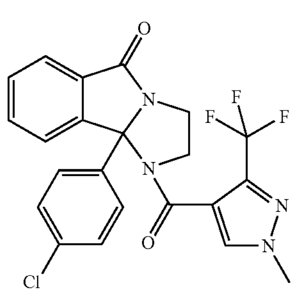 [SMILES: Cn1cc(C(=O)N2CCN3C(=O)c4ccccc4C32c2ccc(Cl)cc2)c(C(F)(F)F)n1] | 461 | H |
| 334 | 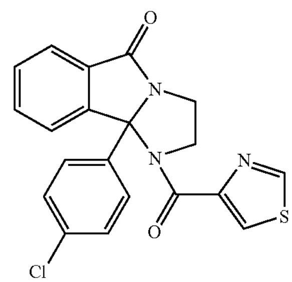 [SMILES: O=C(c1cscn1)N1CCN2C(=O)c3ccccc3C12c1ccc(Cl)cc1] | 396 | H |
| 335 | 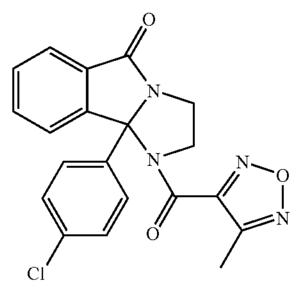 [SMILES: Cc1nonc1C(=O)N1CCN2C(=O)c3ccccc3C21c1ccc(Cl)cc1] | 395 | H |
| 503 | 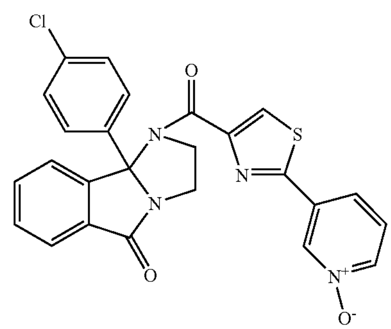 [SMILES: O=C(c1csc(-c2ccc[n+]([O-])c2)n1)N1CCN2C(=O)c3ccccc3C12c1ccc(Cl)cc1] | 489 | J |

TABLE 3

Compounds of the Invention (Formula I where A is Heteroaryl)

| No. | Structure | m/z M+H⁺ | Mtd |
|---|---|---|---|
| 63 | 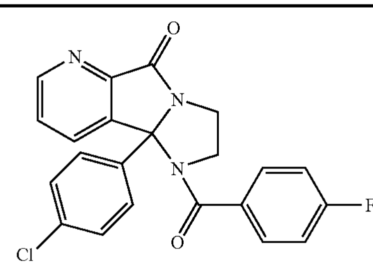 | 408 | C |

TABLE 3-continued

Compounds of the Invention (Formula I where A is Heteroaryl)

| No. | Structure | m/z M+H⁺ | Mtd |
|---|---|---|---|
| 78 | 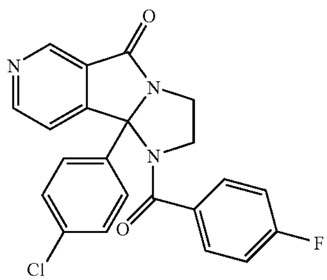 [SMILES: O=C(c1ccc(F)cc1)N1CCN2C(=O)c3cnccc3C12c1ccc(Cl)cc1] | 408 | C |
| 123 | 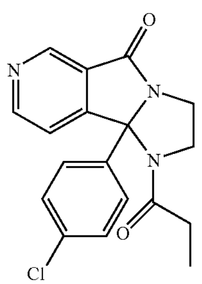 [SMILES: CCC(=O)N1CCN2C(=O)c3cnccc3C12c1ccc(Cl)cc1] | 342 | H |
| 336 | 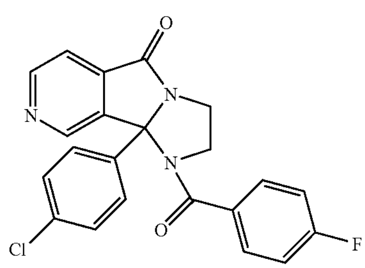 [SMILES: O=C(c1ccc(F)cc1)N1CCN2C(=O)c3ccncc3C12c1ccc(Cl)cc1] | 408 | C |
| 337 | 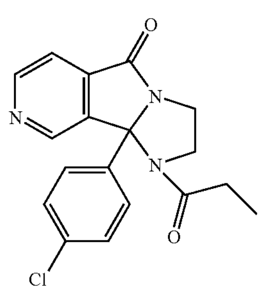 [SMILES: CCC(=O)N1CCN2C(=O)c3ccncc3C12c1ccc(Cl)cc1] | 342 | H |
| 338 | 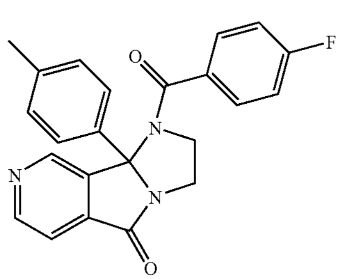 [SMILES: Cc1ccc(C23c4cnccc4C(=O)N2CCN3C(=O)c2ccc(F)cc2)cc1] | 388 | H |
| 339 | | 322 | H |
| 340 | | 409 | H |
| 341 | | 435 | H |
| 342 | | 343 | H |

TABLE 3-continued

Compounds of the Invention (Formula I where A is Heteroaryl)

| No. | Structure | m/z M + H⁺ | Mtd |
|---|---|---|---|
| 343 | 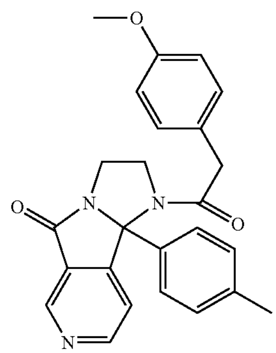 [SMILES: COc1ccc(CC(=O)N2CCN3C(=O)c4cnccc4C23c2ccc(C)cc2)cc1] | 414 | H |
| 344 | 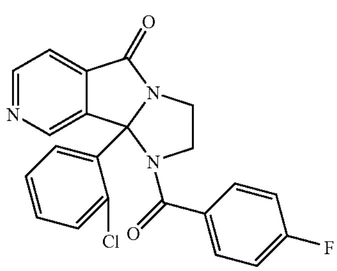 [SMILES: O=C(c1ccc(F)cc1)N1CCN2C(=O)c3ccncc3C12c1ccccc1Cl] | 408 | H |
| 345 | 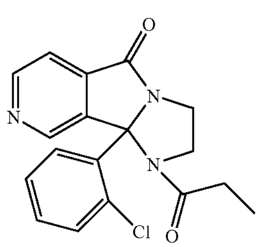 [SMILES: CCC(=O)N1CCN2C(=O)c3ccncc3C12c1ccccc1Cl] | 342 | H |
| 346 | 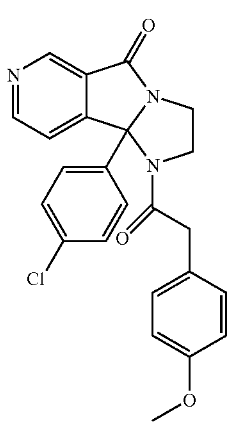 [SMILES: COc1ccc(CC(=O)N2CCN3C(=O)c4cnccc4C23c2ccc(Cl)cc2)cc1] | 434 | H |
| 347 | | 442 | H |
| 348 | | 468 | H |
| 349 | | 468 | H |
| 350 | | 376 | H |

TABLE 3-continued

Compounds of the Invention (Formula I where A is Heteroaryl)

| No. | Structure | m/z M+H⁺ | Mtd |
|---|---|---|---|
| 351 | 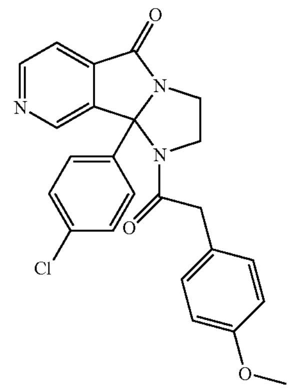 [SMILES: COc1ccc(CC(=O)N2CCN3C(=O)c4ccncc4C23c2ccc(Cl)cc2)cc1] | 434 | H |
| 352 | 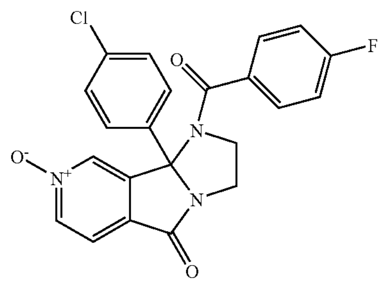 [SMILES: O=C(c1ccc(F)cc1)N1CCN2C(=O)c3cc[n+]([O-])cc3C12c1ccc(Cl)cc1] | 424 | J |
| 353 | 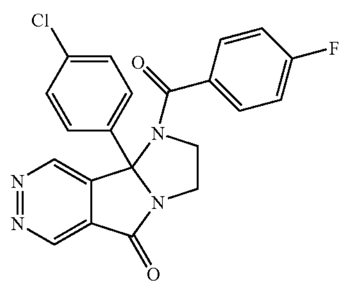 [SMILES: O=C(c1ccc(F)cc1)N1CCN2C(=O)c3cnncc3C12c1ccc(Cl)cc1] | 409 | H |
| 354 | 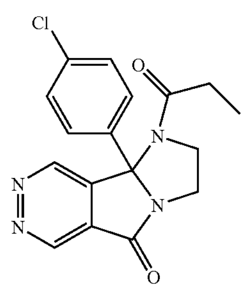 [SMILES: CCC(=O)N1CCN2C(=O)c3cnncc3C12c1ccc(Cl)cc1] | 343 | H |
| 355 | 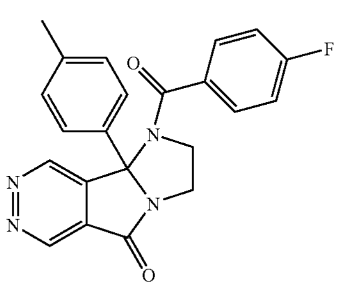 [SMILES: Cc1ccc(C23c4cnncc4C(=O)N2CCN3C(=O)c2ccc(F)cc2)cc1] | 389 | H |
| 356 | 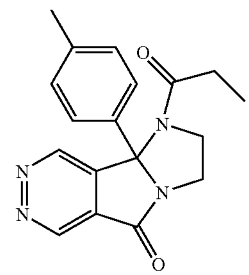 [SMILES: CCC(=O)N1CCN2C(=O)c3cnncc3C12c1ccc(C)cc1] | 323 | H |
| 357 | 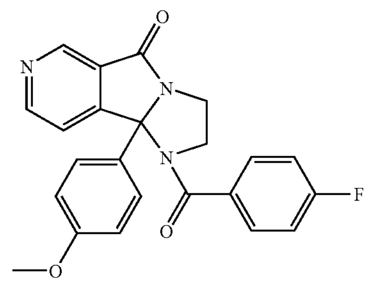 [SMILES: COc1ccc(C23c4ccncc4C(=O)N2CCN3C(=O)c2ccc(F)cc2)cc1] | 404 | H |
| 358 | 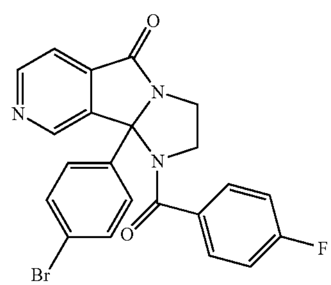 [SMILES: O=C(c1ccc(F)cc1)N1CCN2C(=O)c3ccncc3C12c1ccc(Br)cc1] | 452 | H |
| 359 | 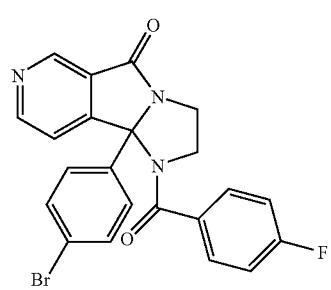 [SMILES: O=C(c1ccc(F)cc1)N1CCN2C(=O)c3cnccc3C12c1ccc(Br)cc1] | 454 | H |
| 360 | 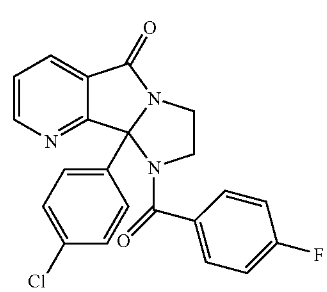 [SMILES: O=C(c1ccc(F)cc1)N1CCN2C(=O)c3cccnc3C12c1ccc(Cl)cc1] | 408 | H |

TABLE 3-continued

Compounds of the Invention (Formula I where A is Heteroaryl)

| No. | Structure | m/z M+H⁺ | Mtd |
|---|---|---|---|
| 361 | 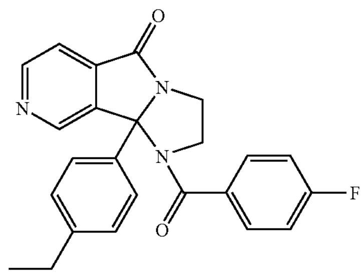 [SMILES: CCc1ccc(C23c4cnccc4C(=O)N2CCN3C(=O)c2ccc(F)cc2)cc1] | 402 | H |
| 362 | 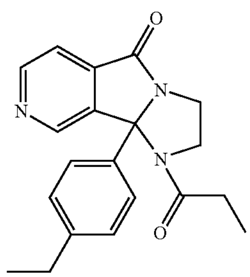 [SMILES: CCC(=O)N1CCN2C(=O)c3ccncc3C12c1ccc(CC)cc1] | 336 | H |
| 363 | 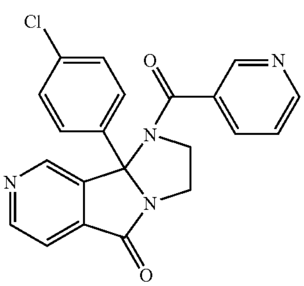 [SMILES: O=C(c1cccnc1)N1CCN2C(=O)c3ccncc3C12c1ccc(Cl)cc1] | 391 | H |
| 364 | 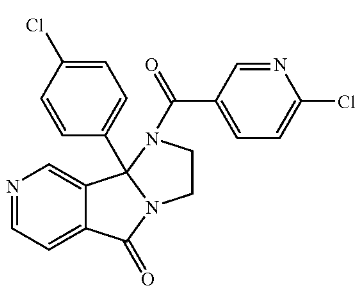 [SMILES: O=C(c1ccc(Cl)nc1)N1CCN2C(=O)c3ccncc3C12c1ccc(Cl)cc1] | 425 | H |
| 365 | 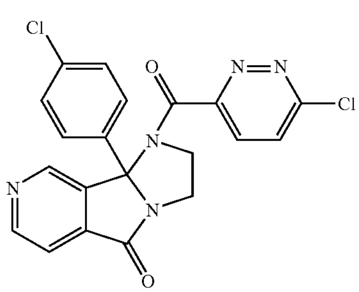 [SMILES: O=C(c1ccc(Cl)nn1)N1CCN2C(=O)c3ccncc3C12c1ccc(Cl)cc1] | 426 | H |
| 366 | | 455 | H |
| 367 | | 455 | H |
| 368 | | 409 | H |
| 369 | | 409 | H |
| 370 | | 409 | H |

TABLE 3-continued

Compounds of the Invention (Formula I where A is Heteroaryl)

| No. | Structure | m/z M + H⁺ | Mtd |
|---|---|---|---|
| 371 | 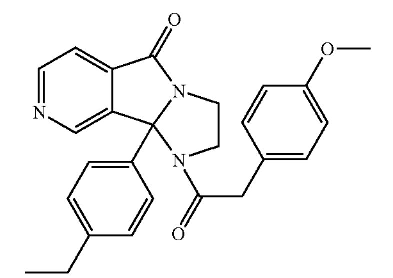 [SMILES: CCc1ccc(C23c4cnccc4C(=O)N2CCN3C(=O)Cc2ccc(OC)cc2)cc1] | 428 | H |
| 372 | 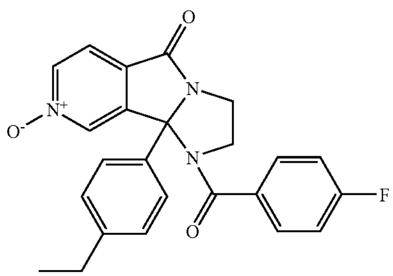 [SMILES: CCc1ccc(C23c4c[n+]([O-])ccc4C(=O)N2CCN3C(=O)c2ccc(F)cc2)cc1] | 418 | J |
| 373 | 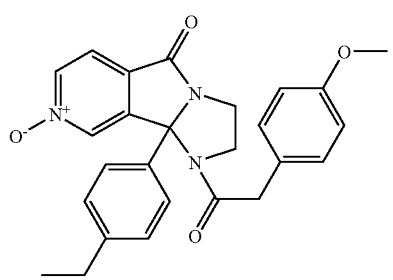 [SMILES: CCc1ccc(C23c4c[n+]([O-])ccc4C(=O)N2CCN3C(=O)Cc2ccc(OC)cc2)cc1] | 444 | J |
| 374 | 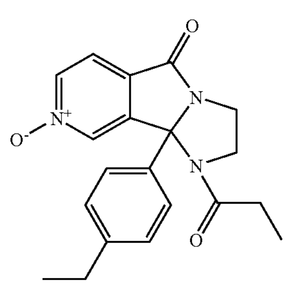 [SMILES: CCC(=O)N1CCN2C(=O)c3cc[n+]([O-])cc3C12c1ccc(CC)cc1] | 352 | J |
| 375 | 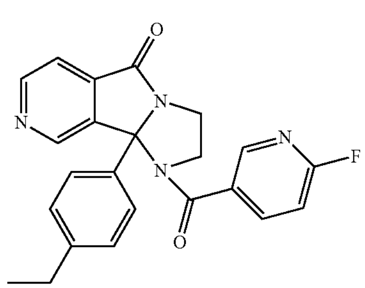 [SMILES: CCc1ccc(C23c4cnccc4C(=O)N2CCN3C(=O)c2ccc(F)nc2)cc1] | 403 | H |
| 376 | | 483 | H |
| 377 | | 479 | H |
| 378 | | 450 | H |
| 379 | | 446 | H |
| 380 | | 441 | H |

TABLE 3-continued

Compounds of the Invention (Formula I where A is Heteroaryl)

| No. | Structure | m/z M+H+ | Mtd |
|---|---|---|---|
| 381 | 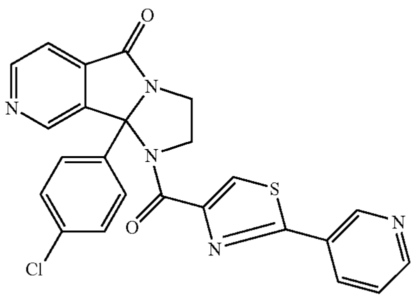 [SMILES: O=C(c1csc(-c2cccnc2)n1)N1CCN2C(=O)c3ccncc3C12c1ccc(Cl)cc1] | 474 | H |
| 382 | 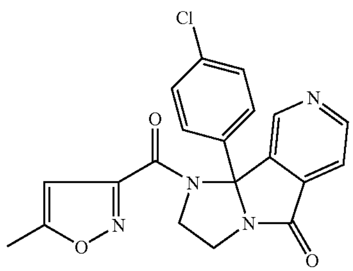 [SMILES: Cc1cc(C(=O)N2CCN3C(=O)c4ccncc4C23c2ccc(Cl)cc2)no1] | 395 | H |
| 383 | 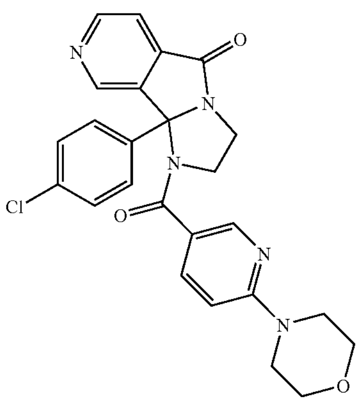 [SMILES: O=C(c1ccc(N2CCOCC2)nc1)N1CCN2C(=O)c3ccncc3C12c1ccc(Cl)cc1] | 476 | H |
| 384 | 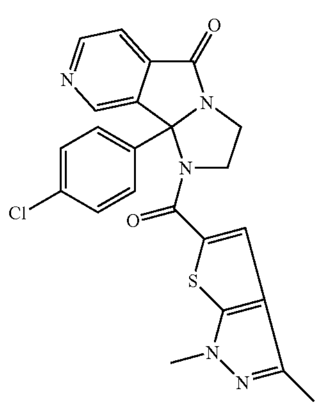 [SMILES: Cc1nn(C)c2sc(C(=O)N3CCN4C(=O)c5ccncc5C34c3ccc(Cl)cc3)cc12] | 464 | H |
| 385 | 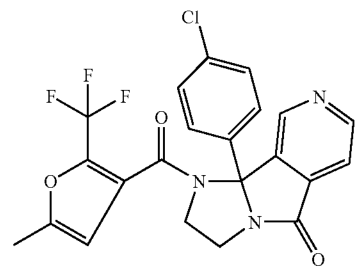 [SMILES: Cc1cc(C(=O)N2CCN3C(=O)c4ccncc4C32c2ccc(Cl)cc2)c(C(F)(F)F)o1] | 462 | H |
| 386 | 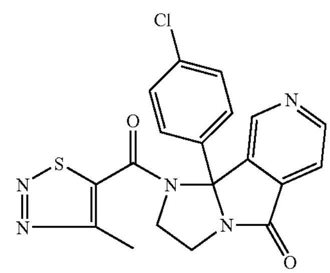 [SMILES: Cc1nnsc1C(=O)N1CCN2C(=O)c3ccncc3C21c1ccc(Cl)cc1] | 412 | H |
| 387 | 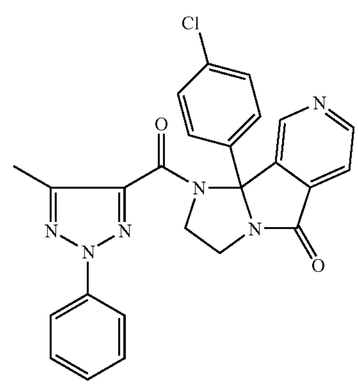 [SMILES: Cc1nn(-c2ccccc2)nc1C(=O)N1CCN2C(=O)c3ccncc3C21c1ccc(Cl)cc1] | 471 | H |
| 388 | 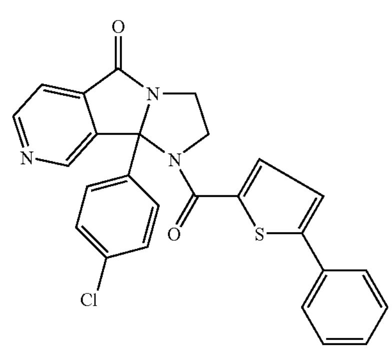 [SMILES: O=C(c1ccc(-c2ccccc2)s1)N1CCN2C(=O)c3ccncc3C12c1ccc(Cl)cc1] | 472 | H |

TABLE 3-continued

Compounds of the Invention (Formula I where A is Heteroaryl)

| No. | Structure | m/z M+H+ | Mtd |
|---|---|---|---|
| 389 | 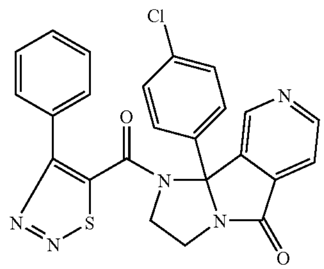 [SMILES: O=C1c2ccncc2C2(c3ccc(Cl)cc3)N1CCN2C(=O)c1snnc1-c1ccccc1] | 474 | H |
| 390 | 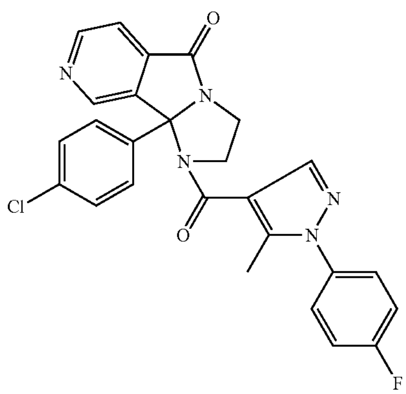 [SMILES: Cc1c(C(=O)N2CCN3C(=O)c4ccncc4C32c2ccc(Cl)cc2)cnn1-c1ccc(F)cc1] | 488 | H |
| 391 | 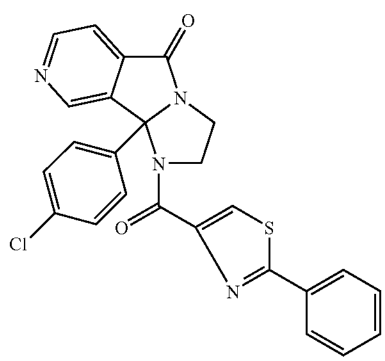 [SMILES: O=C(c1csc(-c2ccccc2)n1)N1CCN2C(=O)c3ccncc3C12c1ccc(Cl)cc1] | 473 | H |
| 392 | 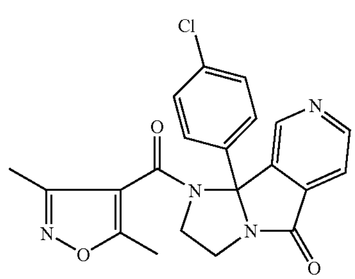 [SMILES: Cc1noc(C)c1C(=O)N1CCN2C(=O)c3ccncc3C21c1ccc(Cl)cc1] | 409 | H |
| 393 | | | H |
| 394 | | 470 | H |
| 395 | | 517 | H |
| 396 | | 501 | H |

TABLE 3-continued

Compounds of the Invention (Formula I where A is Heteroaryl)

| No. | Structure | m/z M+H⁺ | Mtd |
|---|---|---|---|
| 397 | 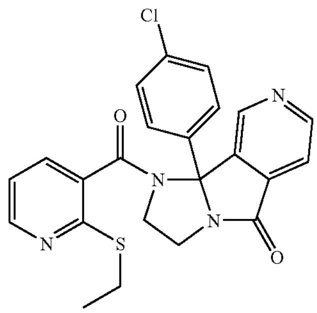 [SMILES: CCSc1ncccc1C(=O)N1CCN2C(=O)c3ccncc3C21c1ccc(Cl)cc1] | 451 | H |
| 398 | 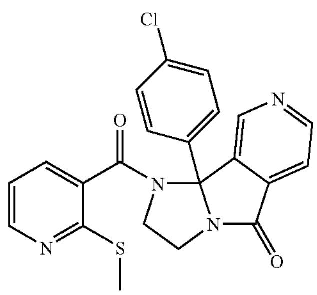 [SMILES: CSc1ncccc1C(=O)N1CCN2C(=O)c3ccncc3C21c1ccc(Cl)cc1] | 437 | H |
| 399 | 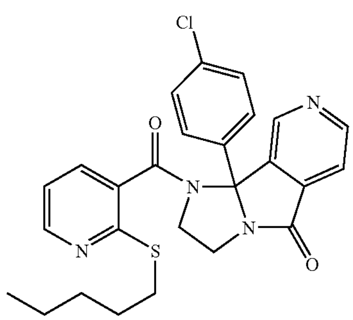 [SMILES: CCCCCSc1ncccc1C(=O)N1CCN2C(=O)c3ccncc3C21c1ccc(Cl)cc1] | 493 | H |
| 400 | 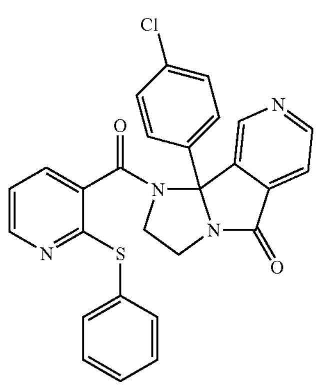 [SMILES: O=C1c2ccncc2C2(c3ccc(Cl)cc3)N1CCN2C(=O)c1cccnc1Sc1ccccc1] | 499 | H |
| 401 | | 465 | H |
| 402 | | 513 | H |
| 403 | | 425 | H |
| 404 | | 483 | H |

TABLE 3-continued

Compounds of the Invention (Formula I where A is Heteroaryl)

| No. | Structure | m/z M+H⁺ | Mtd |
|---|---|---|---|
| 405 | 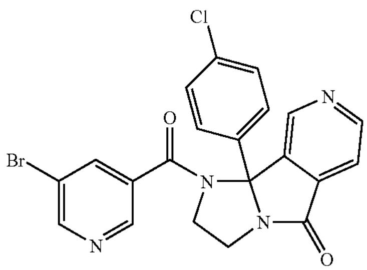 [SMILES: O=C(c1cncc(Br)c1)N1CCN2C(=O)c3ccncc3C12c1ccc(Cl)cc1] | 471 | H |
| 406 | 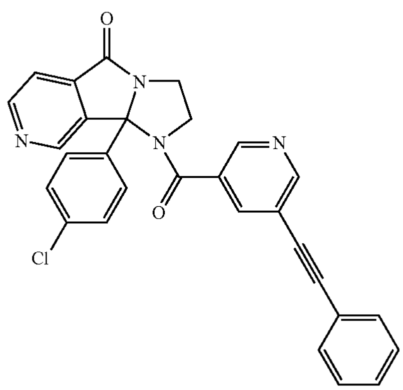 [SMILES: O=C(c1cncc(C#Cc2ccccc2)c1)N1CCN2C(=O)c3ccncc3C12c1ccc(Cl)cc1] | 491 | H |
| 407 | 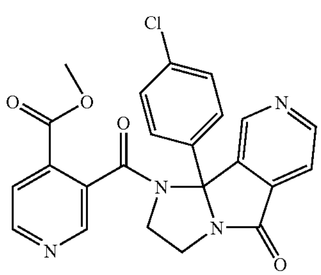 [SMILES: COC(=O)c1ccncc1C(=O)N1CCN2C(=O)c3ccncc3C12c1ccc(Cl)cc1] | 449 | H |
| 408 | 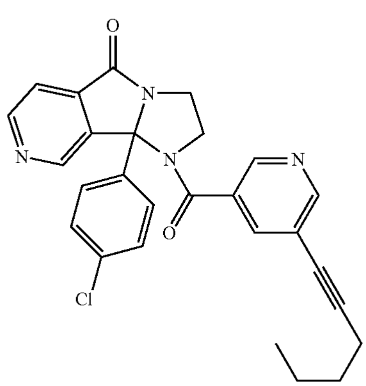 [SMILES: CCCCC#Cc1cncc(C(=O)N2CCN3C(=O)c4ccncc4C23c2ccc(Cl)cc2)c1] | 471 | H |
| 409 | | 473 | H |
| 410 | | 489 | H |
| 411 | | 493 | H |
| 412 | | 408 | H |

TABLE 3-continued
Compounds of the Invention (Formula I where A is Heteroaryl)
| No. | Structure | m/z M+H+ | Mtd |
|---|---|---|---|
| 413 | 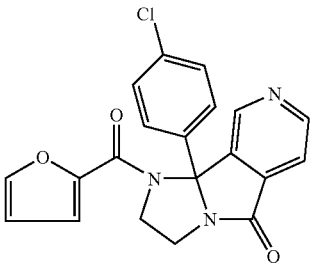 [SMILES: O=C(c1ccco1)N1CCN2C(=O)c3ccncc3C12c1ccc(Cl)cc1] | 380 | H |
| 414 | 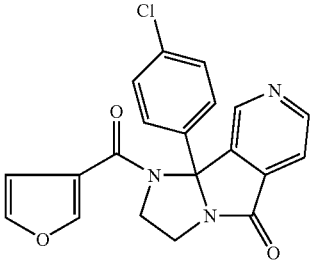 [SMILES: O=C(c1ccoc1)N1CCN2C(=O)c3ccncc3C12c1ccc(Cl)cc1] | 380 | H |
| 415 | 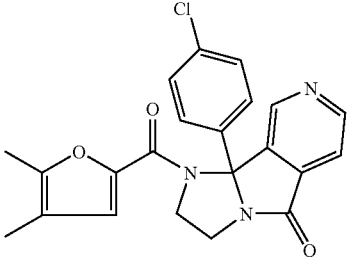 [SMILES: Cc1cc(C(=O)N2CCN3C(=O)c4ccncc4C23c2ccc(Cl)cc2)oc1C] | 408 | H |
| 416 | 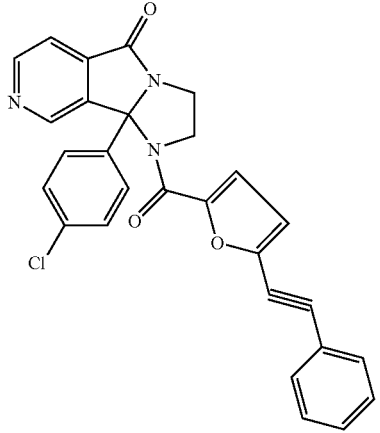 [SMILES: O=C(c1ccc(C#Cc2ccccc2)o1)N1CCN2C(=O)c3ccncc3C12c1ccc(Cl)cc1] | 480 | H |
| 417 | 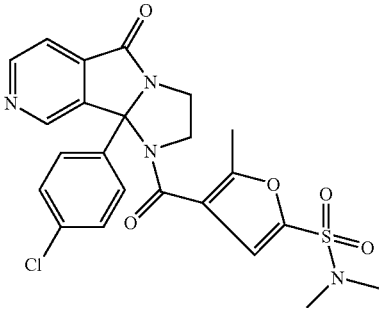 [SMILES: Cc1oc(S(=O)(=O)N(C)C)cc1C(=O)N1CCN2C(=O)c3ccncc3C21c1ccc(Cl)cc1] | 501 | H |
| 418 | 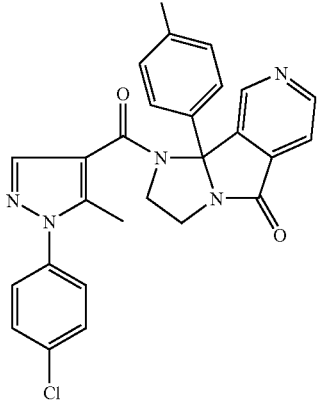 | 504 | H |
| 419 | 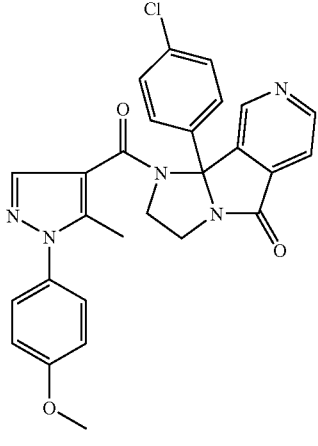 [SMILES: COc1ccc(-n2ncc(C(=O)N3CCN4C(=O)c5ccncc5C43c3ccc(Cl)cc3)c2C)cc1] | 500 | H |
| 420 | 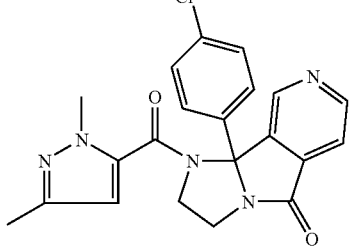 | 408 | H |

TABLE 3-continued

Compounds of the Invention (Formula I where A is Heteroaryl)

| No. | Structure | m/z M+H+ | Mtd |
|---|---|---|---|
| 421 | 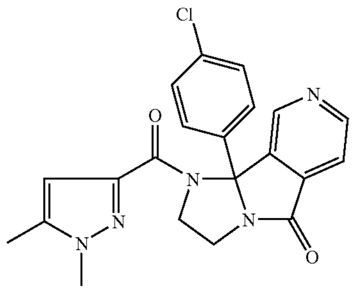 [SMILES: Cc1cc(C(=O)N2CCN3C(=O)c4ccncc4C23c2ccc(Cl)cc2)nn1C] | 408 | H |
| 422 | 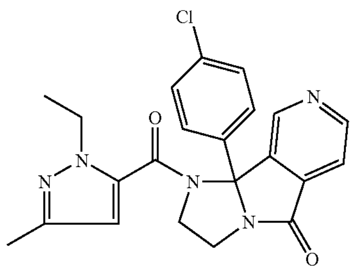 [SMILES: CCn1nc(C)cc1C(=O)N1CCN2C(=O)c3ccncc3C21c1ccc(Cl)cc1] | 422 | H |
| 423 | 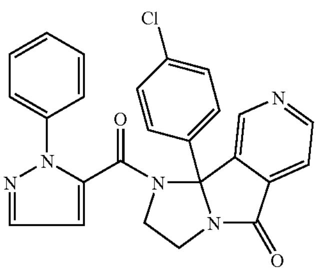 [SMILES: O=C1c2ccncc2C2(c3ccc(Cl)cc3)N1CCN2C(=O)c1ccnn1-c1ccccc1] | 456 | H |
| 424 | 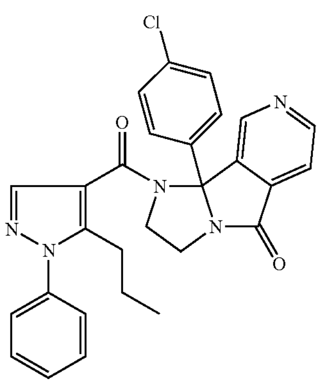 [SMILES: CCCc1c(C(=O)N2CCN3C(=O)c4ccncc4C32c2ccc(Cl)cc2)cnn1-c1ccccc1] | 498 | H |
| 425 | 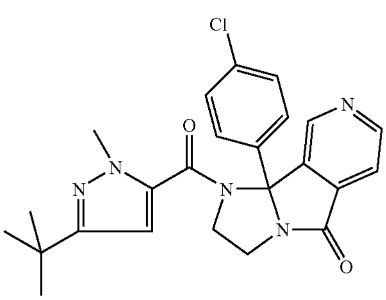 [SMILES: Cn1nc(C(C)(C)C)cc1C(=O)N1CCN2C(=O)c3ccncc3C21c1ccc(Cl)cc1] | 450 | H |
| 426 | 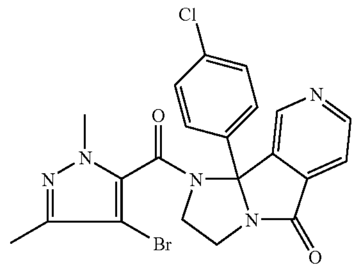 [SMILES: Cc1nn(C)c(C(=O)N2CCN3C(=O)c4ccncc4C32c2ccc(Cl)cc2)c1Br] | 488 | H |
| 427 | 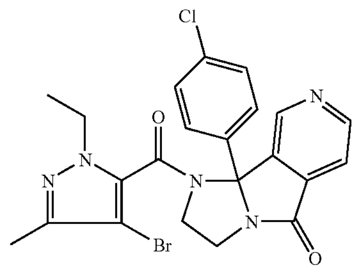 [SMILES: CCn1nc(C)c(Br)c1C(=O)N1CCN2C(=O)c3ccncc3C21c1ccc(Cl)cc1] | 502 | H |
| 428 | 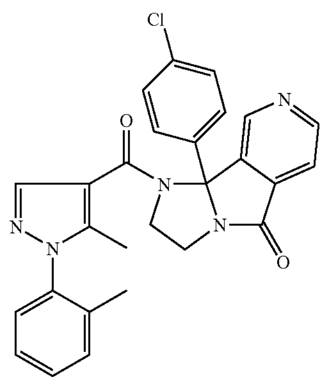 [SMILES: Cc1ccccc1-n1ncc(C(=O)N2CCN3C(=O)c4ccncc4C32c2ccc(Cl)cc2)c1C] | 484 | H |
| 429 | 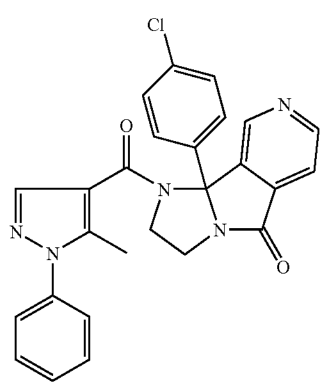 [SMILES: Cc1c(C(=O)N2CCN3C(=O)c4ccncc4C32c2ccc(Cl)cc2)cnn1-c1ccccc1] | 470 | H |

TABLE 3-continued

Compounds of the Invention (Formula I where A is Heteroaryl)

| No. | Structure | m/z M + H⁺ | Mtd |
|---|---|---|---|
| 430 | 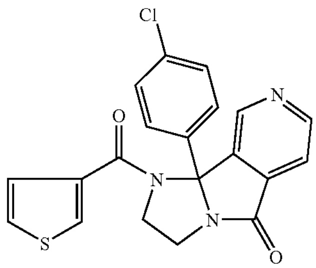 | 396 | H |
| 431 | 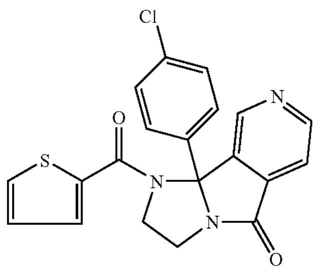 | 396 | H |
| 432 | 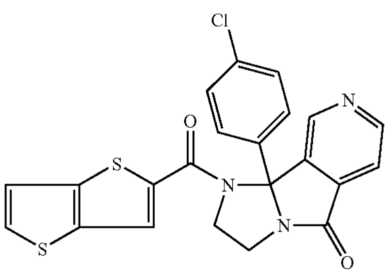 [SMILES: O=C(c1cc2sccc2s1)N1CCN2C(=O)c3ccncc3C12c1ccc(Cl)cc1] | 452 | H |
| 433 | 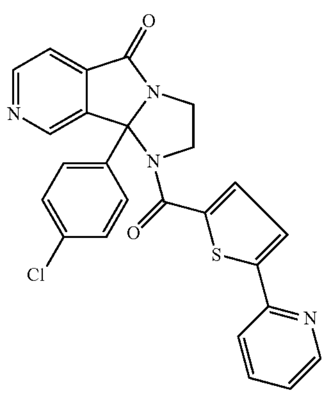 [SMILES: O=C(c1ccc(-c2ccccn2)s1)N1CCN2C(=O)c3ccncc3C12c1ccc(Cl)cc1] | 473 | H |
| 434 | 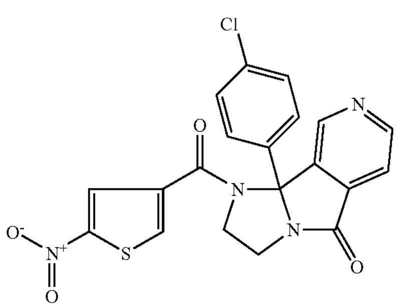 [SMILES: O=C(c1csc([N+](=O)[O-])c1)N1CCN2C(=O)c3ccncc3C12c1ccc(Cl)cc1] | 441 | H |
| 435 | 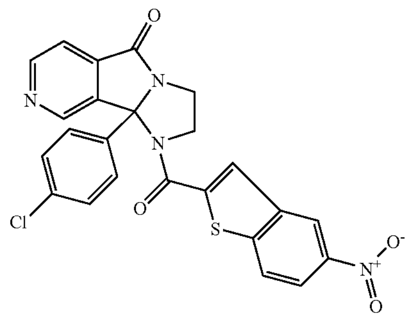 [SMILES: O=C(c1cc2cc([N+](=O)[O-])ccc2s1)N1CCN2C(=O)c3ccncc3C12c1ccc(Cl)cc1] | 491 | H |
| 436 | 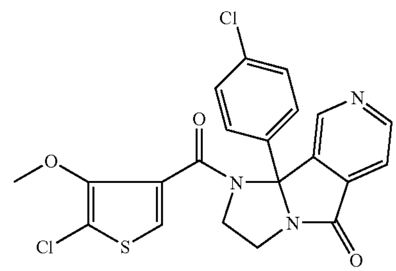 [SMILES: COc1c(C(=O)N2CCN3C(=O)c4ccncc4C32c2ccc(Cl)cc2)csc1Cl] | 460 | H |
| 437 | 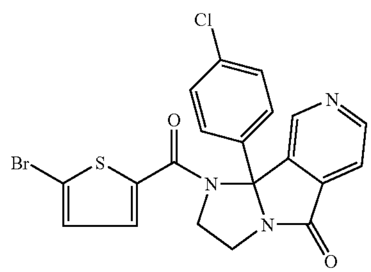 [SMILES: O=C(c1ccc(Br)s1)N1CCN2C(=O)c3ccncc3C12c1ccc(Cl)cc1] | 476 | H |
| 438 | 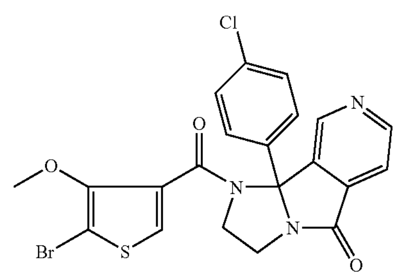 [SMILES: COc1c(C(=O)N2CCN3C(=O)c4ccncc4C32c2ccc(Cl)cc2)csc1Br] | 506 | H |
| 439 | 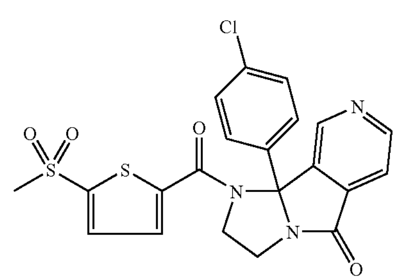 [SMILES: CS(=O)(=O)c1ccc(C(=O)N2CCN3C(=O)c4ccncc4C23c2ccc(Cl)cc2)s1] | 474 | H |

TABLE 3-continued

Compounds of the Invention (Formula I where A is Heteroaryl)

| No. | Structure | m/z M + H⁺ | Mtd |
|---|---|---|---|
| 440 | 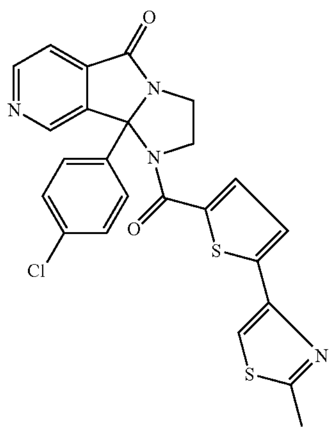 [SMILES: Cc1nc(-c2ccc(C(=O)N3CCN4C(=O)c5ccncc5C34c3ccc(Cl)cc3)s2)cs1] | 493 | H |
| 441 | 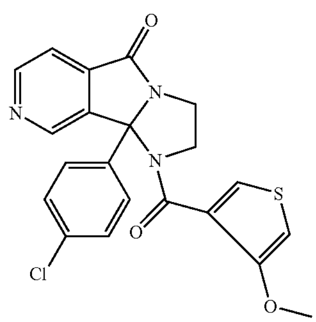 [SMILES: COc1cscc1C(=O)N1CCN2C(=O)c3ccncc3C12c1ccc(Cl)cc1] | 426 | H |
| 442 | 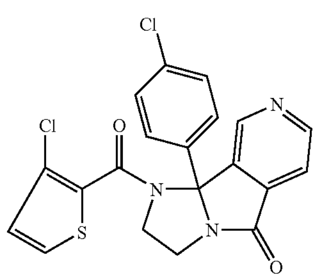 [SMILES: O=C1c2ccncc2C2(c3ccc(Cl)cc3)N1CCN2C(=O)c1sccc1Cl] | 430 | H |
| 443 | 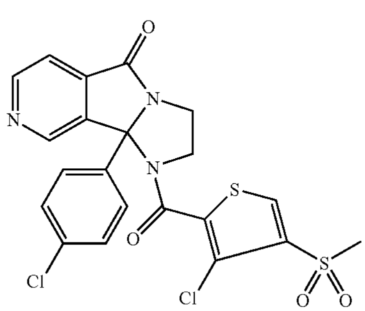 [SMILES: CS(=O)(=O)c1csc(C(=O)N2CCN3C(=O)c4ccncc4C32c2ccc(Cl)cc2)c1Cl] | 508 | H |
| 444 | | 411 | H |
| 445 | | 476 | H |
| 446 | | 478 | H |
| 447 | | 446 | H |

TABLE 3-continued

Compounds of the Invention (Formula I where A is Heteroaryl)

| No. | Structure | m/z M+H+ | Mtd |
|---|---|---|---|
| 448 | 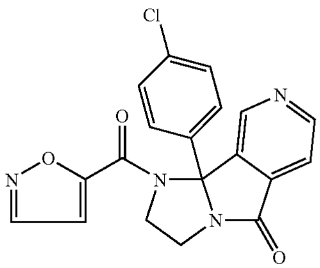 [SMILES: O=C(c1ccno1)N1CCN2C(=O)c3ccncc3C12c1ccc(Cl)cc1] | 381 | H |
| 449 | 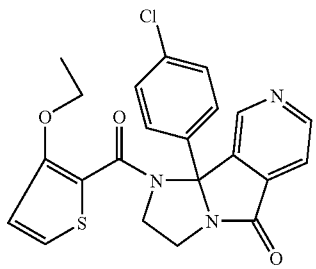 [SMILES: CCOc1ccsc1C(=O)N1CCN2C(=O)c3ccncc3C21c1ccc(Cl)cc1] | 440 | H |
| 450 | 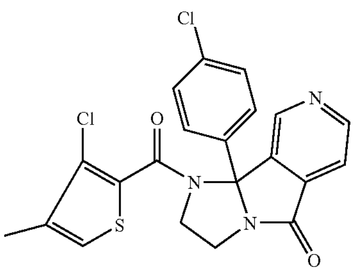 [SMILES: Cc1csc(C(=O)N2CCN3C(=O)c4ccncc4C32c2ccc(Cl)cc2)c1Cl] | 444 | H |
| 451 | 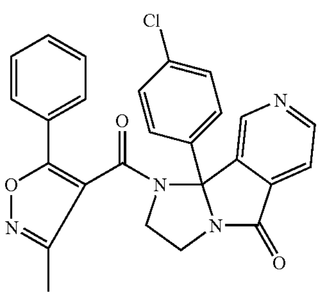 [SMILES: Cc1noc(-c2ccccc2)c1C(=O)N1CCN2C(=O)c3ccncc3C21c1ccc(Cl)cc1] | 471 | H |
| 452 | 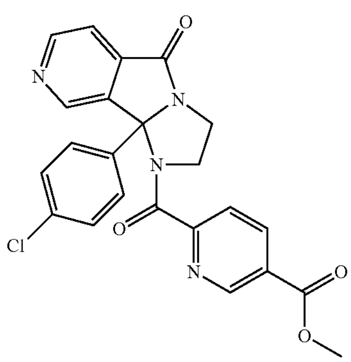 [SMILES: COC(=O)c1ccc(C(=O)N2CCN3C(=O)c4ccncc4C23c2ccc(Cl)cc2)nc1] | 449 | H |
| 453 | | 425 | H |
| 454 | | 472 | H |
| 455 | | 391 | H |
| 456 | | 398 | H |
| 457 | | 474 | H |

TABLE 3-continued

Compounds of the Invention (Formula I where A is Heteroaryl)

| No. | Structure | m/z M+H+ | Mtd |
|---|---|---|---|
| 458 | 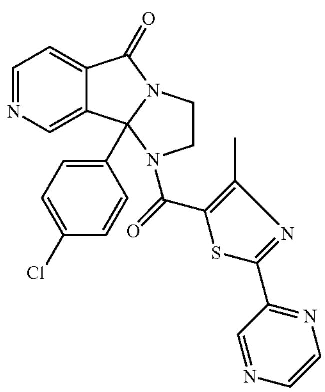 | 489 | H |
| 459 | 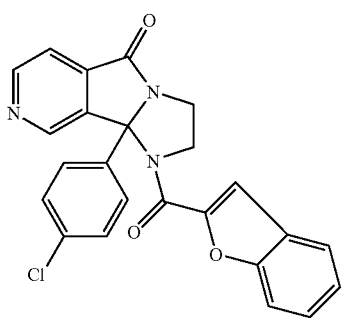 [SMILES: O=C(c1cc2ccccc2o1)N1CCN2C(=O)c3ccncc3C12c1ccc(Cl)cc1] | 430 | H |
| 460 | 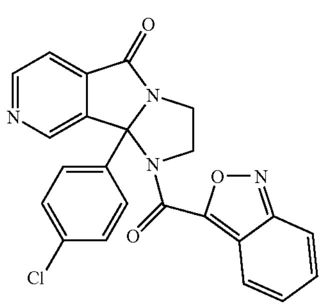 [SMILES: O=C1c2ccncc2C2(c3ccc(Cl)cc3)N1CCN2C(=O)c1onc2ccccc12] | 431 | H |
| 461 | 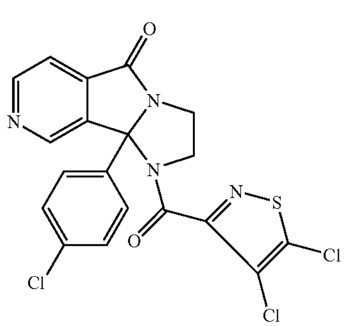 [SMILES: O=C1c2ccncc2C2(c3ccc(Cl)cc3)N1CCN2C(=O)c1nsc(Cl)c1Cl] | 465 | H |
| 462 | | 487 | H |
| 463 | | 457 | H |
| 464 | | 440 | H |
| 465 | | 487 | H |

TABLE 3-continued

Compounds of the Invention (Formula I where A is Heteroaryl)

| No. | Structure | m/z M+H+ | Mtd |
|---|---|---|---|
| 466 | 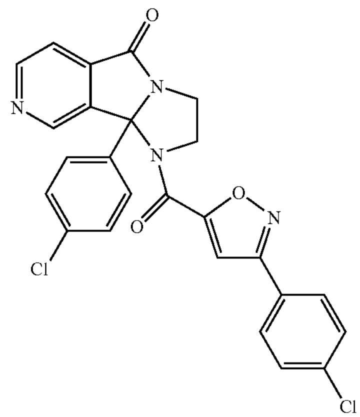 [SMILES: O=C(c1cc(-c2ccc(Cl)cc2)no1)N1CCN2C(=O)c3ccncc3C12c1ccc(Cl)cc1] | 491 | H |
| 467 | 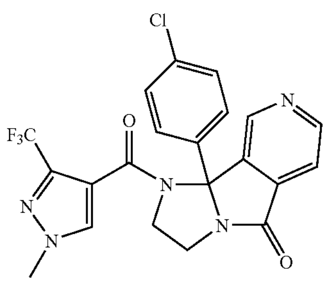 [SMILES: Cn1cc(C(=O)N2CCN3C(=O)c4ccncc4C32c2ccc(Cl)cc2)c(C(F)(F)F)n1] | 462 | H |
| 468 | 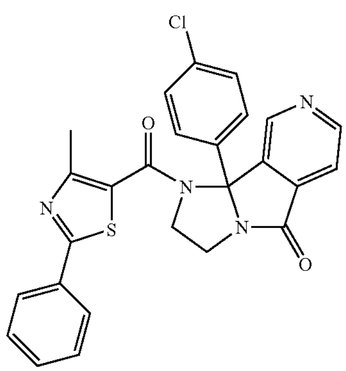 [SMILES: Cc1nc(-c2ccccc2)sc1C(=O)N1CCN2C(=O)c3ccncc3C21c1ccc(Cl)cc1] | 488 | H |
| 469 | 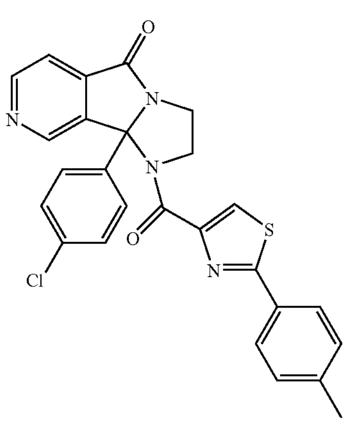 [SMILES: Cc1ccc(-c2nc(C(=O)N3CCN4C(=O)c5ccncc5C34c3ccc(Cl)cc3)cs2)cc1] | 487 | H |
| 470 | | 493 | H |
| 471 | | 507 | H |
| 472 | | 457 | H |
| 473 | | 488 | H |

TABLE 3-continued

Compounds of the Invention (Formula I where A is Heteroaryl)

| No. | Structure | m/z M+H⁺ | Mtd |
|---|---|---|---|
| 474 | | 473 | H |
| 475 | | 516 | H |
| 476 | | 503 | H |
| 477 | 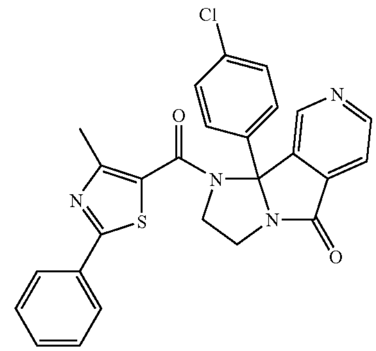 [SMILES: Cc1nc(-c2ccccc2)sc1C(=O)N1CCN2C(=O)c3ccncc3C21c1ccc(Cl)cc1] | 487 | H |
| 478 | 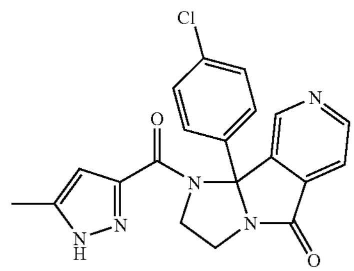 [SMILES: Cc1cc(C(=O)N2CCN3C(=O)c4ccncc4C23c2ccc(Cl)cc2)n[nH]1] | 394 | H |
| 479 | 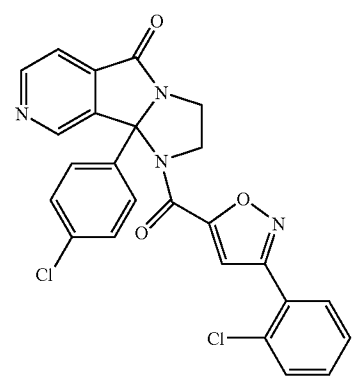 [SMILES: O=C(c1cc(-c2ccccc2Cl)no1)N1CCN2C(=O)c3ccncc3C12c1ccc(Cl)cc1] | 491 | H |
| 480 | 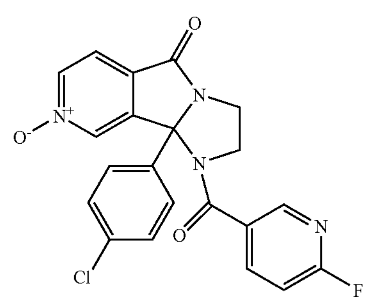 [SMILES: O=C(c1ccc(F)nc1)N1CCN2C(=O)c3cc[n+]([O-])cc3C12c1ccc(Cl)cc1] | 425 | J |

TABLE 3-continued

Compounds of the Invention (Formula I where A is Heteroaryl)

| No. | Structure | m/z M+H⁺ | Mtd |
|-----|-----------|----------|-----|
| 481 | 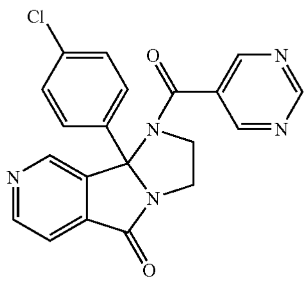 [SMILES: O=C(c1cncnc1)N1CCN2C(=O)c3ccncc3C12c1ccc(Cl)cc1] | 392 | H |
| 482 | 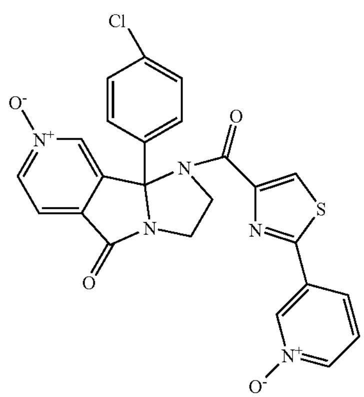 [SMILES: O=C(c1csc(-c2ccc[n+]([O-])c2)n1)N1CCN2C(=O)c3cc[n+]([O-])cc3C12c1ccc(Cl)cc1] | 506 | J |
| 483 | 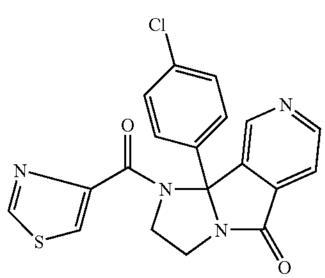 [SMILES: O=C(c1cscn1)N1CCN2C(=O)c3ccncc3C12c1ccc(Cl)cc1] | 397 | H |
| 484 | 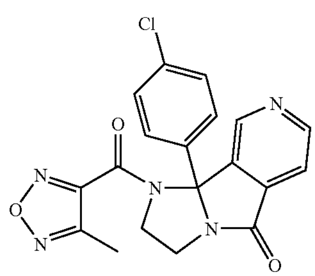 [SMILES: Cc1nonc1C(=O)N1CCN2C(=O)c3ccncc3C21c1ccc(Cl)cc1] | 396 | H |
| 485 | 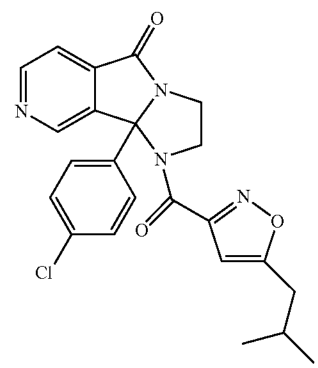 [SMILES: CC(C)Cc1cc(C(=O)N2CCN3C(=O)c4ccncc4C23c2ccc(Cl)cc2)no1] | 437 | H |
| 486 | 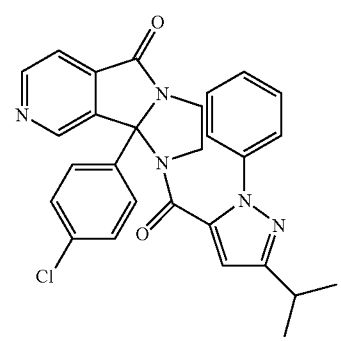 [SMILES: CC(C)c1cc(C(=O)N2CCN3C(=O)c4ccncc4C32c2ccc(Cl)cc2)n(-c2ccccc2)n1] | | H |
| 487 | 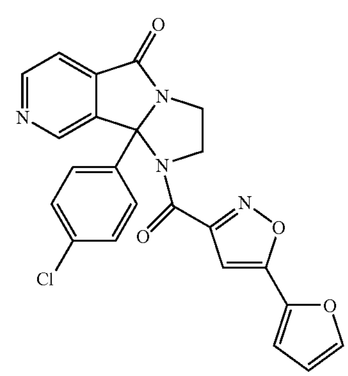 [SMILES: O=C(c1cc(-c2ccco2)on1)N1CCN2C(=O)c3ccncc3C12c1ccc(Cl)cc1] | 447 | H |
| 488 | 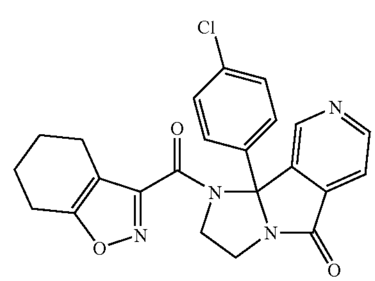 [SMILES: O=C1c2ccncc2C2(c3ccc(Cl)cc3)N1CCN2C(=O)c1noc2c1CCCC2] | 435 | H |

TABLE 3-continued
Compounds of the Invention (Formula I where A is Heteroaryl)
| No. | Structure | m/z M+H+ | Mtd |
|---|---|---|---|
| 489 | 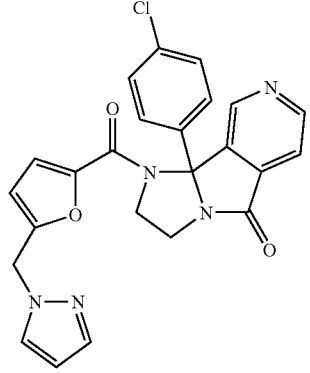 [SMILES: O=C(c1ccc(Cn2cccn2)o1)N1CCN2C(=O)c3ccncc3C12c1ccc(Cl)cc1] | 460 | H |
| 490 | 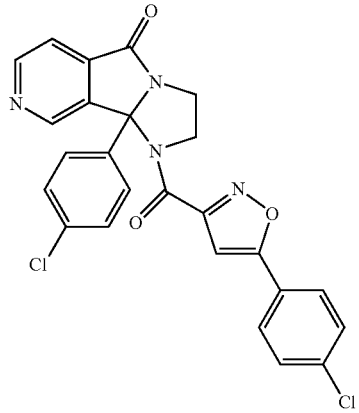 [SMILES: O=C(c1cc(-c2ccc(Cl)cc2)on1)N1CCN2C(=O)c3ccncc3C12c1ccc(Cl)cc1] | * | H |
| 491 | 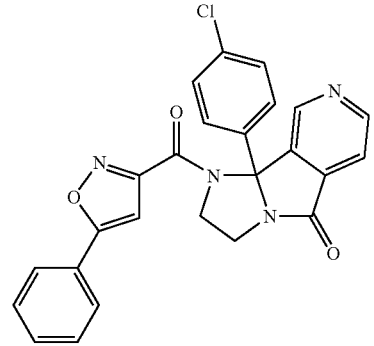 [SMILES: O=C(c1cc(-c2ccccc2)on1)N1CCN2C(=O)c3ccncc3C12c1ccc(Cl)cc1] | 457 | H |
| 492 | 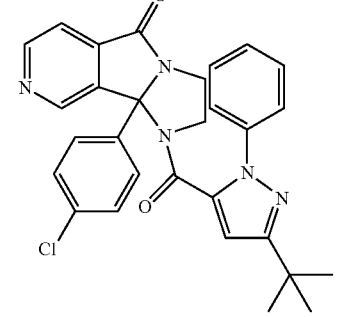 | 512 | H |
| 493 | 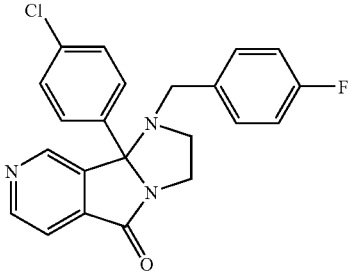 [SMILES: O=C1c2ccncc2C2(c3ccc(Cl)cc3)N(Cc3ccc(F)cc3)CCN12] | 394 | A |
| 494 | 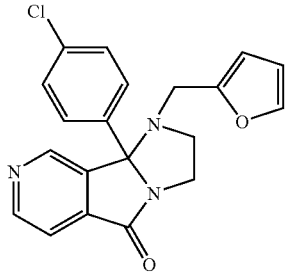 [SMILES: O=C1c2ccncc2C2(c3ccc(Cl)cc3)N(Cc3ccco3)CCN12] | 366 | A |
| 495 | 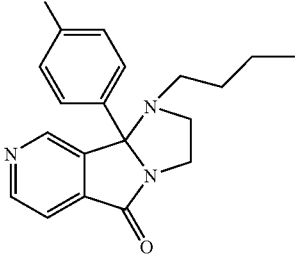 | 342 | A |
| 497 | 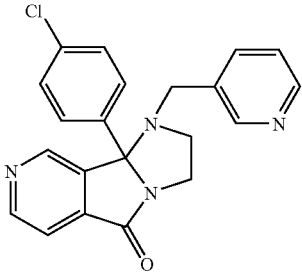 [SMILES: O=C1c2ccncc2C2(c3ccc(Cl)cc3)N(Cc3cccnc3)CCN12] | 377 | A |
| 498 | 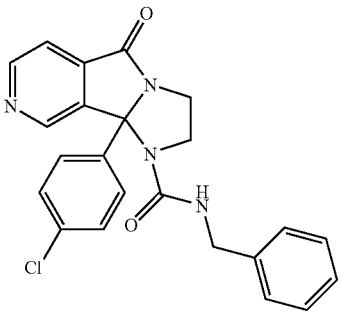 [SMILES: O=C(NCc1ccccc1)N1CCN2C(=O)c3ccncc3C12c1ccc(Cl)cc1] | 419 | H |

TABLE 3-continued

Compounds of the Invention (Formula I where A is Heteroaryl)

| No. | Structure | m/z M+H⁺ | Mtd |
|---|---|---|---|
| 499 | 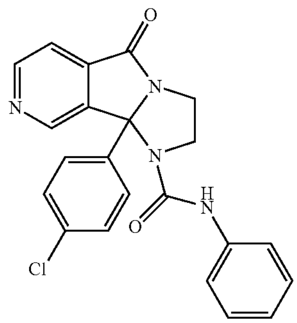 [SMILES: O=C(Nc1ccccc1)N1CCN2C(=O)c3ccncc3C12c1ccc(Cl)cc1] | 405 | H |
| 500 | 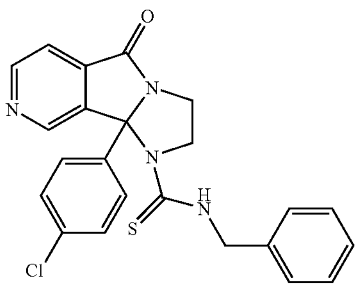 [SMILES: O=C1c2ccncc2C2(c3ccc(Cl)cc3)N1CCN2C(=S)NCc1ccccc1] | 435 | H |
| 501 | 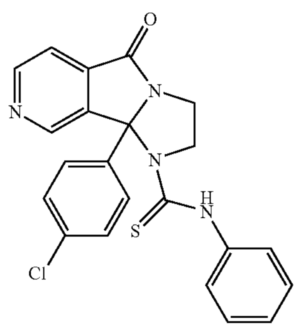 [SMILES: O=C1c2ccncc2C2(c3ccc(Cl)cc3)N1CCN2C(=S)Nc1ccccc1] | 421 | H |
| 502 | 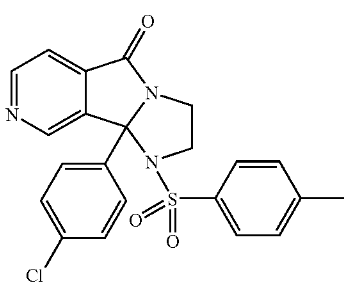 [SMILES: Cc1ccc(S(=O)(=O)N2CCN3C(=O)c4ccncc4C32c2ccc(Cl)cc2)cc1] | 440 | D |

Method O: Separation of Stereoisomers by Chiral Chromatography

Selected compounds of the invention may be separated into single stereoisomers by HPLC using chromatographic columns with a chiral stationary phase. For example, the following racemic compounds were separated into enantiomers under the conditions detailed below.

Column: Chirex 3014 (Chirex (S)-VAL and (R)-NEA)) 250× 10.0 mm
Detector wavelength: 220 nm
Separation of Compound 12
Mobile Phase A: Hexane
Mobile Phase B: Isopropanol
Flow Rate: 4 mL/min
Isocratic Elution: 93% Mobile Phase A, 7% Mobile Phase B
Run Time: 20 mins
Column Temperature: 35° C.
Injection Volume: 20 µl
Separation of Compound 188
Mobile Phase A: Hexane
Mobile Phase B: Isopropanol
Flow Rate: 4 mL/min
Isocratic Elution: 93% Mobile Phase A, 7% Mobile Phase B
Run Time: 26 mins
Column Temperature: 35° C.
Injection Volume: 15 µl
Separation of Compound 306
Mobile Phase A: Hexane
Mobile Phase B: Ethanol
Flow Rate: 4 mL/min
Column Temperature: 25° C.
Injection Volume: 20 µl
Gradient Timetable:

| Time (min) | % Mobile Phase B |
|---|---|
| 0 | 5 |
| 15 | 25 |
| 15 | 25 |
| 17 | 5 |
| 22 | 5 |

Separation of Compound 336
Mobile Phase A: Hexane
Mobile Phase B: Isopropanol
Flow Rate: 4 mL/min
Isocratic Elution: 93% Mobile Phase A, 7% Mobile Phase B
Run Time: 50 mins
Column Temperature: 35° C.
Injection Volume: 25 µl
Separation of Compound 352
Mobile Phase A: Hexane
Mobile Phase B: Ethanol
Flow Rate: 4 mL/min
Column Temperature: 25° C.
Injection Volume: 15 µl
Gradient Timetable:

| Time (min) | % Mobile Phase B |
|---|---|
| 0 | 15 |
| 15 | 20 |
| 23 | 20 |
| 24 | 15 |
| 29 | 15 |

Separation of Compound 363
Mobile Phase A: Hexane
Mobile Phase B: Isopropanol
Flow Rate: 4 mL/min
Column Temperature: 50° C.
Injection Volume: 15 µl
Gradient Timetable:

| Time (min) | % Mobile Phase B |
|---|---|
| 0 | 17 |
| 25 | 35 |
| 26 | 17 |
| 31 | 17 |

Separation of Compound 368
Mobile Phase A: Hexane
Mobile Phase B: Ethanol
Flow Rate: 4 mL/min
Column Temperature: 25° C.
Injection Volume: 15 µl
Gradient Timetable:

| Time (min) | % Mobile Phase B |
|---|---|
| 0 | 5 |
| 15 | 25 |
| 24 | 25 |
| 25 | 5 |
| 30 | 5 |

Separation of Compound 381
Mobile Phase A: Hexane
Mobile Phase B: Ethanol
Flow Rate: 4 mL/min
Column Temperature: 30° C.
Injection Volume: 20 µl
Gradient Timetable:

| Time (min) | % Mobile Phase B |
|---|---|
| 0 | 3 |
| 15 | 20 |
| 24 | 20 |
| 25 | 3 |
| 30 | 3 |

Separation of Compound 414
Mobile Phase A: Hexane
Mobile Phase B: Ethanol
Flow Rate: 4 mL/min
Isocratic Elution: 92% Mobile Phase A, 8% Mobile Phase B
Run Time: 25 mins
Column Temperature: 40° C.
Injection Volume: 20 µl

TABLE 4

Separation of Enantiomers Using Chirex 3014 Column

| Compound Number | Retention Time of Enantiomer A (mins) | Retention Time of Enantiomer B (mins) |
|---|---|---|
| 12 | 13.1 | 14.6 |
| 188 | 13.4 | 14.8 |
| 306 | 12.9 | 13.7 |
| 336 | 6.7 | 7.4 |
| 352 | 20.4 | 21.3 |
| 363 | 17.6 | 19.5 |
| 368 | 15.8 | 16.9 |
| 381 | 20.8 | 21.9 |
| 414 | 21.5 | 22.3 |

Column: Chiracel OD-H (250 mm×4.6 mm)
Isocratic Elution: hexane:ethanol (70:30)
Detector wavelength: 254 nm
Flow rate: 0.7 ml/min
Injection Volume: 20 µl
Column Temperature: 25° C.

TABLE 5

Separation of Enantiomers Using Chiracel OD-H Column

| Compound Number | Retention Time of Enantiomer A (mins) | Retention Time of Enantiomer B (mins) |
|---|---|---|
| 153 | 15.4 | 12.4 |
| 363 | 89.6 | 55.1 |
| 414 | 23.8 | 17.6 |

Method P: Resolution of Compounds of Type III by Diastereomeric Salt Formation

A mixture of Compound 153 (1.0 g, 3.5 mmol) and (R)-(−)-1,1'-Binaphthyl-2,2'-diyl hydrogen phosphate (0.85 g, 2.44 mmol, 0.7 eq) in ethanol (90 ml) was refluxed until a clear solution was formed. After 15 minutes, the mixture was allowed to cool to room temperature for 1 h and then continued stirring under ice cooling for 1.5 h. The white crystalline salt was filtered, rinsed with ethanol (5 ml) and dried under suction for 30 minutes to yield 1.09 g of salt.

The white salt was suspended in water (25 ml) and basified with 10% NaOH solution (0.7 ml) to pH 11. The aqueous phase was extracted with ethyl acetate (100 ml then 2×75 ml). The combined organic extracts were washed with saturated NaCl solution, dried (MgSO$_4$) and concentrated to yield Compound 153B (0.49 g) as a white powder.

The (R)-(−)-1,1'-Binaphthyl-2,2'-diyl hydrogen phosphate was recovered from the acidified aqueous layer (pH 2) by extraction with ethyl acetate (2×100 ml). The combined organic phases were washed with saturated NaCl solution, dried (MgSO$_4$) and concentrated to afford a white powder (0.54 g).

RSV Antiviral Assays
Method Q: RSV Antiviral Assay Protocol

Compounds of the invention were tested for their antiviral activity against respiratory syncytial virus. Cytopathic effect (CPE) assays were performed essentially as described in the literature (see for example Watanabe et al, 1. Virological Methods, 1994, 48, 257). Serial dilutions of the test compounds were made in assay medium. HEp2 cells (1.0×10$^4$ cells/well) were infected with RSV at a low multiplicity of infection (e.g. RSV A2 at an moi of 0.01) and 100 µL added to cultures assessing antiviral activity and cells without virus added to those assessing compound cytotoxicity. Assays were incubated for approximately 5 days at 37° C. in a 5% CO$_2$ atmosphere. The extent of CPE was determined via metabolism of the vital dye 3-(4,5-dimethylthiaxol-2-yl)-2,5-diphenyltetrazolium bromide (MTT). A 3 mg/ml stock of MTT was made in assay medium and 100 µL added to each well, taking the final MTT concentration to 1 mg/ml. After 2 hours incubation at 37° C., the media-MTT solution was removed and 200 µL of isopropanol was added to dissolve the vital dye crystals. Plates were shaken and the absorbance read at 540 nm. The compound concentrations that inhibited CPE by 50% (EC50) and developed cytotoxicity (CC50) were calculated using an Excel curve fitting program.

Representative data for compounds of the invention against RSV A2 is show in Tables 6-8 where EC50 values lie in the ranges A: <100 ng/ml, B: 100-250 ng/ml and C: 250-1000 ng/ml.

TABLE 6

RSV A2 Antiviral Data for Compounds of Table 2

| Cpd No. | Activity Range |
|---|---|
| 12 | B |
| 66 | B |
| 82 | C |
| 85 | B |
| 86 | B |
| 87 | B |
| 88 | A |
| 117 | C |
| 144 | B |
| 178 | C |
| 179 | C |
| 180 | C |
| 183 | B |
| 184 | A |
| 188 | C |
| 190 | C |
| 191 | A |
| 192 | C |
| 199 | C |
| 200 | A |
| 201 | C |
| 203 | C |
| 205 | A |
| 211 | C |
| 214 | C |
| 216 | C |
| 217 | B |
| 218 | C |
| 219 | A |
| 224 | A |
| 227 | C |
| 228 | C |
| 230 | A |
| 231 | C |
| 232 | C |
| 234 | A |
| 235 | B |
| 236 | B |
| 237 | C |
| 238 | B |
| 239 | B |
| 242 | B |
| 243 | A |
| 245 | C |
| 250 | C |
| 260 | B |
| 261 | B |
| 262 | B |
| 263 | B |
| 264 | C |
| 265 | B |
| 266 | C |
| 267 | A |
| 268 | C |
| 299 | C |
| 303 | C |
| 304 | C |
| 305 | C |
| 306 | A |
| 307 | B |
| 308 | B |
| 309 | C |
| 310 | C |
| 311 | B |
| 312 | C |
| 314 | B |
| 316 | A |
| 319 | C |
| 320 | C |
| 323 | C |
| 324 | B |
| 325 | A |
| 326 | B |
| 327 | B |
| 328 | B |
| 329 | B |
| 330 | B |
| 331 | C |
| 332 | A |
| 333 | A |
| 334 | B |
| 335 | A |

TABLE 7

RSV A2 Antiviral Data for Compounds of Table 3

| Cpd No. | Activity Range |
|---|---|
| 336 | B |
| 344 | C |
| 351 | C |
| 352 | B |
| 358 | B |
| 360 | C |
| 361 | B |
| 363 | A |
| 364 | C |
| 366 | A |
| 367 | C |
| 368 | A |
| 369 | B |
| 370 | C |
| 371 | C |
| 372 | C |
| 377 | A |
| 379 | B |
| 381 | A |
| 382 | C |
| 385 | A |
| 386 | B |
| 387 | B |
| 391 | A |
| 392 | B |
| 394 | C |
| 395 | C |
| 397 | B |
| 398 | B |
| 399 | C |
| 401 | B |
| 404 | C |
| 405 | B |
| 406 | C |
| 408 | C |
| 409 | B |
| 412 | A |
| 413 | A |
| 414 | A |
| 415 | C |
| 416 | C |
| 420 | C |
| 421 | C |
| 422 | C |
| 423 | C |
| 430 | A |
| 431 | A |
| 434 | C |
| 436 | B |
| 437 | C |
| 438 | C |
| 441 | B |
| 442 | A |
| 444 | B |
| 445 | A |
| 448 | B |
| 449 | A |
| 450 | B |
| 453 | A |
| 454 | B |

TABLE 7-continued

RSV A2 Antiviral Data for Compounds of Table 3

| Cpd No. | Activity Range |
|---|---|
| 455 | C |
| 456 | A |
| 457 | C |
| 458 | B |
| 461 | A |
| 462 | A |
| 463 | A |
| 464 | C |
| 465 | C |
| 467 | A |
| 468 | C |
| 474 | B |
| 480 | A |
| 481 | C |
| 482 | A |
| 483 | A |
| 484 | A |

TABLE 8

RSV A2 Antiviral Data for Compounds of Tables 4 and 5 (the B enantiomer)

| Cpd No. | Activity Range |
|---|---|
| 12B | A |
| 188B | B |
| 306B | A |
| 336B | A |
| 352B | A |
| 363B | A |
| 368B | A |
| 381B | A |
| 414B | A |

Method R: RSV Fusion Assay

Selected compounds of the invention were tested for their ability to inhibit the essential fusion processes of the respiratory syncytial virus.

Generation of RSV-F Constructs

Single-stranded synthetic DNA oligonucleotides encoding the portions of RSV A2 F glycoprotein incorporating optimal codons and without potential poly(A) addition or splice sites were generated synthetically (Mason et al, WO0242326). A membrane-anchored full-length F was generated essentially according to the method described therein and in Morton et al, Virology, 2003, 311, 275.

Syncytium Formation Assay

Fusion activity of the RSV-F constructs was measured in 293 cells essentially according to the method described in Morton et al, Virology, 2003, 311, 275. For example: cells in six well plates at approximately 80% confluency were transfected by adding plasmid DNA (2 μg/well) carrying the constructs of interest in $CaPO_4$ solution for 4 hours. After glycerol shock and wash, the transfected cells were trypsinized and $1.5 \times 10^4$ cells/well added to 96-well plates containing half-log serial dilutions of the test compound. Syncytium formation was evaluated by visual inspection and quantified at 48 hours post-transfection by addition of 20 μL of CellTiter 96 One Solution (Promega) followed by incubation for 4 hours at 37° C. The colour reaction was then stopped by addition of 25 μL 10% SDS to each well and absorbance measured at 492 nm. The compound concentration that reduced absorbance relative to untreated control cultures by 50% (EC50) was calculated using an Excel curve fitting program.

Representative data for compounds of the invention is show in Table 9 where EC50 values lie in the ranges A: <750 ng/ml, B: 750-1500 ng/ml and C: 1500-2250 ng/ml.

TABLE 9

RSV Fusion Assay Data

| Compound Number | RSV Fusion Assay EC50 |
|---|---|
| 12 | C |
| 16 | B |
| 66 | B |
| 336 | A |

Method S: RSV Cotton Rat Model

The cotton rat model was performed essentially as described in the literature (Wyde et al, *Antiviral Res.* 2003, 60, 221). Briefly, cotton rats weighing 50-100 g were lightly anesthetized with isoflurane and dosed orally with 100 mg/kg/day of compound or vehicle control. Viral infection followed 2 hours post-treatment in similarly anesthetized rats by intranasal instillation with approximately 1000 TCID50 of RSV A2 per animal. Four days after virus inoculation, each cotton rat was sacrificed and their lungs removed and RSV titres determined by plaque assay.

TABLE 10

RSV Cotton Rat Model Data

| Compound Number | % Reduction of virus Control |
|---|---|
| 352 | 68 |
| 306 | 72 |
| 336 | 96 |

Method T: RSV Balb/c Mouse Model

The mouse model was performed essentially as described by Clanci et al (*Antimicrobial Agents and Chemotherapy.* 2004, 48, 413). Briefly, eight week old female Balb/c mice were weighed, anesthetized intraperitoneally with Avertin™ and compound or vehicle administered orally 6 hours preinfection. Mice were inoculated intranasally with approximately 10000 TCID50 RSV A2 per animal. Three days after virus inoculation, each mouse was sacrificed and their lungs removed and RSV titres determined by plaque assay.

TABLE 11

RSV Balb/c Mouse Model Data

| Compound Number | % reduction of virus control |
|---|---|
| 336 | 80 |

It would be appreciated by a person skilled in the art the numerous variations and/or modifications may be made to the invention as shown the specific embodiments without departing from the spirit or scope of the invention as broadly described. The present embodiments are, therefore, to be considered in all respects as illustrative and not restrictive.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference to any prior art in this specification is not, and should not be taken as an acknowledgment or any form or suggestion that that prior art forms part of the common general knowledge in Australia.

The invention claimed is:

1. A method for treating a mammal infected with respiratory syncytial virus (RSV), which comprises administering to the mammal a therapeutically effective amount of one or more compounds of formula I:

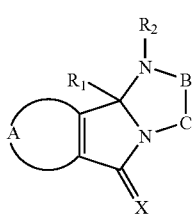

Formula I or pharmaceutically acceptable salts or derivatives thereof, wherein

A, together with the atoms to which it is attached, forms an optionally substituted pyridyl ring;

linker —B—C— is an optionally substituted linker of the formula —$CH_2(CH_2)_z$—, where z is 1;

$R_1$ is optionally substituted aryl;

$R_2$ is —C(O)$R_3$, where $R_3$ is selected from —$(CH_2)_m$ aryl and —$(CH_2)_m$ heterocyclyl; where m is 0 or 1; and the aryl and heterocyclyl groups are optionally substituted; and X is O.

2. The method according to claim 1, wherein ring A is optionally substituted with one or more substituents independently selected from halo, —$NH_2$, —$NO_2$, $C_{1-6}$ alkyl, aryl and heterocyclyl, where the aryl and heterocyclyl groups are optionally substituted with halo, $C_{1-6}$ alkyl or halo substituted $C_{1-6}$ alkyl, and the optional substituents are further selected from an N-oxide of the pyridyl ring nitrogen and pyridinium salts thereof.

3. The method according to claim 2, wherein ring A is optionally substituted with a substituent selected from halo, alkyl, $C_6H_5$—, $CH_3$—$C_6H_4$—, $CF_3$—$C_6H_4$—, pyridyl and —$NO_2$, and the optional substituent is further selected from an N-oxide form of the ring nitrogen, and pyridinium salts thereof.

4. The method according to claim 1, wherein ring A is not substituted.

5. The method according to claim 1, wherein the compound of formula I is a compound of the formula IV

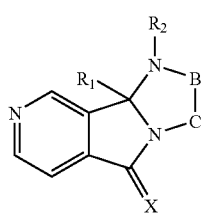

Formula IV or an N-oxide or pharmaceutically acceptable salt or derivative thereof.

6. The method according to claim 1, wherein $R_2$ is —C(O)$R_3$, where $R_3$ is selected from —$(CH_2)_m$ aryl and —$(CH_2)_m$ heterocyclyl; and the aryl and heterocyclyl groups are optionally substituted with one or more substituents selected from $C_{1-6}$ alkyl, $C_{1-6}$ alkoxy, $C_{2-6}$ alkenyl, $C_{2-6}$ alkynyl, halo, halo-$C_{1-6}$ alkyl, $CF_3$, hydroxy, mercapto, nitro, cyano, $NH_2$, mono and di($C_{1-6}$ alkyl)amino, phenyl, benzyl and heterocyclyl.

7. The method according to claim 1, wherein $R_3$ is optionally substituted and is selected from phenyl, naphthyl, furyl, thienyl, pyrrolyl, H-pyrrolyl, pyrrolinyl, pyrrolidinyl, oxazolyl, oxadiazolyl, 1,2,3-oxadiazolyl, 1,2,4-oxadiazolyl, thiazolyl, isoxazolyl, furazanyl, isothiazolyl, pyrazolyl, pyrazolinyl, pyrazolidinyl, imidazolyl, imidazolinyl, triazolyl, 1,2,3-triazolyl, 1,3,4-triazolyl, tetrazolyl, thiadiazolyl, 1,2,3-thiadiazolyl, 1,3,4-thiadiazolyl, pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl, triazinyl, 1H-thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl and pteridinyl.

8. The method according to claim 7, wherein $R_3$ is optionally substituted with one or more substituents selected from $C_{1-6}$ alkyl, $C_{1-6}$alkoxy, $C_{2-6}$ alkenyl, $C_{2-6}$ alkynyl, halo, halo-$C_{1-6}$ alkyl, $CF_3$, hydroxy, mercapto, nitro, cyano, $NH_2$, mono and di($C_{1-6}$ alkyl)amino, phenyl, benzyl and heterocyclyl.

9. The method according to claim 1, wherein linker —B—C— is not substituted.

10. The method according to claim 1, wherein $R_1$ represents phenyl, optionally substituted with halo, hydroxy, nitro, —NR'R", $C_{1-12}$ alkyl, phenyl or —O—$R_a$, where R' and R" are independently selected from hydrogen, lower alkyl and —C(O)R, where R is $C_{1-6}$ alkyl, phenyl or heterocyclyl; $R_a$ is —$C_{1-12}$ alkyl, —$C_{3-7}$ cycloalkyl, —$C_{1-12}$ alkyl$C_{3-7}$ cycloalkyl, phenyl or —$C_{1-12}$ alkylphenyl; and the $C_{1-12}$ alkyl, phenyl or $R_a$ group is optionally substituted with halo, —CN, —$NR^{10}R^{11}$, —$CO_2R^{12}$ or —$CONR^{10}R^{11}$, where $R^{10}$, $R^{11}$ and $R^{12}$ are independently selected from hydrogen and lower alkyl.

11. The method according to claim 1, wherein $R_1$ is phenyl optionally substituted with a substituent selected from halo, —$C_{1-6}$ alkyl, —$C_{1-6}$ alkylhalo, —$C_{1-6}$ alkylCN, —$OC_{1-6}$ alkyl, —$OC_{1-6}$ alkylhalo, —$OC_{1-6}$ alkylCO$_2$NH$_2$, —$OC_{1-6}$ alkylCN, alkyl$C_{3-7}$ cycloalkyl, —$OC_{1-6}$ alkyl$C_6H_5$, —$OC_{1-6}$ alkylOCH$_3$, —$OC_6H_5$, —$OC_6H_4$halo, —$CF_3$, —$OCF_3$, —NR'R", —$CO_2H$, —$CO_2C_{1-6}$ alkyl, —$NO_2$, —OH, —$C_6H_5$, —$C_6H_4C_{1-6}$ alkyl, —$C_6H_4$halo and —$OC(O)C_{1-6}$ alkyl; where R' and R" are independently selected from hydrogen, —C(O)$C_{1-6}$ alkyl, —C(O)$C_6H_5$, —C(O)CH=CHCO$_2$H, —C(O)$C_{1-6}$ alkylCO$_2$H, —C(O)$C_{1-6}$ alkylCO$_2$CH$_3$, —C(O)$C_{1-6}$ alkyl$C_6H_5$, —C(O)$C_{1-6}$ alkyl$C_6H_4$CH$_3$, —C(O)$C_{1-6}$ alkyl$C_6H_4$OCH$_3$ and —C(O)$C_{1-6}$ alkyl$C_6H_4$halo.

12. The method according to claim 1, wherein $R_1$ is phenyl substituted with halo, $C_{1-6}$ alkyl, —$OC_{1-6}$ alkyl, —$OC_{1-6}$ alkylhalo, —$OC_{1-6}$ alkylCO$_2$NH$_2$, —$OC_{1-6}$ alkylCN, —$OC_{1-6}$ alkyl$C_{3-7}$ cycloalkyl, —$OC_{1-6}$ alkyl$C_6H_5$ or —$OC_{1-6}$ alkylOCH$_3$.

13. The method according to claim 1, wherein $R_1$ is 4-chlorophenyl.

14. A method for the treatment of infections involving RSV by the inhibition of virus fusion processes, comprising administering a therapeutically effective amount of a compound of formula I as defined in claim 1, or a pharmaceutically acceptable salt or derivative thereof, to a patient in need of treatment.

15. The method of claim 1 for the treatment of human RSV.

16. The method according to claim 1, wherein $R_3$ is optionally substituted and is selected from phenyl, furyl, thienyl, oxazolyl, oxadiazolyl, thiazolyl, isoxazolyl, furazanyl, isothiazolyl, pyrazolyl, triazolyl, 1,2,3-triazolyl, thiadiazolyl, 1,2,3-thiadiazolyl, pyridyl, pyrimidinyl, and benzothienyl.

17. A compound of formula I

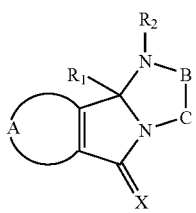

Formula I or a salt or pharmaceutically acceptable derivative thereof, wherein:
A, together with the atoms to which it is attached, represents an optionally substituted pyridyl;
linker —B—C— is an optionally substituted linker of the formula —CH$_2$(CH$_2$)$_z$—, where z is 1;
$R_1$ is optionally substituted;
$R_2$ is —C(O)R$_3$ where R$_3$ is selected from —(CH$_2$)$_m$ aryl and —(CH$_2$)$_m$ heterocyclyl, where m is 0 or 1; and the aryl and heterocyclyl groups are optionally substituted; and
X is O.

18. The compound according to claim 17, or a salt or pharmaceutically acceptable derivative thereof, wherein ring A is optionally substituted with one or more substituents independently selected from halo, —NH$_2$, —NO$_2$, C$_{1-6}$ alkyl, aryl and heterocyclyl, where the aryl and heterocyclyl groups are optionally substituted with halo, C$_{1-6}$ alkyl or halo substituted C$_{1-6}$ alkyl, and the optional substituents are also an N-oxide of the pyridyl ring nitrogen.

19. The compound according to claim 17, or a salt or pharmaceutically acceptable derivative thereof, wherein ring A is optionally substituted with a substituent selected from halo, alkyl, C$_6$H$_5$—, CH$_3$—C$_6$H$_4$—, CF$_3$—C$_6$H$_4$—, pyridyl and —NO$_2$, and the optional substituent is also an N-oxide form of the pyridyl ring nitrogen.

20. The compound according to claim 17, or a salt or pharmaceutically acceptable derivative thereof, wherein ring A is not substituted.

21. The compound according to claim 17, or a salt or pharmaceutically acceptable derivative thereof, wherein R$_2$ is —C(O)R$_3$, where R$_3$ is selected from (CH$_2$)$_m$ aryl and —(CH$_2$)$_m$ heterocyclyl, aryl and heterocyclyl groups are optionally substituted with one or more substituents selected from C$_{1-6}$alkyl, C$_{1-6}$alkoxy, C$_{2-6}$ alkenyl, C$_{2-6}$ alkynyl, halo, halo-C$_{1-6}$ alkyl, CF$_3$, hydroxy, mercapto, nitro, cyano, NH$_2$, mono and di(C$_{1-6}$ alkyl)amino, phenyl, benzyl and heterocyclyl, the substituents being optionally substituted.

22. The compound according to claim 17, or a salt or pharmaceutically acceptable derivative thereof, wherein R$_2$ is —COR$_3$, and R$_3$ is optionally substituted aryl or optionally substituted heterocyclyl.

23. The compound according to claim 22, or a salt or pharmaceutically acceptable derivative thereof, wherein R$_3$ is optionally substituted and is selected from phenyl, naphthyl, furyl, thienyl, pyrrolyl, H-pyrrolyl, pyrrolinyl, pyrrolidinyl, oxazolyl, oxadiazolyl, 1,2,3-oxadiazolyl, 1,2,4-oxadiazolyl, thiazolyl, isoxazolyl, furazanyl, isothiazolyl, pyrazolyl, pyrazolinyl, pyrazolidinyl, imidazolyl, imidazolinyl, triazolyl, 1,2,3-triazolyl, 1,3,4-triazolyl, tetrazolyl, thiadiazolyl, 1,2,3-thiadiazolyl, 1,3,4-thiadiazolyl, pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl, triazinyl, 1H-thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl and pteridinyl.

24. The compound according to claim 17, or a salt or pharmaceutically acceptable derivative thereof, wherein R$_3$ is optionally substituted with one or more substituents selected from C$_{1-6}$ alkyl, C$_{1-6}$alkoxy, C$_{2-6}$ alkenyl, C$_{2-6}$ alkynyl, halo, halo-C$_{1-6}$ alkyl, CF$_3$, hydroxy, mercapto, nitro, cyano, NH$_2$, mono and di(C$_{1-6}$ alkyl)amino, phenyl, benzyl and heterocyclyl, where the phenyl, benzyl and heterocyclyl groups are optionally substituted.

25. The compound according to claim 17, or a salt or pharmaceutically acceptable derivative thereof, wherein the linker —B—C— is not substituted.

26. The compound according to claim 17, or a salt or pharmaceutically acceptable derivative thereof, wherein R$_1$ represents phenyl, optionally substituted with halo, hydroxy, nitro, —NR'R", C$_{1-12}$ alkyl, phenyl or —O—R$_a$, where R' and R" are independently selected from hydrogen, lower alkyl and —C(O)R, where R is C$_{1-6}$ alkyl, phenyl or heterocyclyl; R$_a$ is —C$_{1-12}$ alkyl, —C$_{3-7}$ cycloalkyl, —C$_{1-12}$ alkylC$_{3-7}$ cycloalkyl, phenyl or —C$_{1-12}$ alkylphenyl; and the C$_{1-12}$ alkyl, phenyl or R$_a$ group is optionally substituted with halo, —CN, —NR$^{10}$R$^{11}$, —CO$_2$R$^{12}$ or —CONR$^{10}$R$^{11}$, where R$^{10}$, R$^{11}$ and R$^{12}$ are independently selected from hydrogen and lower alkyl.

27. The compound according to claim 17, or a salt or pharmaceutically acceptable derivative thereof, wherein R$_1$ is phenyl optionally substituted with a substituent selected from halo, —C$_{1-6}$ alkyl, —C$_{1-6}$ alkylhalo, —C$_{1-6}$ alkylCN, —OC$_{1-6}$ alkyl, —OC$_{1-6}$ alkylhalo, —OC$_{1-6}$ alkylCO$_2$NH$_2$, —OC$_{1-6}$ alkylCN, —OC$_{1-6}$ alkylC$_{3-7}$ cycloalkyl, —OC$_{1-6}$ alkylC$_6$H$_5$, —OC$_{1-6}$ alkylOCH$_3$, —OC$_6$H$_5$, —OC$_6$H$_4$halo, —CF$_3$, —OCF$_3$, —NR'R", —CO$_2$H, —CO$_2$C$_{1-6}$ alkyl, —NO$_2$, —OH, —C$_6$H$_5$, —C$_6$H$_4$C$_{1-6}$ alkyl, —C$_6$H$_4$halo and —OC(O)C$_{1-6}$ alkyl; where R' and R" are independently selected from hydrogen, —C(O)C$_{1-6}$ alkyl, —C(O)C$_6$H$_5$, —C(O)CH=CHCO$_2$H, —C(O)C$_{1-6}$ alkylCO$_2$H, —C(O)C$_{1-6}$ alkylCO$_2$CH$_3$, —C(O)C$_{1-6}$ alkylC$_6$H$_5$, —C(O)C$_{1-6}$ alkylC$_6$H$_4$CH$_3$, —C(O)C$_{1-6}$ alkylC$_6$H$_4$OCH$_3$ and —C(O)C$_{1-6}$ alkylC$_6$H$_4$halo.

28. The compound according to claim 17, or a salt or pharmaceutically acceptable derivative thereof, wherein R$_1$ is halo-phenyl.

29. The compound according to claim 17, or a salt or pharmaceutically acceptable derivative thereof, wherein R$_1$ is 4-chlorophenyl.

30. The compound according to claim 17, or a salt or pharmaceutically acceptable derivative thereof, wherein R$_2$ is —C(O)—R$_3$ and R$_3$ is —(CH$_2$)$_m$-aryl or —(CH$_2$)$_m$-heteroaryl, where the aryl or heteroaryl group is optionally substituted.

31. The compound according to claim 17 of the formula IV

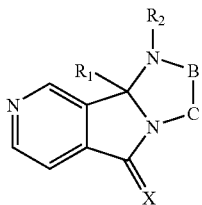

Formula IV or an N-oxide form or pyridinium salt thereof.

32. The compound according to claim 31, or an N-oxide form or pyridium salt thereof, wherein $R_2$ is —C(O)$R_3$ and $R_3$ is —(CH$_2$)$_m$-aryl or —(CH$_2$)$_m$-heteroaryl, where the aryl or heteroaryl group is optionally substituted.

33. A compound selected from the group consisting of:
9b-(4-chloro-phenyl)-1-(4-fluoro-benzoyl)-1,2,3,9b-tetrahydroimidazo[1',2':1,5]-pyrrolo[3,4-b]pyridin-5-one;
3a-(4-chloro-phenyl)-3-(4-fluoro-benzoyl)-1,2,3,3a-tetrahydro-3,6,8a-triaza-cyclopenta[a]inden-8-one;
3a-(4-chloro-phenyl)-3-(4-fluoro-benzoyl)-1,2,3,3a-tetrahydro-3,5,8a-triaza-cyclopenta[a]inden-8-one;
3-(4-fluoro-benzoyl)-3a-p-tolyl-1,2,3,3a-tetrahydro-3,5,8a-triaza-cyclopenta[a]inden-8-one;
3-[2-(4-methoxy-phenyl)-acetyl]-3a-p-tolyl-1,2,3,3a-tetrahydro-3,6,8a-triaza-cyclopenta[a]inden-8-one;
3a-(2-chloro-phenyl)-3-(4-fluoro-benzoyl)-1,2,3,3a-tetrahydro-3,5,8a-triaza-cyclopenta[a]inden-8-one;
3a-(4-chloro-phenyl)-3-[2-(4-methoxy-phenyl)-acetyl]-1,2,3,3a-tetrahydro-3,6,8a-triaza-cyclopenta[a]inden-8-one;
3-(4-fluoro-benzoyl)-3a-(4-trifluoromethyl-phenyl)-1,2,3,3a-tetrahydro-3,6,8a-triaza-cyclopenta[a]inden-8-one;
3-[2-(4-methoxy-phenyl)-acetyl]-3a-(4-trifluoromethyl-phenyl)-1,2,3,3a-tetrahydro-3,6,8a-triaza-cyclopenta[a]inden-8-one;
3-[2-(4-methoxy-phenyl)-acetyl]-3a-(4-trifluoromethyl-phenyl)-1,2,3,3a-tetrahydro-3,5,8a-triaza-cyclopenta[a]inden-8-one;
3a-(4-chloro-phenyl)-3-[2-(4-methoxy-phenyl)-acetyl]-1,2,3,3a-tetrahydro-3,5,8a-triaza-cyclopenta[a]inden-8-one;
3a-(4-chloro-phenyl)-3-(4-fluoro-benzoyl)-5-oxy-1,2,3,3a-tetrahydro-3,5,8a-triaza-cyclopenta[a]inden-8-one;
3-(4-fluoro-benzoyl)-3a-(4-methoxy-phenyl)-1,2,3,3a-tetrahydro-3,6,8a-triaza-cyclopenta[a]inden-8-one;
3a-(4-bromo-phenyl)-3-(4-fluoro-benzoyl)-1,2,3,3a-tetrahydro-3,5,8a-triaza-cyclopenta[a]inden-8-one;
3a-(4-bromo-phenyl)-3-(4-fluoro-benzoyl)-1,2,3,3a-tetrahydro-3,6,8a-triaza-cyclopenta[a]inden-8-one;
9b-(4-chloro-phenyl)-1-(4-fluoro-benzoyl)-1,2,3,9b-tetrahydroimidazo[1',2':1,2]-pyrrolo[3,4-b]pyridin-5-one;
3a-(4-ethyl-phenyl)-3-(4-fluoro-benzoyl)-1,2,3,3a-tetrahydro-3,5,8a-triaza-cyclopenta[a]inden-8-one;
3a-(4-chloro-phenyl)-3-(pyridine-3-carbonyl)-1,2,3,3a-tetrahydro-3,5,8a-triaza-cyclopenta[a]inden-8-one;
3a-(4-chloro-phenyl)-3-(6-chloro-pyridine-3-carbonyl)-1,2,3,3a-tetrahydro-3,5,8a-triaza-cyclopenta[a]inden-8-one;
3a-(4-chloro-phenyl)-3-(6-chloro-pyridazine-3-carbonyl)-1,2,3,3a-tetrahydro-3,5,8a-triaza-cyclopenta[a]inden-8-one;
3a-(4-bromo-phenyl)-3-(6-fluoro-pyridine-3-carbonyl)-1,2,3,3a-tetrahydro-3,5,8a-triaza-cyclopenta[a]inden-8-one;
3a-(4-bromo-phenyl)-3-(6-fluoro-pyridine-3-carbonyl)-1,2,3,3a-tetrahydro-3,6,8a-triaza-cyclopenta[a]inden-8-one;
3a-(4-chloro-phenyl)-3-(6-fluoro-pyridine-3-carbonyl)-1,2,3,3a-tetrahydro-3,5,8a-triaza-cyclopenta[a]inden-8-one;
9b-(4-chloro-phenyl)-1-(6-fluoro-pyridine-3-carbonyl)-1,2,3,9b-tetrahydroimidazo[1',2':1,2]pyrrolo[3,4-b]pyridin-5-one;
9b-(4-chloro-phenyl)-1-(6-fluoro-pyridine-3-carbonyl)-1,2,3,9b-tetrahydroimidazo[1',2':1,5]pyrrolo[3,4-b]pyridin-5-one;
3a-(4-ethyl-phenyl)-3-[2-(4-methoxy-phenyl)-acetyl]-1,2,3,3a-tetrahydro-3,5,8a-triaza-cyclopenta[a]inden-8-one;
3a-(4-ethyl-phenyl)-3-(4-fluoro-benzoyl)-5-oxy-1,2,3,3a-tetrahydro-3,5,8a-triaza-cyclopenta[a]inden-8-one;
3a-(4-ethyl-phenyl)-3-[2-(4-methoxy-phenyl)-acetyl]-5-oxy-1,2,3,3a-tetrahydro-3,5,8a-triaza-cyclopenta[a]inden-8-one;
3a-(4-ethyl-phenyl)-3-(6-fluoro-pyridine-3-carbonyl)-1,2,3,3a-tetrahydro-3,5,8a-triaza-cyclopenta[a]inden-8-one;
3a-(4-chloro-phenyl)-3-(6-phenoxy-pyridine-3-carbonyl)-1,2,3,3a-tetrahydro-3,5,8a-triaza-cyclopenta[a]inden-8-one;
3a-(4-chloro-phenyl)-3-(2-thiophen-2-yl-thiazole-4-carbonyl)-1,2,3,3a-tetrahydro-3,5,8a-triaza-cyclopenta[a]inden-8-one;
3a-(4-chloro-phenyl)-3-(4,5,6,7-tetrahydro-benzo[c]thiophene-1-carbonyl)-1,2,3,3a-tetrahydro-3,5,8a-triaza-cyclopenta[a]inden-8-one;
3-(benzo[b]thiophene-3-carbonyl)-3a-(4-chloro-phenyl)-1,2,3,3a-tetrahydro-3,5,8a-triaza-cyclopenta[a]inden-8-one;
3a-(4-chloro-phenyl)-3-(quinoline-2-carbonyl)-1,2,3,3a-tetrahydro-3,5,8a-triaza-cyclopenta[a]inden-8-one;
3a-(4-chloro-phenyl)-3-(2-pyridin-3-yl-thiazole-4-carbonyl)-1,2,3,3a-tetrahydro-3,5,8a-triaza-cyclopenta[a]inden-8-one;
3a-(4-chloro-phenyl)-3-(5-methyl-isoxazole-3-carbonyl)-1,2,3,3a-tetrahydro-3,5,8a-triaza-cyclopenta[a]inden-8-one;
3a-(4-chloro-phenyl)-3-(6-morpholin-4-yl-pyridine-3-carbonyl)-1,2,3,3a-tetrahydro-3,5,8a-triaza-cyclopenta[a]inden-8-one;
3a-(4-chloro-phenyl)-3-(1,3-dimethyl-1H-thieno[2,3-c]pyrazole-5-carbonyl)-1,2,3,3a-tetrahydro-3,5,8a-triaza-cyclopenta[a]inden-8-one;
3a-(4-chloro-phenyl)-3-(5-methyl-2-trifluoromethyl-furan-3-carbonyl)-1,2,3,3a-tetrahydro-3,5,8a-triaza-cyclopenta[a]inden-8-one;
3a-(4-chloro-phenyl)-3-(4-methyl-[1,2,3]thiadiazole-5-carbonyl)-1,2,3,3a-tetrahydro-3,5,8a-triaza-cyclopenta[a]inden-8-one;
3a-(4-chloro-phenyl)-3-(5-methyl-2-phenyl-2H-[1,2,3]triazole-4-carbonyl)-1,2,3,3a-tetrahydro-3,5,8a-triaza-cyclopenta[a]inden-8-one;
3a-(4-chloro-phenyl)-3-(5-phenyl-thiophene-2-carbonyl)-1,2,3,3a-tetrahydro-3,5,8a-triaza-cyclopenta[a]inden-8-one;
3a-(4-chloro-phenyl)-3-(4-phenyl-[1,2,3]thiadiazole-5-carbonyl)-1,2,3,3a-tetrahydro-3,5,8a-triaza-cyclopenta[a]inden-8-one;

3a-(4-chloro-phenyl)-3-[1-(4-fluoro-phenyl)-5-methyl-1H-pyrazole-4-carbonyl]-1,2,3,3a-tetrahydro-3,5,8a-triaza-cyclopenta[a]inden-8-one;

3a-(4-chloro-phenyl)-3-(2-phenyl-thiazole-4-carbonyl)-1,2,3,3a-tetrahydro-3,5,8a-triaza-cyclopenta[a]inden-8-one;

3a-(4-chloro-phenyl)-3-(3,5-dimethyl-isoxazole-4-carbonyl)-1,2,3,3a-tetrahydro-3,5,8a-triaza-cyclopenta[a]inden-8-one;

3a-(4-chloro-phenyl)-3-(1,3,5-trimethyl-1H-pyrazole-4-carbonyl)-1,2,3,3a-tetrahydro-3,5,8a-triaza-cyclopenta[a]inden-8-one;

3a-(4-chloro-phenyl)-3-(2-methyl-5-phenyl-furan-3-carbonyl)-1,2,3,3a-tetrahydro-3,5,8a-triaza-cyclopenta[a]inden-8-one;

3-[2-(4-chloro-phenoxy)-pyridine-3-carbonyl]-3a-(4-chloro-phenyl)-1,2,3,3a-tetrahydro-3,5,8a-triaza-cyclopenta[a]inden-8-one;

3a-(4-chloro-phenyl)-3-[2-(4-fluoro-phenoxy)-pyridine-3-carbonyl]-1,2,3,3a-tetrahydro-3,5,8a-triaza-cyclopenta[a]inden-8-one;

3a-(4-chloro-phenyl)-3-(2-ethylsulfanyl-pyridine-3-carbonyl)-1,2,3,3a-tetrahydro-3,5,8a-triaza-cyclopenta[a]inden-8-one;

3a-(4-chloro-phenyl)-3-(2-methylsulfanyl-pyridine-3-carbonyl)-1,2,3,3a-tetrahydro-3,5,8a-triaza-cyclopenta[a]inden-8-one;

3a-(4-chloro-phenyl)-3-(2-pentylsulfanyl-pyridine-3-carbonyl)-1,2,3,3a-tetrahydro-3,5,8a-triaza-cyclopenta[a]inden-8-one;

3a-(4-chloro-phenyl)-3-(2-phenylsulfanyl-pyridine-3-carbonyl)-1,2,3,3a-tetrahydro-3,5,8a-triaza-cyclopenta[a]inden-8-one;

3a-(4-chloro-phenyl)-3-(2-propylsulfanyl-pyridine-3-carbonyl)-1,2,3,3a-tetrahydro-3,5,8a-triaza-cyclopenta[a]inden-8-one;

3a-(4-chloro-phenyl)-3-(2-p-tolylsulfanyl-pyridine-3-carbonyl)-1,2,3,3a-tetrahydro-3,5,8a-triaza-cyclopenta[a]inden-8-one;

3a-(4-chloro-phenyl)-3-(2-chloro-pyridine-3-carbonyl)-1,2,3,3a-tetrahydro-3,5,8a-triaza-cyclopenta[a]inden-8-one;

3a-(4-chloro-phenyl)-3-(2-phenoxy-pyridine-3-carbonyl)-1,2,3,3a-tetrahydro-3,5,8a-triaza-cyclopenta[a]inden-8-one;

3-(5-bromo-pyridine-3-carbonyl)-3a-(4-chloro-phenyl)-1,2,3,3a-tetrahydro-3,5,8a-triaza-cyclopenta[a]inden-8-one;

3a-(4-chloro-phenyl)-3-(5-phenylethynyl-pyridine-3-carbonyl)-1,2,3,3a-tetrahydro-3,5,8a-triaza-cyclopenta[a]inden-8-one;

3-[3a-(4-chloro-phenyl)-8-oxo-1,2,3a,8-tetrahydro-3,5,8a-triaza-cyclopenta[a]indene-3-carbonyl]-isonicotinic acid methyl ester;

3a-(4-chloro-phenyl)-3-(5-hex-1-ynyl-pyridine-3-carbonyl)-1,2,3,3a-tetrahydro-3,5,8a-triaza-cyclopenta[a]inden-8-one;

3a-(4-chloro-phenyl)-3-(5-thiophen-2-yl-pyridine-3-carbonyl)-1,2,3,3a-tetrahydro-3,5,8a-triaza-cyclopenta[a]inden-8-one;

3a-(4-chloro-phenyl)-3-[6-(2,2,2-trifluoro-ethoxy)-pyridine-3-carbonyl]-1,2,3,3a-tetrahydro-3,5,8a-triaza-cyclopenta[a]inden-8-one;

3a-(4-chloro-phenyl)-3-[3-methyl-5-(4-methyl-[1,2,3]thiadiazol-5-yl)-isoxazole-4-carbonyl]-1,2,3,3a-tetrahydro-3,5,8a-triaza-cyclopenta[a]inden-8-one;

3a-(4-chloro-phenyl)-3-(2,5-dimethyl-furan-3-carbonyl)-1,2,3,3a-tetrahydro-3,5,8a-triaza-cyclopenta[a]inden-8-one;

3a-(4-chloro-phenyl)-3-(furan-2-carbonyl)-1,2,3,3a-tetrahydro-3,5,8a-triaza-cyclopenta[a]inden-8-one;

3a-(4-chloro-phenyl)-3-(furan-3-carbonyl)-1,2,3,3a-tetrahydro-3,5,8a-triaza-cyclopenta[a]inden-8-one;

3a-(4-chloro-phenyl)-3-(4,5-dimethyl-furan-2-carbonyl)-1,2,3,3a-tetrahydro-3,5,8a-triaza-cyclopenta[a]inden-8-one;

3a-(4-chloro-phenyl)-3-(5-phenylethynyl-furan-2-carbonyl)-1,2,3,3a-tetrahydro-3,5,8a-triaza-cyclopenta[a]inden-8-one;

4-[3a-(4-chloro-phenyl)-8-oxo-1,2,3a,8-tetrahydro-3,5,8a-triaza-cyclopenta[a]indene-3-carbonyl]-5-methyl-furan-2-sulfonic acid dimethylamide;

3a-(4-chloro-phenyl)-3-[1-(4-chloro-phenyl)-5-methyl-1H-pyrazole-4-carbonyl]-1,2,3,3atetrahydro-3,5,8a-triaza-cyclopenta[a]inden-8-one;

3a-(4-chloro-phenyl)-3-[1-(4-methoxy-phenyl)-5-methyl-1H-pyrazole-4-carbonyl]-1,2,3,3atetrahydro-3,5,8a-triaza-cyclopenta[a]inden-8-one;

3a-(4-chloro-phenyl)-3-(2,5-dimethyl-2H-pyrazole-3-carbonyl)-1,2,3,3a-tetrahydro-3,5,8a-triaza-cyclopenta[a]inden-8-one;

3a-(4-chloro-phenyl)-3-(1,5-dimethyl-1H-pyrazole-3-carbonyl)-1,2,3,3a-tetrahydro-3,5,8a-triaza-cyclopenta[a]inden-8-one;

3a-(4-chloro-phenyl)-3-(2-ethyl-5-methyl-2H-pyrazole-3-carbonyl)-1,2,3,3a-tetrahydro-3,5,8a-triaza-cyclopenta[a]inden-8-one;

3a-(4-chloro-phenyl)-3-(2-phenyl-2H-pyrazole-3-carbonyl)-1,2,3,3a-tetrahydro-3,5,8a-triaza-cyclopenta[a]inden-8-one;

3a-(4-chloro-phenyl)-3-(1-phenyl-5-propyl-1H-pyrazole-4-carbonyl)-1,2,3,3a-tetrahydro-3,5,8a-triaza-cyclopenta[a]inden-8-one;

3-(5-tert-butyl-2-methyl-2H-pyrazole-3-carbonyl)-3a-(4-chloro-phenyl)-1,2,3,3a-tetrahydro-3,5,8a-triaza-cyclopenta[a]inden-8-one;

3-(4-bromo-2,5-dimethyl-2H-pyrazole-3-carbonyl)-3a-(4-chloro-phenyl)-1,2,3,3a-tetrahydro-3,5,8a-triaza-cyclopenta[a]inden-8-one;

3-(4-bromo-2-ethyl-5-methyl-2H-pyrazole-3-carbonyl)-3a-(4-chloro-phenyl)-1,2,3,3a-tetrahydro-3,5,8a-triaza-cyclopenta[a]inden-8-one;

3a-(4-chloro-phenyl)-3-(5-methyl-1-o-tolyl-1H-pyrazole-4-carbonyl)-1,2,3,3a-tetrahydro-3,5,8a-triaza-cyclopenta[a]inden-8-one;

3a-(4-chloro-phenyl)-3-(5-methyl-1-phenyl-1H-pyrazole-4-carbonyl)-1,2,3,3a-tetrahydro-3,5,8a-triaza-cyclopenta[a]inden-8-one;

3a-(4-chloro-phenyl)-3-(thiophene-3-carbonyl)-1,2,3,3a-tetrahydro-3,5,8a-triaza-cyclopenta[a]inden-8-one;

3a-(4-chloro-phenyl)-3-(thiophene-2-carbonyl)-1,2,3,3a-tetrahydro-3,5,8a-triaza-cyclopenta[a]inden-8-one;

3a-(4-chloro-phenyl)-3-(thieno[3,2-b]thiophene-2-carbonyl)-1,2,3,3a-tetrahydro-3,5,8a-triaza-cyclopenta[a]inden-8-one;

3a-(4-chloro-phenyl)-3-(5-pyridin-2-yl-thiophene-2-carbonyl)-1,2,3,3a-tetrahydro-3,5,8a-triaza-cyclopenta[a]inden-8-one;

3a-(4-chloro-phenyl)-3-(5-nitro-thiophene-3-carbonyl)-1,2,3,3a-tetrahydro-3,5,8a-triaza-cyclopenta[a]inden-8-one;

3a-(4-chloro-phenyl)-3-(5-nitro-benzo[b]thiophene-2-carbonyl)-1,2,3,3a-tetrahydro-3,5,8a-triaza-cyclopenta[a]inden-8-one;
3-(5-chloro-4-methoxy-thiophene-3-carbonyl)-3a-(4-chloro-phenyl)-1,2,3,3a-tetrahydro-3,5,8a-triaza-cyclopenta[a]inden-8-one;
3-(5-bromo-thiophene-2-carbonyl)-3a-(4-chloro-phenyl)-1,2,3,3a-tetrahydro-3,5,8a-triaza-cyclopenta[a]inden-8-one;
3-(5-bromo-4-methoxy-thiophene-3-carbonyl)-3a-(4-chloro-phenyl)-1,2,3,3a-tetrahydro-3,5,8a-triaza-cyclopenta[a]inden-8-one;
3a-(4-chloro-phenyl)-3-(5-methanesulfonyl-thiophene-2-carbonyl)-1,2,3,3a-tetrahydro-3,5,8a-triaza-cyclopenta[a]inden-8-one;
3a-(4-chloro-phenyl)-3-[5-(2-methyl-thiazol-4-yl)-thiophene-2-carbonyl]-1,2,3,3a-tetrahydro-3,5,8a-triaza-cyclopenta[a]inden-8-one;
3a-(4-chloro-phenyl)-3-(4-methoxy-thiophene-3-carbonyl)-1,2,3,3a-tetrahydro-3,5,8a-triaza-cyclopenta[a]inden-8-one;
3a-(4-chloro-phenyl)-3-(3-chloro-thiophene-2-carbonyl)-1,2,3,3a-tetrahydro-3,5,8a-triaza-cyclopenta[a]inden-8-one;
3-(3-chloro-4-methanesulfonyl-thiophene-2-carbonyl)-3a-(4-chloro-phenyl)-1,2,3,3a-tetrahydro-3,5,8a-triaza-cyclopenta[a]inden-8-one;
3a-(4-chloro-phenyl)-3-(2-methyl-thiazole-4-carbonyl)-1,2,3,3a-tetrahydro-3,5,8a-triaza-cyclopenta[a]inden-8-one;
3-(3-bromo-thiophene-2-carbonyl)-3a-(4-chloro-phenyl)-1,2,3,3a-tetrahydro-3,5,8a-triaza-cyclopenta[a]inden-8-one;
3-([2,2']bithiophenyl-5-carbonyl)-3a-(4-chloro-phenyl)-1,2,3,3a-tetrahydro-3,5,8a-triaza-cyclopenta[a]inden-8-one;
3-(benzo[b]thiophene-2-carbonyl)-3a-(4-chloro-phenyl)-1,2,3,3a-tetrahydro-3,5,8a-triaza-cyclopenta[a]inden-8-one;
3a-(4-chloro-phenyl)-3-(isoxazole-5-carbonyl)-1,2,3,3a-tetrahydro-3,5,8a-triaza-cyclopenta[a]inden-8-one;
3a-(4-chloro-phenyl)-3-(3-ethoxy-thiophene-2-carbonyl)-1,2,3,3a-tetrahydro-3,5,8a-triaza-cyclopenta[a]inden-8-one;
3-(3-chloro-4-methyl-thiophene-2-carbonyl)-3a-(4-chloro-phenyl)-1,2,3,3a-tetrahydro-3,5,8a-triaza-cyclopenta[a]inden-8-one;
3a-(4-chloro-phenyl)-3-(3-methyl-5-phenyl-isoxazole-4-carbonyl)-1,2,3,3a-tetrahydro-3,5,8a-triaza-cyclopenta[a]inden-8-one;
6-[3a-(4-chloro-phenyl)-8-oxo-1,2,3a,8-tetrahydro-3,5,8a-triaza-cyclopenta[a]indene-3-carbonyl]-nicotinic acid methyl ester;
3a-(4-chloro-phenyl)-3-(6-chloro-pyridine-2-carbonyl)-1,2,3,3a-tetrahydro-3,5,8a-triaza-cyclopenta[a]inden-8-one;
3-(5-chloro-2-methylsulfanyl-pyrimidine-4-carbonyl)-3a-(4-chloro-phenyl)-1,2,3,3a-tetrahydro-3,5,8a-triaza-cyclopenta[a]inden-8-one;
3a-(4-chloro-phenyl)-3-(pyridine-2-carbonyl)-1,2,3,3a-tetrahydro-3,5,8a-triaza-cyclopenta[a]inden-8-one;
3a-(4-chloro-phenyl)-3-([1,2,3]thiadiazole-4-carbonyl)-1,2,3,3a-tetrahydro-3,5,8a-triaza-cyclopenta[a]inden-8-one;
3a-(4-chloro-phenyl)-3-(2-pyridin-4-yl-thiazole-4-carbonyl)-1,2,3,3a-tetrahydro-3,5,8a-triaza-cyclopenta[a]inden-8-one;
3a-(4-chloro-phenyl)-3-(4-methyl-2-pyrazin-2-yl-thiazole-5-carbonyl)-1,2,3,3a-tetrahydro-3,5,8a-triaza-cyclopenta[a]inden-8-one;
3-(benzofuran-2-carbonyl)-3a-(4-chloro-phenyl)-1,2,3,3a-tetrahydro-3,5,8a-triaza-cyclopenta[a]inden-8-one;
3-(benzo[c]isoxazole-3-carbonyl)-3a-(4-chloro-phenyl)-1,2,3,3a-tetrahydro-3,5,8a-triaza-cyclopenta[a]inden-8-one;
3a-(4-chloro-phenyl)-3-(4,5-dichloro-isothiazole-3-carbonyl)-1,2,3,3a-tetrahydro-3,5,8a-triaza-cyclopenta[a]inden-8-one;
3a-(4-chloro-phenyl)-3-[5-(4-methoxy-phenyl)-oxazole-4-carbonyl]-1,2,3,3a-tetrahydro-3,5,8a-triaza-cyclopenta[a]inden-8-one;
3a-(4-chloro-phenyl)-3-(5-phenyl-oxazole-4-carbonyl)-1,2,3,3a-tetrahydro-3,5,8a-triaza-cyclopenta[a]inden-8-one;
3a-(4-chloro-phenyl)-3-(4-isopropyl-[1,2,3]thiadiazole-5-carbonyl)-1,2,3,3a-tetrahydro-3,5,8a-triaza-cyclopenta[a]inden-8-one;
3a-(4-chloro-phenyl)-3-[3-(4-methoxy-phenyl)-isoxazole-5-carbonyl]-1,2,3,3a-tetrahydro-3,5,8a-triaza-cyclopenta[a]inden-8-one;
3a-(4-chloro-phenyl)-3-[3-(4-chloro-phenyl)-isoxazole-5-carbonyl]-1,2,3,3a-tetrahydro-3,5,8a-triaza-cyclopenta[a]inden-8-one;
3a-(4-chloro-phenyl)-3-(1-methyl-3-trifluoromethyl-1H-pyrazole-4-carbonyl)-1,2,3,3a-tetrahydro-3,5,8a-triaza-cyclopenta[a]inden-8-one;
3a-(4-chloro-phenyl)-3-(4-methyl-2-pyridin-2-yl-thiazole-5-carbonyl)-1,2,3,3a-tetrahydro-3,5,8a-triaza-cyclopenta[a]inden-8-one;
3a-(4-chloro-phenyl)-3-(2-p-tolyl-thiazole-4-carbonyl)-1,2,3,3a-tetrahydro-3,5,8a-triaza-cyclopenta[a]inden-8-one;
3a-(4-chloro-phenyl)-3-(4-methyl-2-thiophen-2-yl-thiazole-5-carbonyl)-1,2,3,3a-tetrahydro-3,5,8a-triaza-cyclopenta[a]inden-8-one;
3a-(4-chloro-phenyl)-3-[2-(4-chloro-phenyl)-thiazole-4-carbonyl]-1,2,3,3a-tetrahydro-3,5,8a-triaza-cyclopenta[a]inden-8-one;
3a-(4-chloro-phenyl)-3-(3-phenyl-isoxazole-5-carbonyl)-1,2,3,3a-tetrahydro-3,5,8a-triaza-cyclopenta[a]inden-8-one;
3a-(4-chloro-phenyl)-3-(4-methyl-2-pyridin-3-yl-thiazole-5-carbonyl)-1,2,3,3a-tetrahydro-3,5,8a-triaza-cyclopenta[a]inden-8-one;
3-(2-chloro-5-isopropyl-thiazole-4-carbonyl)-3a-(4-chloro-phenyl)-1,2,3,3a-tetrahydro-3,5,8a-triaza-cyclopenta[a]inden-8-one;
3a-(4-chloro-phenyl)-3-[5-methyl-1-(4-nitro-phenyl)-1H-[1,2,4]triazole-3-carbonyl]-1,2,3,3a-tetrahydro-3,5,8a-triaza-cyclopenta[a]inden-8-one;
3a-(4-chloro-phenyl)-3-[2-(4-methoxy-phenyl)-thiazole-4-carbonyl]-1,2,3,3a-tetrahydro-3,5,8a-triaza-cyclopenta[a]inden-8-one;
3a-(4-chloro-phenyl)-3-(4-methyl-2-phenyl-thiazole-5-carbonyl)-1,2,3,3a-tetrahydro-3,5,8a-triaza-cyclopenta[a]inden-8-one;
3a-(4-chloro-phenyl)-3-(5-methyl-1H-pyrazole-3-carbonyl)-1,2,3,3a-tetrahydro-3,5,8a-triaza-cyclopenta[a]inden-8-one;
3a-(4-chloro-phenyl)-3-[3-(2-chloro-phenyl)-isoxazole-5-carbonyl]-1,2,3,3a-tetrahydro-3,5,8a-triaza-cyclopenta[a]inden-8-one;

3a-(4-chloro-phenyl)-3-(6-fluoro-pyridine-3-carbonyl)-5-oxy-1,2,3,3a-tetrahydro-3,5,8a-triaza-cyclopenta[a]inden-8-one;

3a-(4-chloro-phenyl)-3-(pyrimidine-5-carbonyl)-1,2,3,3a-tetrahydro-3,5,8a-triaza-cyclopenta[a]inden-8-one;

3a-(4-chloro-phenyl)-5-oxy-3-[2-(1-oxy-pyridin-3-yl)-thiazole-4-carbonyl]-1,2,3,3a-tetrahydro-3,5,8a-triaza-cyclopenta[a]inden-8-one;

3a-(4-chloro-phenyl)-3-(thiazole-4-carbonyl)-1,2,3,3a-tetrahydro-3,5,8a-triaza-cyclopenta[a]inden-8-one;

3a-(4-chloro-phenyl)-3-(4-methyl-furazan-3-carbonyl)-1,2,3,3a-tetrahydro-3,5,8a-triaza-cyclopenta[a]inden-8-one;

3a-(4-chloro-phenyl)-3-(5-isobutyl-isoxazole-3-carbonyl)-1,2,3,3a-tetrahydro-3,5,8a-triaza-cyclopenta[a]inden-8-one;

3a-(4-chloro-phenyl)-3-(5-isopropyl-2-phenyl-2H-pyrazole-3-carbonyl)-1,2,3,3a-tetrahydro-3,5,8a-triaza-cyclopenta[a]inden-8-one;

3a-(4-chloro-phenyl)-3-(5-furan-2-yl-isoxazole-3-carbonyl)-1,2,3,3a-tetrahydro-3,5,8a-triaza-cyclopenta[a]inden-8-one;

3a-(4-chloro-phenyl)-3-(4,5,6,7-tetrahydro-benzo[d]isoxazole-3-carbonyl)-1,2,3,3a-tetrahydro-3,5,8a-triaza-cyclopenta[a]inden-8-one;

3a-(4-chloro-phenyl)-3-(5-pyrazol-1-ylmethyl-furan-2-carbonyl)-1,2,3,3a-tetrahydro-3,5,8a-triaza-cyclopenta[a]inden-8-one;

3a-(4-chloro-phenyl)-3-[5-(4-chloro-phenyl)-isoxazole-3-carbonyl]-1,2,3,3a-tetrahydro-3,5,8a-triaza-cyclopenta[a]inden-8-one;

3a-(4-chloro-phenyl)-3-(5-phenyl-isoxazole-3-carbonyl)-1,2,3,3a-tetrahydro-3,5,8a-triaza-cyclopenta[a]inden-8-one;

3-(5-tert-butyl-2-phenyl-2H-pyrazole-3-carbonyl)-3a-(4-chloro-phenyl)-1,2,3,3a-tetrahydro-3,5,8a-triaza-cyclopenta[a]inden-8-one;

3a-(4-chloro-phenyl)-3-(4-fluoro-benzyl)-1,2,3,3a-tetrahydro-3,5,8a-triaza-cyclopenta[a]inden-8-one;

3a-(4-chloro-phenyl)-3-furan-2-ylmethyl-1,2,3,3a-tetrahydro-3,5,8a-triaza-cyclopenta[a]inden-8-one;

3a-(4-chloro-phenyl)-3-pyridin-3-ylmethyl-1,2,3,3a-tetrahydro-3,5,8a-triaza-cyclopenta[a]inden-8-one;

3a-(4-chloro-phenyl)-8-oxo-1,2,3a,8-tetrahydro-3,5,8a-triaza-cyclopenta[a]indene-3-carboxylic acid benzylamide;

3a-(4-chloro-phenyl)-8-oxo-1,2,3a,8-tetrahydro-3,5,8a-triaza-cyclopenta[a]indene-3-carboxylic acid phenylamide;

3a-(4-chloro-phenyl)-8-oxo-1,2,3a,8-tetrahydro-3,5,8a-triaza-cyclopenta[a]indene-3-carbothioic acid benzylamide;

3a-(4-chloro-phenyl)-8-oxo-1,2,3a,8-tetrahydro-3,5,8a-triaza-cyclopenta[a]indene-3-carbothioic acid phenylamide; and 3a-(4-chloro-phenyl)-3-(toluene-4-sulfonyl)-1,2,3,3a-tetrahydro-3,5,8a-triaza-cyclopenta[a]inden-8-one;

and salts or pharmaceutically acceptable derivatives thereof.

34. The compound according to claim 17 in a substantially pure optically active form.

35. The compound according to claim 22, or a salt or pharmaceutically acceptable derivative thereof, wherein $R_3$ is optionally substituted and is selected from phenyl, furyl, thienyl, oxazolyl, oxadiazolyl, thiazolyl, isoxazolyl, furazanyl, isothiazolyl, pyrazolyl, triazolyl, 1,2,3-triazolyl, thiadiazolyl, 1,2,3-thiadiazolyl, pyridyl, pyrimidinyl, and benzothienyl.

36. A pharmaceutical formulation comprising a compound of formula I according to claim 17, or a pharmaceutically acceptable salt or derivative thereof, and a pharmaceutically acceptable carrier or excipient.

\* \* \* \* \*